US012794266B2

(12) United States Patent
Pivonka et al.

(10) Patent No.: US 12,794,266 B2
(45) Date of Patent: Nov. 10, 2026

(54) METHOD OF MAKING AND USING AN APPARATUS FOR A LOCOMOTIVE MICRO-IMPLANT USING ACTIVE ELECTROMAGNETIC PROPULSION

(71) Applicant: The Board of Trustees of The Leland Stanford Junior University, Palo Alto, CA (US)

(72) Inventors: Daniel Michael Pivonka, Palo Alto, CA (US); Anatoly Anatolievich Yakovlev, Mountain View, CA (US); Ada Shuk Yan Poon, Redwood City, CA (US); Teresa H. Meng, Saratoga, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 18/610,992

(22) Filed: Mar. 20, 2024

(65) Prior Publication Data

US 2025/0062642 A1 Feb. 20, 2025

Related U.S. Application Data

(63) Continuation of application No. 17/486,323, filed on Sep. 27, 2021, now Pat. No. 11,979,028, which is a
(Continued)

(51) Int. Cl.
*H02J 50/10* (2016.01)
*A61B 1/00* (2006.01)
(Continued)

(52) U.S. Cl.
CPC .......... *H02J 50/10* (2016.02); *A61B 1/00158* (2013.01); *A61B 5/07* (2013.01);
(Continued)

(58) Field of Classification Search
CPC .. H02J 50/10; H02J 50/23; H02J 50/27; H02J 50/80; H02J 50/90; H02J 7/345;
(Continued)

(56) References Cited

U.S. PATENT DOCUMENTS

| | | | |
|---|---|---|---|
| 6,517,477 B1 | 2/2003 | Wendlandt | |
| 6,809,701 B2 | 10/2004 | Amundson et al. | |

(Continued)

FOREIGN PATENT DOCUMENTS

| | | | | |
|---|---|---|---|---|
| CN | 1214136 A | 4/1999 | | |
| EP | 2414040 B1 * | 8/2015 | ............. | H02J 50/10 |

OTHER PUBLICATIONS

O'Driscoll et al., "Neurons to Silicon: Implantable Prosthesis Processor", Silicon for Bioldogy, IEEE International Solid S-State Circuits Conference, Stanford University,Feb. 8, 2006, Section 30.1.

(Continued)

*Primary Examiner* — Daniel Cavallari
(74) *Attorney, Agent, or Firm* — Pillsbury Winthrop Shaw Pittman LLP

(57) ABSTRACT

Described is a locomotive implant for usage within a predetermined magnetic field. In one embodiment magnetohydrodynamics is used to generate thrust with a plurality of electrodes. In another embodiment, asymmetric drag forces are used to generate thrust.

13 Claims, 40 Drawing Sheets

Related U.S. Application Data continuation of application No. 16/865,897, filed on May 4, 2020, now Pat. No. 11,133,709, which is a continuation of application No. 15/217,815, filed on Jul. 22, 2016, now Pat. No. 10,644,539, which is a continuation of application No. 13/591,188, filed on Aug. 21, 2012, now Pat. No. 9,433,750, which is a continuation-in-part of application No. 12/485,654, filed on Jun. 16, 2009, now Pat. No. 8,504,138, and a continuation-in-part of application No. 12/485,641, filed on Jun. 16, 2009, now Pat. No. 8,634,928.

(51) Int. Cl.

| | |
|---|---|
| ***A61B 5/07*** | (2006.01) |
| ***A61M 25/01*** | (2006.01) |
| ***A61M 31/00*** | (2006.01) |
| ***H02J 50/23*** | (2016.01) |
| ***H02J 50/27*** | (2016.01) |
| ***H02J 50/80*** | (2016.01) |
| ***H02J 50/90*** | (2016.01) |
| *H02J 7/34* | (2006.01) |
| *H02J 105/46* | (2026.01) |

(52) U.S. Cl.
CPC .... *A61M 25/0116* (2013.01); *A61M 25/0127* (2013.01); *A61M 31/002* (2013.01); *H02J 50/23* (2016.02); *H02J 50/27* (2016.02); *H02J 50/80* (2016.02); *H02J 50/90* (2016.02); *H02J 7/345* (2013.01); *H02J 2105/46* (2026.01)

(58) Field of Classification Search
CPC .... H02J 2310/23; A61B 1/00158; A61B 5/07; A61M 25/0116; A61M 25/0127; A61M 31/002
See application file for complete search history.

(56) References Cited

U.S. PATENT DOCUMENTS

| | | | | |
|---|---|---|---|---|
| 6,939,290 | B2 | 9/2005 | Iddan | |
| 7,409,245 | B1 | 8/2008 | Larson et al. | |
| 8,504,138 | B1 | 8/2013 | Pivonka et al. | |
| 8,634,928 | B1 | 1/2014 | O'Driscoll et al. | |
| 9,308,377 | B1 | 4/2016 | Schaefer | |
| 9,433,750 | B2 | 9/2016 | Pivonka et al. | |
| 9,601,946 | B2 * | 3/2017 | Bae | H02J 50/12 |
| 2003/0078634 | A1 | 4/2003 | Schulman et al. | |
| 2003/0214580 | A1 | 11/2003 | Iddan | |
| 2007/0129767 | A1 | 6/2007 | Wahlstrand | |
| 2009/0118757 | A1 | 5/2009 | Burnett et al. | |
| 2010/0045114 | A1 | 2/2010 | Sample et al. | |
| 2010/0225174 | A1 | 9/2010 | Jiang | |
| 2010/0298635 | A1 | 11/2010 | Hata et al. | |
| 2011/0004278 | A1 | 1/2011 | Aghassian et al. | |
| 2011/0193688 | A1 | 8/2011 | Forsell | |
| 2012/0049648 | A1 * | 3/2012 | Choi | H02J 50/70 307/104 |
| 2013/0225077 | A1 * | 8/2013 | Schultz | H04B 5/79 455/41.1 |
| 2013/0238048 | A1 | 9/2013 | Almendinger et al. | |
| 2013/0253612 | A1 * | 9/2013 | Chow | A61N 1/3787 607/60 |
| 2014/0194058 | A1 * | 7/2014 | Lee | H04B 5/79 455/41.1 |
| 2015/0222127 | A1 | 8/2015 | Hansen | |
| 2023/0046820 | A1 | 2/2023 | Akinin et al. | |

OTHER PUBLICATIONS

Poon et al., "Optimal Frequency for Wireless Power Transmission into Dispersive Tissue", Annual International Conference of the IEEE Engineering in Medicine and Biology Society, Lyon France, Aug. 2007, pp. 1-12.
Pivonka et al., "Translating Electromagnetic Torque into Controlled Motion for Use in Medical Implants", IEEE, 32nd Annual International Conf. of IEEE EMBA, Aug. 31-Sep. 4, 2010, pp. 6433-6436.
Pivonka et al., "Locomotive Micro-Implant with Active Electromanetic Propulsion", 31st Annual International Conf. of the IEEE EMB, Sep. 2-Sep. 6, 2009, pp. 6404-6407.
Pivonka et al., "A mm-Sized Wirelessly Powered and Remotely Controlled Locomotive Implant", May 21, 2012, pp. 1-10.
Yakovlev et al., "A mm-Sized Wirelessly Powered and Remotely Controlled Locomotive Implantable Device", 2012 IEEE International Solid-State Circuits Conf., Session 17—Diagnostic and Therapeutic Technologies for Health, 2012, pp. 18-20.

* cited by examiner

MHD Figures

Asymmetric Fluid Drag Figures

Advantages of Radiating Near Field

| | Near Field | Far Field | Radiating Near Field |
|---|---|---|---|
| Gain | $\frac{1}{d^6}$ | $\frac{1}{d^2}$ | $\frac{1}{d^3}$ |
| Range | $\ll \lambda$ | $\gg \lambda$ | $\sim \lambda$ |
| Frequency | Low (1-10 MHz) | High | Relative High (.3 - 3 GHz) |
| Alignment | Sensitive | Insensitive | Relatively Insensitive |
| Spatial Patterning | No | Yes | Yes |
| Implicit Feedback | Yes | No | Yes |
| External Power Source | Yes | No | Yes |

FIG. 12

Amount Of Power That Can Be Delivered

| | |
|---|---|
| Implants | 10 μW to 1 mW |
| Glucose Sensors | 90 μW + 10 μW |
| Security ID On Pills | 30 μW + 10 μW |

METHOD OF MAKING AND USING AN APPARATUS FOR A LOCOMOTIVE MICRO-IMPLANT USING ACTIVE ELECTROMAGNETIC PROPULSION

CROSS-REFERENCE TO RELATED APPLICATION

This application is a continuation of U.S. patent application Ser. No. 17/486,323, filed Sep. 27, 2001, which is a continuation of U.S. patent application Ser. No. 16/865,897, filed May 4, 2020, which is a continuation of U.S. patent application Ser. No. 15/217,815 filed on Jul. 22, 2016 now U.S. Pat. No. 10,644,539, which is a continuation of U.S. patent application Ser. No. 13/591,188 filed on Aug. 21, 2012 now U.S. Pat. No. 9,433,750, which a continuation-in-part of U.S. application Ser. No. 12/485,654 filed Jun. 16, 2009 now U.S. Pat. No. 8,504,138, and is a continuation-in-part of U.S. application Ser. No. 12/485,641 filed Jun. 16, 2009 now U.S. Pat. No. 8,634,928, all of which are expressly fully incorporated by reference herein.

This invention was made with Government support under Contract Number HR0011-10-03-0002 awarded by the Defense Advanced Research Projects Agency. The Government has certain rights in this invention.

FIELD OF THE ART

The field of the art relate to methods of making and using an apparatus for a locomotive micro-implant using active electromagnetic propulsion.

BACKGROUND

Locomotive implantable devices have numerous applications including sensing, imaging, minimally invasive surgery, and research. Many techniques have been used to generate motion, including mechanical solutions and passive magnetic solutions. Power sources dominate the size of existing active implant technologies, and this size constraint (typically in the cm-range) limits the potential for propulsion. Additionally, mechanical propulsion is inherently inefficient at the scale of interest.

Passive locomotion schemes have circumvented the power and efficiency issues, but require large field gradients and usually cannot generate vertical motion. In a passive magnetic propulsion technique, a force is exerted on a small ferromagnetic material with magnetic field gradients. The passive propulsion method typically employs MRI-like systems because the gradient fields must be large and precisely controlled. The gradient must be in the direction of movement, and even MRI systems cannot overcome the force of gravity for devices smaller than roughly 1 mm. The force scales poorly as the size is reduced because it is proportional to the volume of the object. From a practical perspective, generating large field gradients is complicated, and current technology is inadequate.

In addition to the passive method, it is also possible to use mechanical propulsion with active power. Mechanical propulsion is accomplished with a wide variety of techniques. A few possible methods include flagella/motors, pumps, and acoustic streaming. These designs typically suffer from low conversion efficiency from input power to thrust, especially as the Reynolds number decreases. There are losses associated with the conversion from electrical power to mechanical motion, and more loss associated with the conversion from mechanical motion to forward thrust. As a result of the low efficiency, a fairly substantial amount of power is required, and the power source dominates the size making it difficult to miniaturize.

Moreover, Implantable medical devices (IMDs), such as locomotive implantable devices, are a rapidly growing area of technology. In-vivo monitoring and treatment of key biological parameters can greatly assist in managing health and preventing disease. IMDs are complete systems often incorporating signal transducers, wireless data transceivers and signal processing circuits. Power consumption in these devices requires batteries, which must be replaced periodically, or inductive power coupling antennae, both of which dominate device volume, increasing patient discomfort and severely restricting the range of viable applications.

Previous inductive powering links for IMDs operate in the low MHz requiring loop antenna diameters of a few cm and near-perfect transmitter and receiver alignment to deliver sufficient power. This choice of frequency is usually explained by saying that tissue losses become too large at higher frequencies and referring to a qualitative analysis. For these low MHz inductively coupled links the range is much less than a wavelength and thus the links satisfy the near field approximation to Maxwell's equations. Therefore resonant tuning techniques can be used to achieve the maximum energy transfer from the source to the load circuits for these links. Inductive coupling antennae of this size are viable for retinal implants where there is an existing cavity in the eye-socket but are much too large for many other IMDs such as implantable glucose sensors.

The physics behind wireless powering is described first. A time-varying current is set up on the transmit antenna. This gives rise to a time-varying magnetic field. The time-varying magnetic field, in turn, gives rise to an electric field. The electric field induces a current on the receive antenna. Then, this induced current on the receive antenna intercepts the incident electric field and/or magnetic field from the transmit antenna, and generates power at the receiver. Prior devices for wireless transmission of power to medical implants mainly operate based on inductive coupling over the near field in conjunction with a few based on electromagnetic radiation over the far field.

Devices based on inductive coupling operate at very low frequency, 10 kHz to 1 MHz. A wavelength is long relative to the size of the transmit and receive antennas. They are usually a few cm in diameter. Most energy stored in the field generated by the transmit antenna is reactive, that is, the energy will go back to the transmitter if there is no receiver to intercept the field. The separation between transmit and receive antennas is very small, usually a few mm. The low frequency and the short separation mean that there is apparently no phase change between the field at the transmitter and the incident field at the receiver. The increase in the transmit power due to the presence of the receiver mostly delivers to the receiver, like a transformer. Prior devices are therefore designed using the transformer model where various tuning techniques are proposed.

To deliver sufficient power to the implant using inductive coupling based devices, the receive antenna attached to the implant is of a few cm in diameter which is too large. It is required to be in close proximity to the transmit antenna on the external device. The power link is very sensitive to misalignment between the antennas. For example, some devices use a magnet to manually align them.

Devices based on electromagnetic radiation operate at much higher frequency, 0.5 GHz to 5 GHz. Transmit and receive antennas are on the order of a wavelength. For example, a wavelength is 12.5 cm at 2.4 GHz. Therefore, transmit and receive antennas are usually at least a few cm in diameter which is of similar size to those devices based on inductive coupling. As the transmit antenna is comparable to a wavelength, radiated power dominates. The receive antenna is in the far field of the transmit antenna and captures a very small fraction of the radiated power. That is, most of the transmit power is not delivered to the receiver. The link efficiency is very low. In return, the distance between the transmit antenna and the tissue interface is farther, a few cm to 10's of cm, the depth of the implant inside the body is larger, 1 cm to 2 cm, and the link is insensitive to misalignment between antennas. Prior devices are designed using independent transmit and receive matching networks.

The above two prior approaches have a common disadvantage: they require large receive antennas, 1 cm to a few cm. The paper by Poon et al. titled "Optimal Frequency for Wireless Power transmission over Dispersive Tissue" showed that small receive antenna is feasible. The authors show that the optimal transmission frequency for power delivery over lossy tissue is in the GHz-range for small transmit and small receive antennas (a few mm in diameter.) The optimal frequency for larger transmit antenna (a few cm in diameter) and small receive antenna is in the sub-GHz range. That is, the optimal frequencies are in between 0.5 GHz and 5 GHz. Compared with the frequency used in prior devices based on inductive coupling, the optimal frequency is about 2 orders of magnitude higher. For a fixed receive area, the efficiency can be improved by 30 dB which corresponds to a 10 times increase in the implant depth, from a few mm to a few cm. For a fixed efficiency, the receive area can be reduced by 100 times, from a few cm to a few mm in diameter. When the transmit antenna is close to the tissue interface, the separation between the transmit and the receive antenna approximately equals the implant depth. Inside the body, the wavelength is reduced. For example, a wavelength inside muscle is 1.7 cm at 2.4 GHz. Consequently, the transmit-receive separation is on the order of a wavelength. The device operates neither in the near field nor in the far field. It operates in the mid field. Furthermore, the transmit dimension of a few cm will be comparable to a wavelength.

SUMMARY

The embodiments described herein relate to methods of making and using an apparatus for a locomotive micro-implant using active electromagnetic propulsion. In one embodiment magnetohydrodynamics (MHD) is used to generate thrust. In another embodiment, asymmetric drag forces (ADF) are used to generate thrust. Devices that use a combination of the MHD and ADF are also described. Methods of using the above are also described. Additionally, the inventions described herein present apparatus and methods to deliver power wirelessly from an external device using an antenna or an antenna array to an implant. Multiple antennas can be used in the external device to maximize the power transfer efficiency. The use of multiple transmit antennas also reduces the sensitivity of the power link to the displacement and orientation of the receive antenna. These inventions as described can provide one or more of the following advantages: smaller antenna size; greater transfer distance inside body; and reduced sensitivity to misalignment between transmit and receive antennas, as the link gain is increased through choice of frequency, matching, and beam forming which requires the ability to locate the receiver.

Some MHD embodiments are provided for usage within a predetermined magnetic field and a fluid comprising: a body; a source of power disposed on or within the body; at least three fluid electrodes disposed on the body, the at least three fluid electrodes providing for a plurality of current paths within the fluid between different ones of the at least three fluid electrodes, in the presence of the predetermined magnetic field, thereby causing a force that moves the locomotive implant; and a controller disposed on or within the body and adapted to receive directional control signals and to control the plurality of current paths within the fluid using the directional control signals.

In the ADF embodiment is provided for usage within a predetermined magnetic field comprising: a body having a shape that will experience asymmetric drag forces when rotating; a source of power disposed on or within the body; at least one current loop that receives an alternating current, the alternating current causing, in the presence of the predetermined magnetic field, a force that moves the locomotive implant; and a controller disposed on or within the body and adapted to receive directional control signals and to control the alternating current in the at least one current loop using the directional control signals.

These inventions also provide a novel method to achieve feedback of information from the internal device to the external device about the location of the internal device and properties of the medium in between. Conventional techniques require explicit feedback of information from the internal device to the external device. The present invention achieves implicit feedback by exploiting the fact that the internal device is close to the external device, and therefore the external device should be able to sense the presence of the internal device and properties of the medium in between.

In one aspect there is provided apparatus and methods for applying simultaneous conjugate matching to wireless links. In another aspect is provided adaptive tuning of that simultaneous conjugate matching. In a particular embodiment, the apparatus and methods operate with wireless power signals in the sub-GHz or the GHz-range, more specifically, in between 0.5 GHz and 5 GHz.

In a particular aspect, there is provided apparatus and methods for increasing a gain of a transmitted power signal in a wireless link when operating in a mid field wavelength that is within a range between wavelength/100 to 100*wavelength and within a medium having a complex impedance between a transmit antenna and a receive antenna. The apparatus and methods maximize the gain in the wireless link using simultaneous conjugate matching, to increase power transfer within the transmitted power signal, wherein the simultaneous conjugate matching accounts for interaction between the transmit antenna and the receive antenna, including the complex impedance of the medium between the transmit antenna and the receive antenna.

In another aspect, there is provided apparatus for wireless power transmission within an environment of unknown transmission characteristics comprising: a wireless power transmitter, the wireless power transmitter including: an adaptive match transmit circuit with a tunable impedance, which supplies a tunable impedance to a power signal having a frequency of at least 0.5 GHZ; and a wireless transmitter; and a wireless power receiver, the wireless power receiver including: a receive antenna configured to receive the transmitted power signal as a received power signal; an adaptive match receive circuit, wherein the adaptive match receive circuit receives the received power signal, and is configured to match the tunable impedance, in dependence upon the environment of unknown transmission characteristics, to thereby increase a gain of the received power signal.

In a particular aspect the adaptive match receive circuit provides a feedback signal to the adaptive match transmit circuit, wherein the feedback signal provides an indication of a gain of the power signal as received at the wireless power transmitter for a particular tuned impedance.

BRIEF DESCRIPTION OF THE DRAWINGS

These and other aspects and features will become apparent to those of ordinary skill in the art upon review of the following description of specific embodiments in conjunction with the accompanying figures, wherein:

FIG. 12 shows advantages of using radiating near field according to the present invention as contrasted to near field and far field;

DETAILED DESCRIPTION OF THE PREFERRED EMBODIMENTS

Described herein is an improved locomotive implant device, and related method, for controlling the same, which can enhance functionality for a variety of applications, as well as provide new applications, as described herein. The locomotive implant as described hereinafter can be remotely powered, remotely controlled, capable of sending and receiving data, and is highly adaptable. As this application describes improvements to that described in the previously filed U.S. application Ser. No. 12/485,654 filed Jun. 16, 2009 entitled "Method Of Making And Using An Apparatus For A Locomotive Micro-Implant Using Active Electromagnetic Propulsion", it is intended that teachings and embodiments described in that application are usable with the teaching and embodiments described herein, and will be apparent to one of ordinary skill.

I. OVERVIEW

Figure 1:
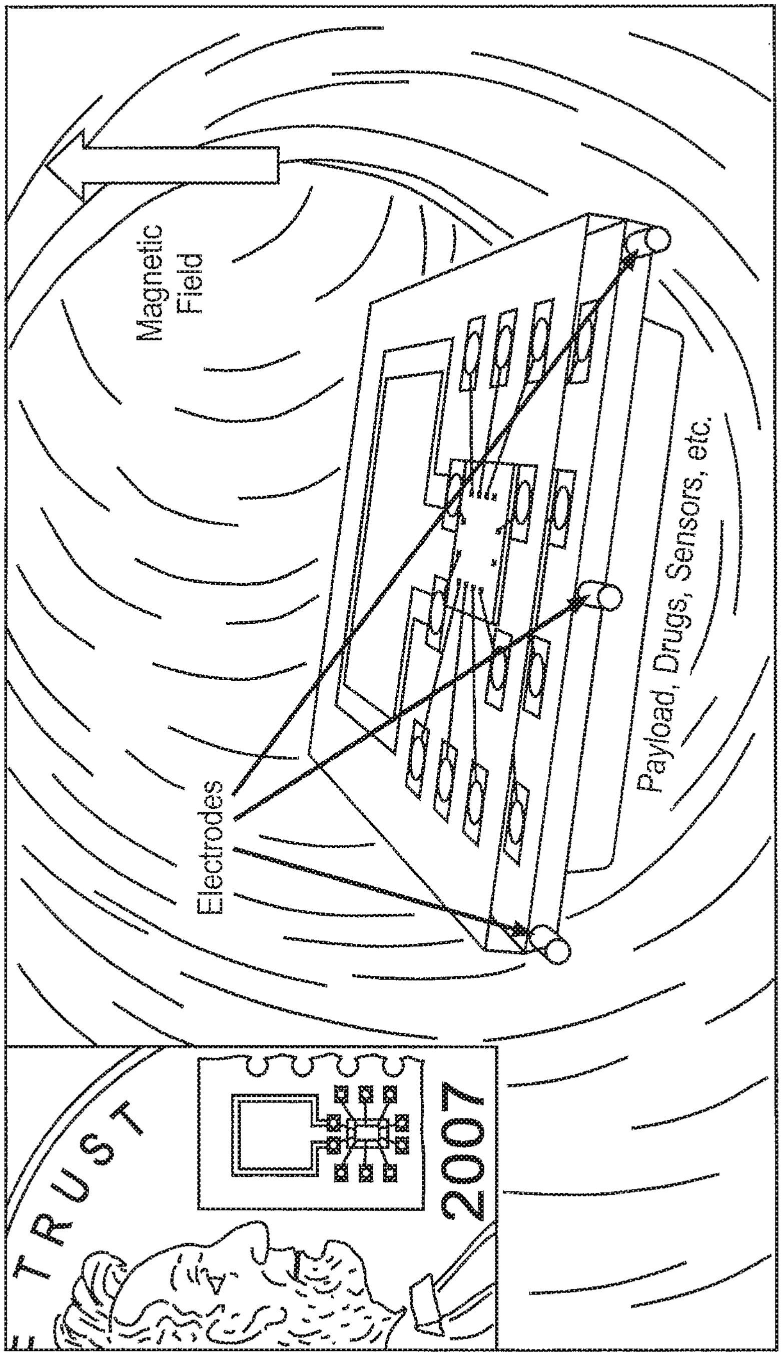
FIG. 1 illustrates a conceptual model of the FIG. 2(*b*) embodiment.

FIG. 1 shows the conceptual operation of one embodiment of an implant device travelling through the bloodstream with MHD propulsion. The implant device is comprised of a 2 mm×2 mm receive antenna and an integrated circuit that includes a matching network, a rectifier, a regulator, a demodulator, a digital controller, and high-current drivers that interface with the propulsion system. This implant device can travel through any fluid and can be navigated through the circulatory system, enabling a variety of new medical procedures. MHD propulsion can be directly steered by adjusting current flows into and out of electrodes to turn. 3D motion can be achieved by reorienting the external magnetic field, adjusting the buoyancy of the device, or by tilting the device and to create ascend or descend as the device moves. AFD propulsion can be steered by controlling and adjusting the total rotation as the device oscillates. For 3D motion, the magnetic field can be reoriented, the buoyancy can be adjusted, or it can be tilted up or down as it moves to ascend or descend.

The organization of the following descriptions is as follows. Section II presents the analysis and simulation of the fluid propulsion methods based on Lorentz forces. Section III describes the design of the wireless power transmission system as well as the data receiving architecture. The circuit implementation is presented in section IV, section V discusses the experimental results and summarizes performance, and Section VI provides other considerations.

II. ELECTROMAGNETIC PROPULSION

Propulsion for implantable devices has not been possible because of the high power requirement for mechanical designs, and the high complexity of passive magnetic designs. Our prior work based on Lorentz forces demonstrates two methods with significant advantages over existing techniques in terms of power efficiency, scalability, and controllability. The first method drives current directly through the fluid using magnetohydrodynamics (MHD), and the second switches current in a loop of wire to oscillate the device, which experiences asymmetric drag fluid forces. In both methods, the force is proportional to current, and therefore maximizing current will maximize the speed.

The thrust forces work against fluid drag forces, which are velocity dependent. This dependence varies with the Reynolds number of the fluid flow. The Reynolds number is a dimensionless representation of the ratio of the inertial forces to the viscous forces, and is given by $$Re = \frac{\rho f^{vD}}{\mu}$$

where $\rho_f$ is the density of the fluid, v is the velocity, D is a characteristic dimension, and μ is the fluid viscosity. For high Reynolds numbers (>1000), the drag force is given as $$D = \frac{1}{2}\rho f v^2 A f C_D \propto L^2$$

where $A_f$ is the frontal area of the device, and $C_D$ is the shape factor. These forces scale with area, and as will be shown, the thrust forces for both propulsion methods scale linearly with length. This means that in the high Reynolds regime, less current is needed to maintain a constant speed as the device is scaled. As the Reynolds number decreases, viscous forces become dominant. For extremely low Reynolds numbers (<1), the drag force scales linearly with the size of the device as predicted by Stokes Law. In the low Reynolds regime, the current must be kept constant as the device is scaled to maintain a constant speed. For mm-sized devices moving at cm/sec speeds in water, the Reynolds number ranges from roughly 10-100, so numerical fluid simulations are necessary for an accurate analysis of the fluid drag forces.

(a) Magnetohydrodynamic (MHD) Propulsion

Figure 2B:
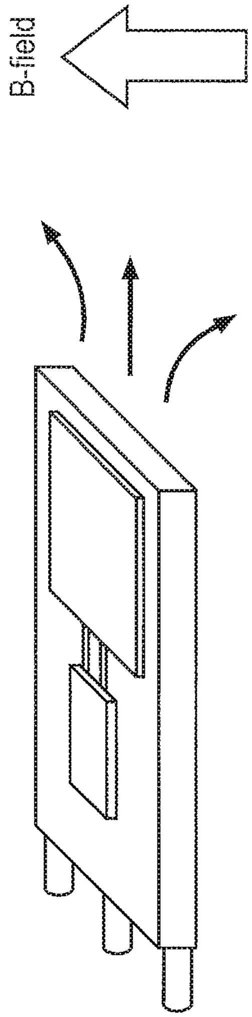
FIGS. 2(*a-c*) illustrate operation of the MHD propulsion embodiment and different embodiments of an MHD propulsion device.
Figure 2A:
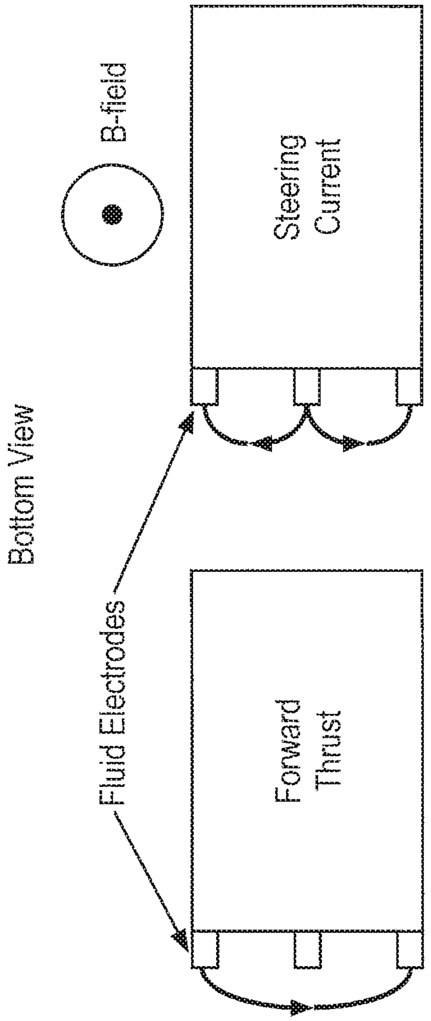
Figure 2C:
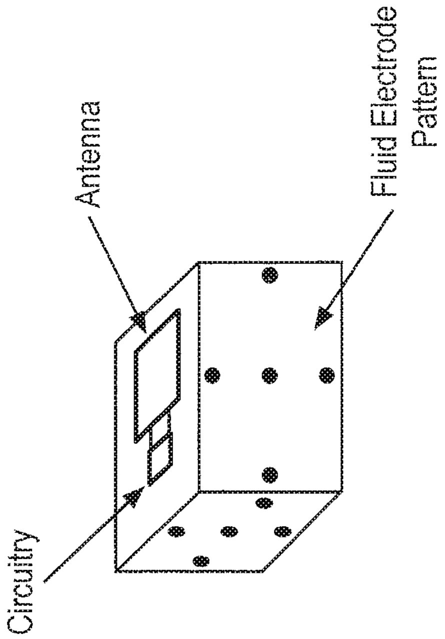

MHD propulsion drives electric currents through fluids, so the efficiency of this method depends on the fluid conductivity. The basic principle of motion is described in FIG. 2(*a*-*b*), which illustrate thrust and steering according to one embodiment. Another MHD embodiment is illustrated in FIG. 2(*c*), and while it contains a different shape and additional fluid electrode patterns, with each electrode itself being independently controlled (and there could be many more electrodes in different positions if needed), the overall principles of motion remain the same, with there being extra degrees of control and therefore movement possible with the additional electrodes in different locations, as illustrated. It is also noted that shape is much less important than for the AFD embodiment also described herein, because the propulsion forces are generated directly. As such, the MHD device can be any desired shape, though preferably it should be designed to minimize drag and simplify control.

Considerations with respect to building an MHD device, in addition to those discussed further herein, include that the MHD device can be propelled with a static field and static currents. The MHD device requires, however, conductive fluids, as efficiency improves with conductivity. Further, the fluid electrodes must be carefully selected, as the fluid electrodes must not dissolve with current flow (platinum, for example). Electrolysis should also be minimized (Voltage/current adjustments, charge balancing).

The conductivity of human blood varies approximately from 0.2 S/m to 1.5 S/m depending on the concentration of blood cells. This translates to a load of less than 300Ω at the device, which varies with the size, shape, and distance between the electrodes as well as the temperature and applied voltage. Stomach acids tend to have higher conductivities but also vary significantly with normal biological processes. In the following analysis, the required current for a given speed will be estimated as a function of the size of the device and the background magnetic field. This will give insight into the scalability of the propulsion method and also provide a design target for the circuitry.

The thrust force for MHD propulsion is the Lorentz force on the current flowing through the fluid. These forces are given in the equation below, where I is the current in the wire, L is a vector representing the length and direction of the wire, and B is the background vector magnetic field:

$$F = IL \times B$$

Figure 3:
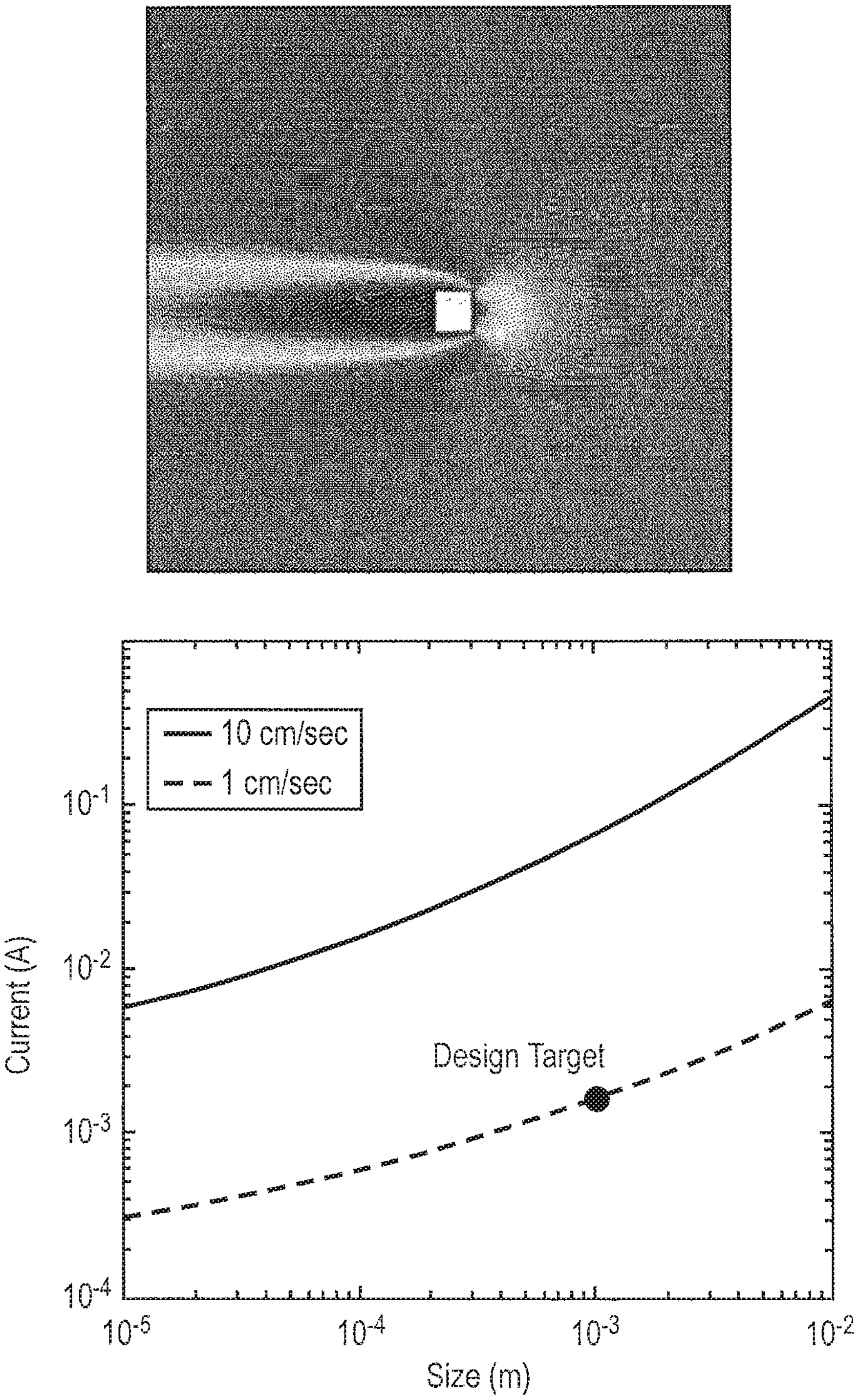
FIG. 3 illustrates simulated performance of the MHD propulsion embodiment.

These forces scale linearly with the length of the wire L, which allows for the operation of very small devices. It scales more slowly than high Reynolds drag forces, which means that for smaller devices constant current scaling results in higher speeds; and it scales evenly with low Reynolds drag forces, which means that constant current scaling results in a constant speed. Additionally, the amount of force is linearly proportional to the background magnetic field, so the performance of this method improves with stronger magnetic fields. To accurately estimate the speed, numerical simulations of the fluid mechanics are performed. Fluid simulations based on incompressible Navier-Stokes flows predict the fluid drag forces, and from these forces the steady-state velocity can be extracted. In, FIG. 3, the required current is estimated for a given speed as a function of the size of the device with a background magnetic field of 0.1 T, which can be generated with permanent magnets. This analysis shows that mm-sized devices should be able to achieve speeds on the order of cm/sec with approximately 1 mA of current.

The amount of current that can be driven is a strong function of the fluid conductivity, and has significant non-linear variations with electrode area, electrode materials, applied voltage, and the types of ions in the fluid. To drive 1 mA through blood (which has the lowest conductivity of the targeted fluids), roughly 300 mV is required, resulting in a power consumption of around 300 μW. As the fluid conductivity increases, the required power decreases. These power requirements are within the bounds of optimized wireless powering techniques through tissue, so miniaturized locomotive implantable devices are possible with this method.

(b) Asymmetric Fluid Drag Propulsion

Figure 4A:
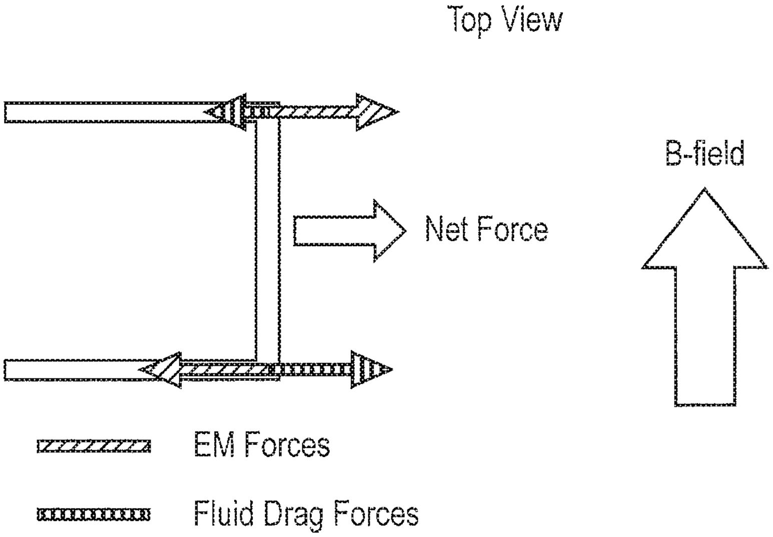
FIGS. 4(*a-c*) illustrate operation of the AFD propulsion embodiment and different embodiments of an AFD propulsion device.
Figure 4B:
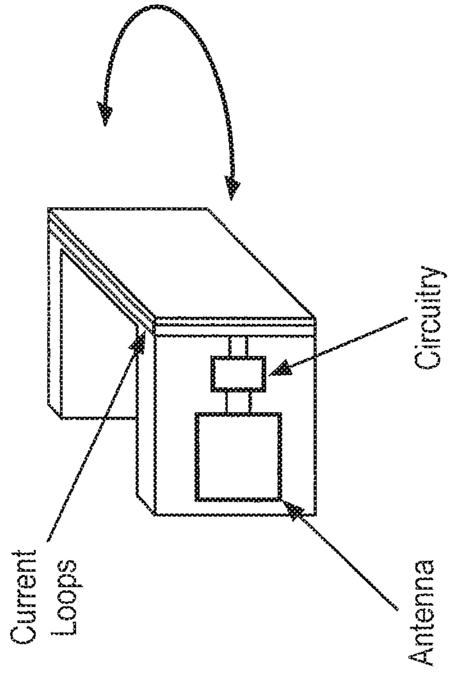
Figure 4C:
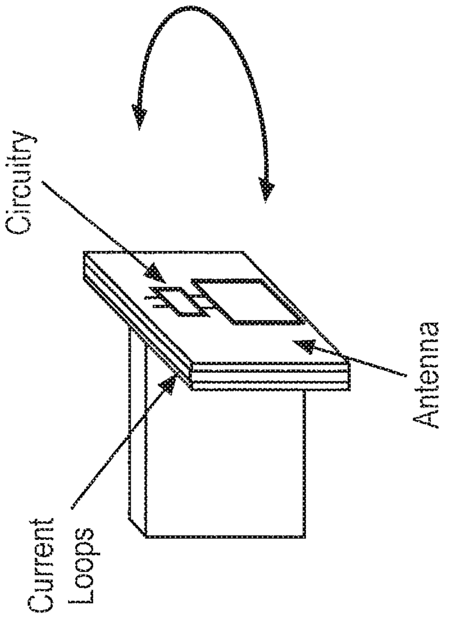

The second fluid propulsion method relies on asymmetries in fluid drag created by an oscillating asymmetric structure. The structure is oscillated by alternating currents in a loop of wire that is placed in a background magnetic field. The basic principle of operation is described in FIGS. 4(*a-b*), which illustrate thrust and steering according to one embodiment. Another AFD embodiment is illustrated in FIG. 4(*c*), to illustrate another shape that experiences asymmetric drag forces. It should be apparent that a myriad of other shapes that would also experience asymmetric drag forces are possible, though, for example a cube won't work because each side will experience the same force as it rotates. Further while FIGS. 4(*a-b*) illustrate only one set of loops that are in the same orientation, in general, a single device could have 3 loops oriented orthogonally, which would allow the device to be tilted or rotated for better steering and motion control. Essentially, more loops give more degrees of control.

Considerations with respect to an AFD device include optimizing shape for maximum difference in drag. Also, the AFD device can operate in any fluid, as efficiency is determined by viscosity, rotation frequency, and angle of rotation. Further, feedback control can greatly enhance motion of the AFD device, which can be accomplished with sensors on device or external imaging.

The forces generated with this method are a function of the fluid viscosity, which for most bodily fluids are on the same order of magnitude as water. The performance of this method is enhanced as the number of loops is increased, and the amount of current that can be driven is limited by the internal resistance of the circuitry and the amount of power delivered through the antenna. The following analysis estimates the required current as a function of the size of the device and the desired speed. This analysis predicts the device scalability and also specifies the requirements on the circuitry.

The thrust forces result from asymmetric fluid drag on a structure that oscillates with electromagnetic torque of $$\tau_{em} = IL^2 B$$

where I is the current on the loop, L is the length of the wire, and B is the background magnetic field. The asymmetry in the fluid drag is represented by the shape factor, $C_D$. By integrating the fluid drag along one side of the device, the net force can be represented as $$F \propto (C_{D,H} - C_{D,L}) L^4 \omega^2$$

where $C_{D,H}$ and $C_{D,L}$ represent the different shape factors due to the asymmetry, L is a side length of device, and ω is the rotation frequency. Assuming small angle rotations and constant angular acceleration, which is true when the electromagnetic torque dominates the fluid drag torque, the average angular velocity over a half-cycle is $$\omega_{avg} = \sqrt{\theta \tau_{em} / (4 I_{int})}$$

where θ is the angle of rotation and $I_{int}$ is the moment of inertia. Realizing that $\tau_{em} \propto L^2$ and $I_{int} \propto L^5$, constant current scaling results in the average angular velocity scaling as $\omega \propto L^{-3/2}$. Using this result in the equation for the net force, we again find that these thrust forces scale linearly with L. This method scales in the same way as MHD propulsion and allows for the operation of very small devices. As the Reynolds number decreases, the fluid drag becomes much more shape dependent, which complicates analytical analysis. For accurate estimations of the forces on these devices, we again rely on numerical simulations of the fluid mechanics.

Figure 5:
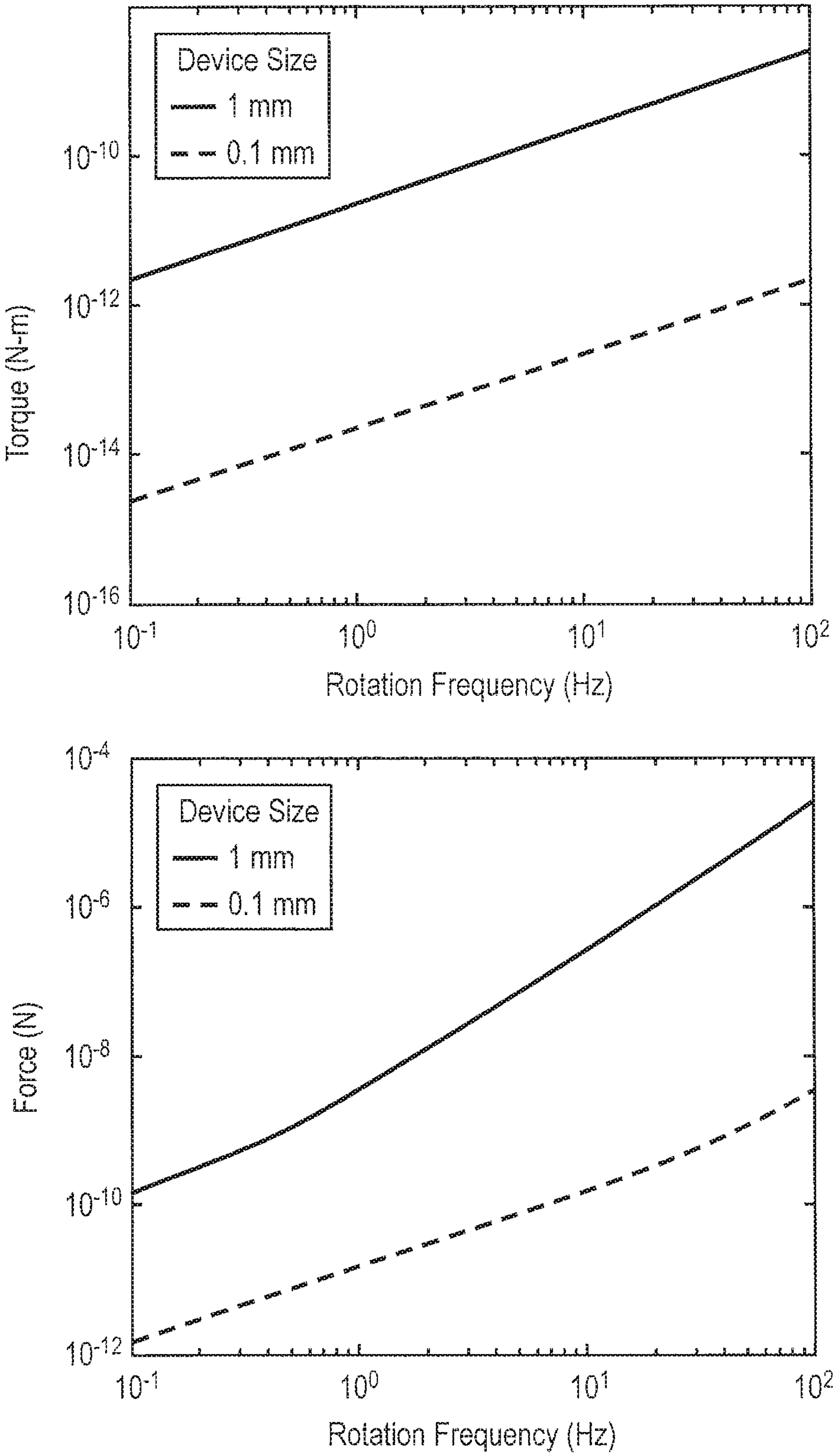
FIG. 5 illustrates simulations of drag torque and resulting net force for the AFD propulsion embodiment.
Figure 6:
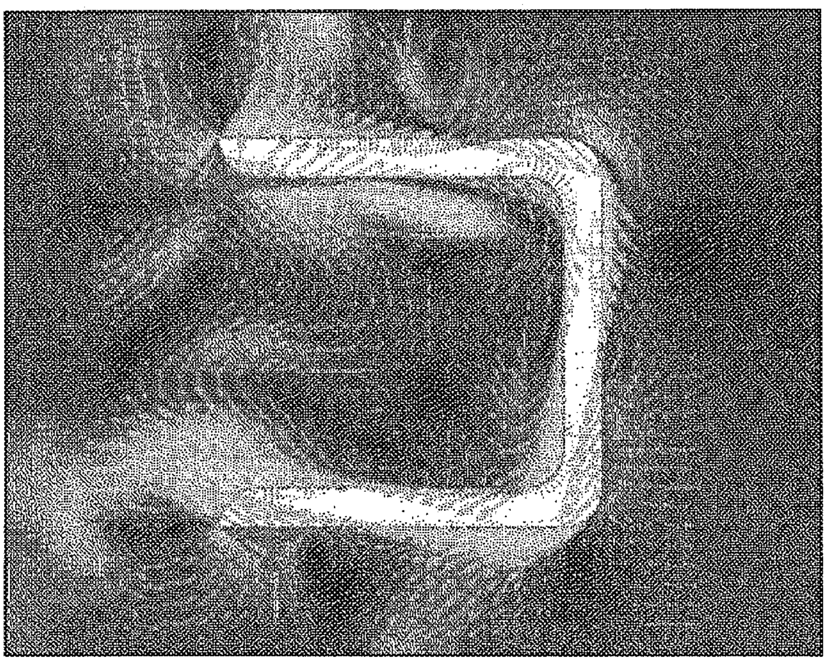
FIG. 6 illustrates simulated performance of the MHD propulsion embodiment
Figure 6:
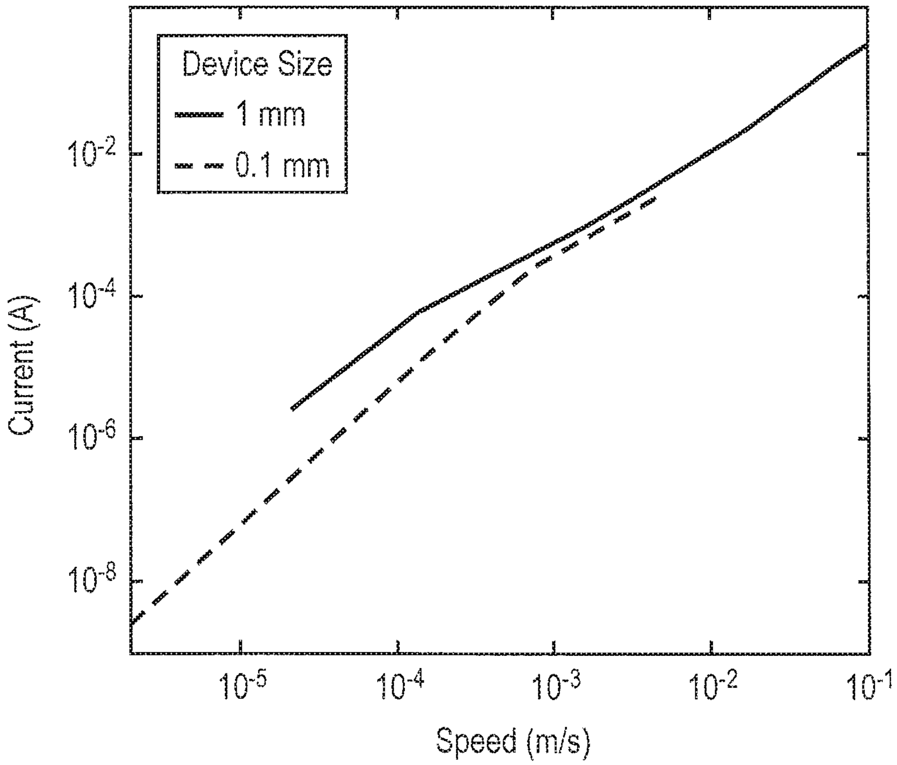

For this propulsion method, the simulations predict both the average fluid drag torque and the average net force over a cycle as a function of the rotation frequency and the size of the device. The fluid drag torque and the average force are shown in FIG. 5. These simulations agree with the predicted scaling behavior in terms of size and rotation frequency. From the fluid drag torque simulation, the current required to achieve a given rotation frequency can be estimated. The simulated net forces can then predict the speed, which relates to the current shown in FIG. 6. From these simulated results, mm-sized devices with a single loop of wire require currents of approximately 1 mA to achieve cm/sec speeds in water with a 0.1 T magnetic field. Additional loops of wire enhance the performance, essentially multiplying the current experiencing a force.

III. WIRELESS CHIP ARCHITECTURE

Some embodiments described herein are directed to wireless power transmission for implantable medical devices, and uses the recognition that high frequencies can penetrate liquids and biological tissue, and that the optimal operating frequency is a function of the depth of the receive inside the body. Thus, receive antennas as small as 2 mm2 can deliver substantial power.

Figures 7A, 7B, 7C:
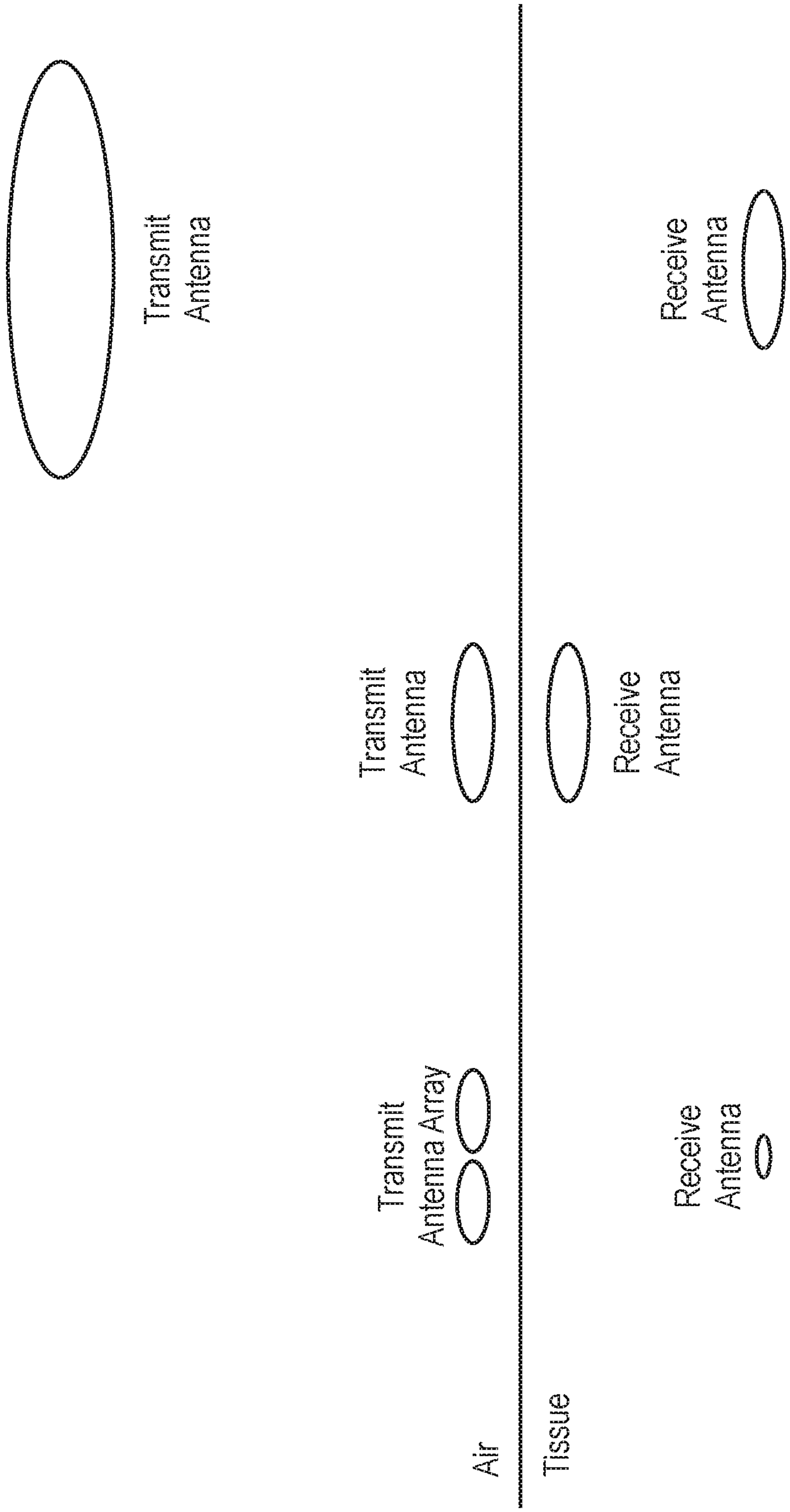
FIG. 7B Prior Art
FIG. 7C Prior Art
FIG. 7*a* illustrates relative size of the transmit and receive antennas as compared conventional transmit and receive antennas illustrated in FIGS. 7*b*-7*c*.

The present method is able to achieve the same or better efficiency as devices based on inductive coupling while the receive antenna on the implant is smaller and deeper inside the body, as illustrated in FIG. 7A and FIG. 7B. It achieves the miniaturization in the receive antenna and the extension in the transfer distance by operating in the sub-GHz or the GHz-range, more specifically, in between 0.5 GHz and 5 GHz, in a manner that provides a power-free wireless link for implants, and for battery-less implanted medical sensors.

At such high frequency, the wavelength inside body is small. As the transmit antenna is placed close to the tissue interface, we can use this wavelength as the reference wavelength for the design of the transmit antenna. This wavelength is about 6 times smaller than the corresponding wavelength in air at the same frequency. The present invention, therefore, exploits wireless power delivery and data link circuits, described hereinafter, that are magnitudes smaller than conventional devices, and also can provide significantly greater transfer distance for high margin and high volume medical applications Multiple antennas can also be used in the external device to maximize the power transfer efficiency. The use of multiple transmit antennas also reduces the sensitivity of the power link to the displacement and orientation of the receive antenna. In devices based on electromagnetic radiation, the use of multiple transmit antennas is less effective due to the much longer wavelength in air. Also, the receive antennas in this invention are much smaller than those in electromagnetic radiation, as illustrated in FIG. 7A and FIG. 7C. This, the present invention can provide one or more of the following advantages: smaller antenna size; greater transfer distance inside body; and reduced sensitivity to misalignment between transmit and receive antennas, as the link gain is increased through choice of frequency, matching, and beam forming which requires the ability to locate the receiver. All of those techniques and their preferred embodiments are described to the level that a person of ordinary skill in the art could implement them.

This invention provides a novel method to achieve feedback of information from the internal device to the external device about the location of the internal device and properties of the medium in between. Conventional techniques require explicit feedback of information from the internal device to the external device. The present invention achieves implicit feedback by exploiting the fact that the internal device is close to the external device, and therefore the external device should be able to sense the presence of the internal device and properties of the medium in between. That is, the present invention does not require the explicit feedback of information from the internal device to the external device in order to adapt to the changing location of the internal device and the changing properties of the medium in between.

The present invention can be applied to any device that is powered remotely, particularly to those devices in which having to align the external and the internal antennas is undesirable. All systems and devices which utilize electric power for any purpose, including but not limited to sensing; control; actuating; processing; authenticating; lighting; and heating, could potentially benefit from this invention and where there is potential benefit in having the power source at a remote location e.g. a medical implant in which a battery can not be placed due to device size limitations and/or those systems which require two-way communication in which there is potential benefit in having the power source at a remote location. This invention should be used both as a stand-alone product and as a sub-component in larger systems.

Figure 8:
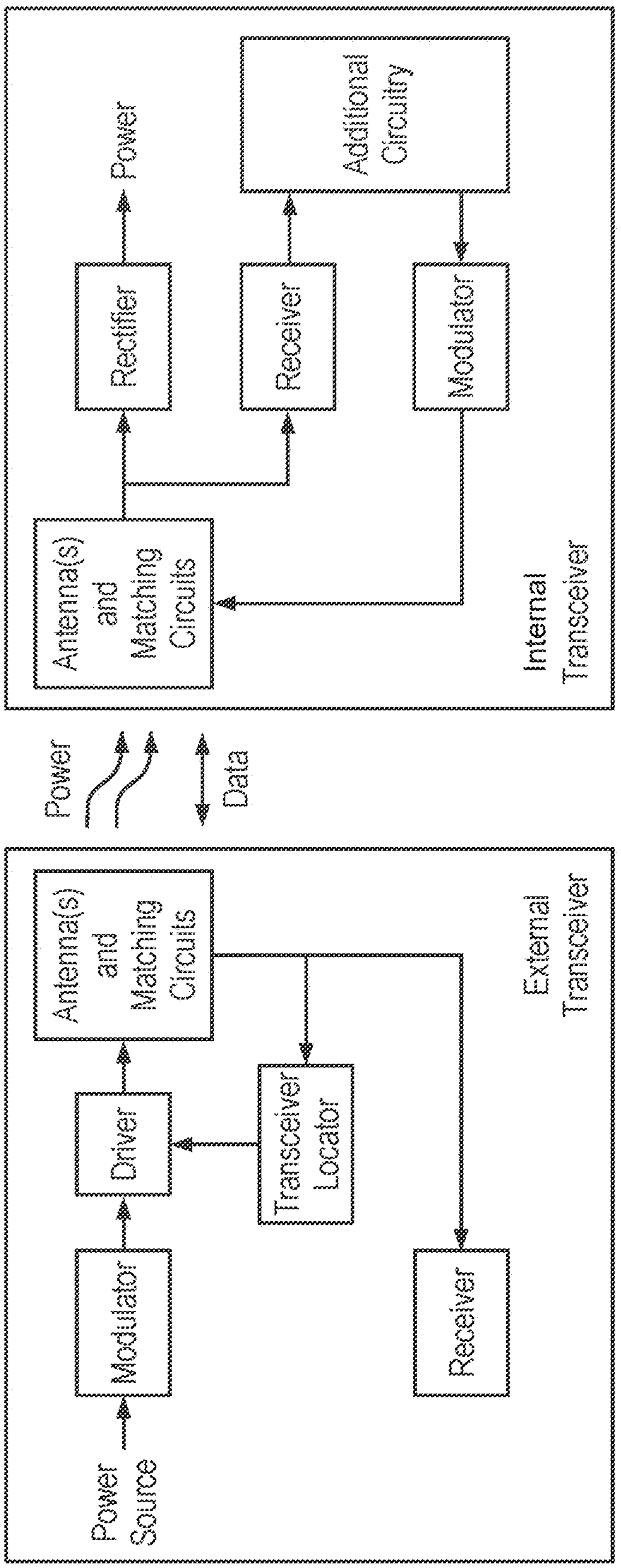
FIG. 8 illustrates a block diagram of an external transceiver and internal transceiver according to one embodiment.

FIG. 8 illustrates one embodiment of the present invention. A power source connected to electronic circuits and an antenna (or antennas), herein referred to as the external transceiver, transmits power wirelessly to a remote antenna (or antennas) and the electronic circuits they are connected to, herein referred to as the internal transceiver. The external transceiver includes: (1) a driver which takes information from the transceiver locator to provide RF signals to the antenna(s) and matching in such a way that power and data are wirelessly transferred to the internal transceiver with reduced sensitivity to the misalignment between antenna (or antennas) on the external transceiver and that (or those) on the internal transceiver; (2) antenna(s) and matching when driven by the driver generates the intended electromagnetic field; (3) a transceiver locator which senses signals from the antenna(s) and matching, and uses those signals to determine the important aspects of the location of the internal transceiver and the medium in between; (4) a modulator which modifies the waveform of the power source to encode data that is sent to the internal transceiver; and (5) a receiver which extracts data from signals sensed at the antenna(s) and matching and the data is sent from the internal transceiver. The internal transceiver includes (1) antenna(s) and matching which produce voltage and current to power the remainder of the transceiver from the field generated by the external transceiver; (2) a rectifier which converts the high frequency energy to DC; (3) a receiver which extracts data sent from the external transceiver; (4) a modulator which encodes data sent to the external transceiver either implicitly or explicitly; and (5) additional circuitry as required by the applications.

The antenna(s) and matching of the preferred embodiment functions to maximize the power transfer from the driver at the external transceiver to the rectifier at the internal transceiver. In a first variation the matching views the link as an n-port network (in the microwave circuits sense) and provides simultaneous conjugate matching between those ports and the impedances of their source/load circuits. In a second variation the matching system is the same as the first except that the matching components are adaptively varied to achieve the maximum power transfer, and thus can adapt to varying range and tissue dielectrics. In a first preferred realization of the second variation the matching networks are L-networks realized from binary weighted arrays of capacitors and inductors whose value may be chosen according to the adaptive algorithm, in this variation the steepest descent algorithm is used.

The transceiver locator of the preferred embodiment functions to sense signals from the antenna(s) and matching and uses those signals to determine the important aspects of the location of the internal transceiver, and properties of the medium in between the external and the internal transceivers.

Figure 9:
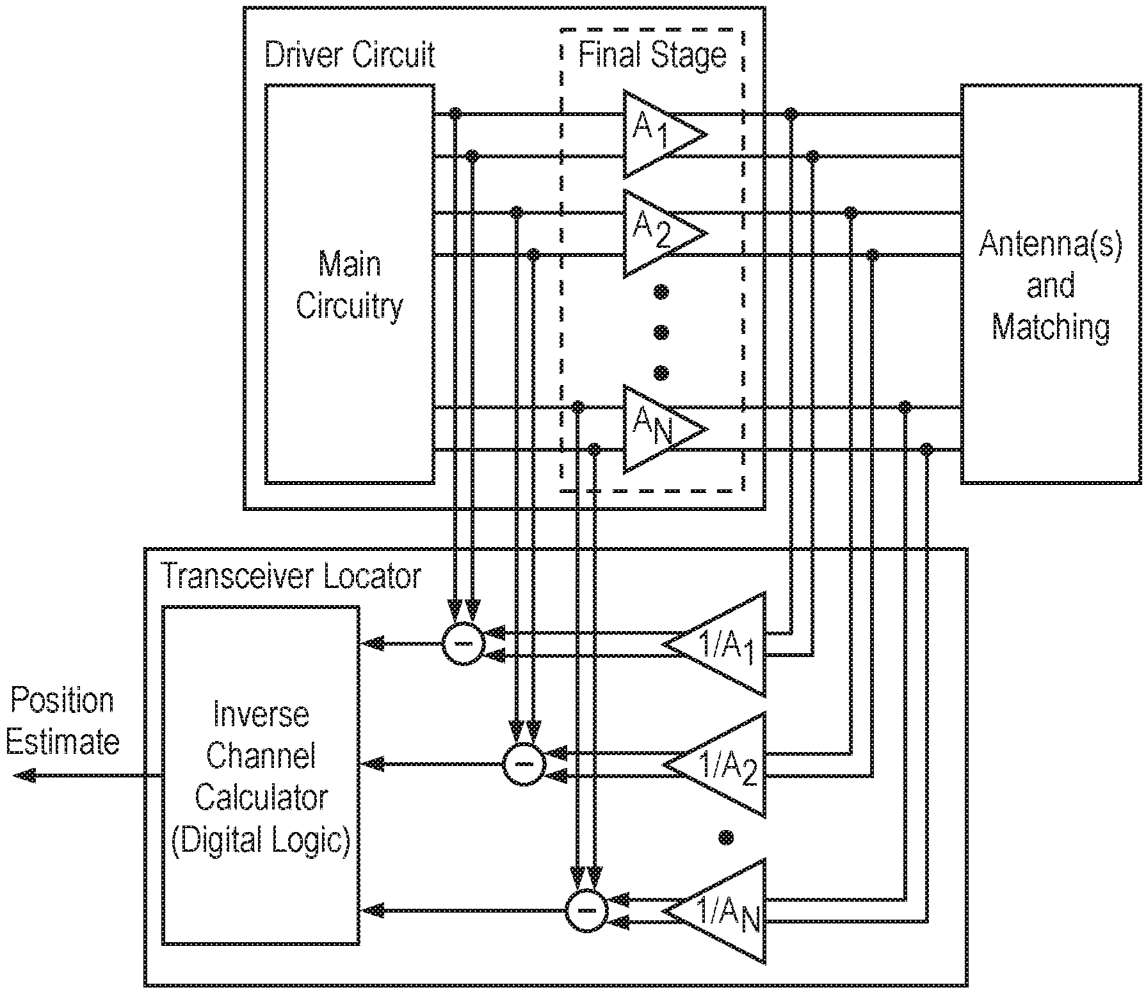
FIG. 9 illustrates a transceiver locator according to an embodiment.

The first variation of the transceiver locator operates by (1) finding the backscattered signal by subtracting the driver signals prior to the final stage from the signals observed at the antennas and matching input ports attenuated by the corresponding gains in the driver final stage, and (2) computing a channel inversion algorithm which takes that backscattered signal as input and gives the location estimate as output, as illustrated in FIG. 9. In a first preferred embodiment that attenuation is performed using amplifiers whose gain is chosen to be the inverse of the gain of the final stage amplifiers in the driver circuitry.

A second variation of the transceiver locator operates the same as the first variation except that the backscattered signal is found by amplifying the driver signals by the corresponding gains in the driver final stage in a second gain path and subtracting those amplified signals from the signals observed at the antennas and matching input ports (without any attenuation).

Figure 10:
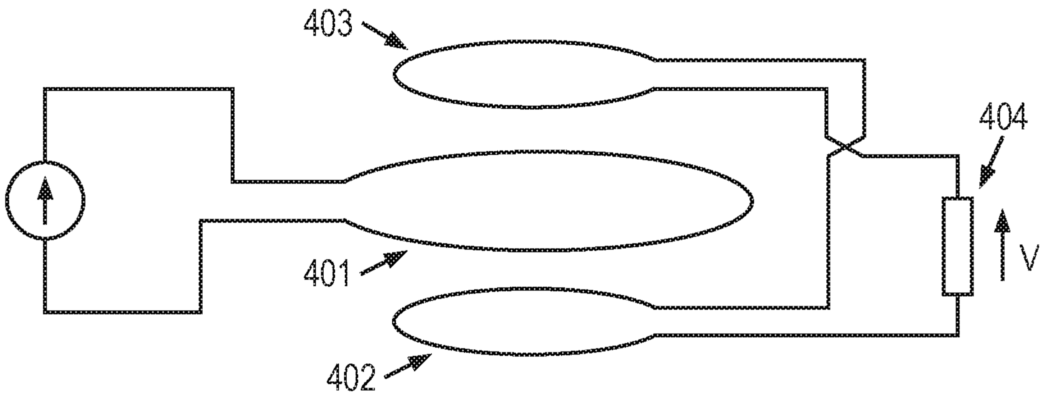
FIG. 10 illustrates a transceiver locator according to another embodiment.

A third variation of that transceiver locator operates the same as the variation first except that the backscattered signal is found using a differential antenna configuration at the external transceiver, as illustrated in FIG. 10. 401 is the transmit antenna, or one of the transmit antennas when multiple antennas are used. 402 and 403 are a pair of sensing antennas that are symmetrically placed with respect to the transmit antenna 401. The sensing antennas are connected in series-opposition. Therefore, the voltage measured across 404 is invariant to the driver signal on the transmit antenna, and gives the backscattered signal.

The driver of the preferred embodiment functions to supply the input signals to each port of the external transceiver's antenna(s) and matching network in such a way that power and data are wirelessly transferred to the internal transceiver with reduced sensitivity to the misalignment between the internal and the external antennas. The driver includes a digitally implemented algorithm, which takes the transceiver location estimate and uses it to choose the amplitude and phase of the signal driving each port.

The modulator at the internal transceiver of the preferred embodiment can operate as described in the following, although other implementations and variations can be used as well. The two preferred embodiments are: (1) encoding data by varying the impedance of the internal transceiver as seen by the external transceiver; or (2) explicitly transmitting a waveform and encoding data by varying the phase, amplitude, or frequency of the waveform.

The receiver at the external transceiver of the preferred embodiment performs its function according to the modulation schemes used by the internal transceiver. When the internal transceiver encodes data by varying its impedance, the receiver at the external transceiver can use either load modulation or backscatter modulation depending on the sensitivity of the receiver to measure the change in voltage and the change in reflected power.

EXAMPLES

This example considers the power transfer efficiency between a square transmit coil of width 2 cm and a square receive coil of width 2 mm. The transmit coils is 1 cm above the tissue interface. The tissue is modeled as a multi-layer medium. The upper layer is a 2-mm thick skin, the second layer is a 8-mm thick fat, and the lower layer is muscle. The receive coil is placed inside the muscle at a distance of 3 cm from the transmit coil. The dielectric properties of the tissue are obtained from the measurement reported in "The dielectric properties of biological tissues: III parametric models for the dielectric spectrum of tissues." Under the safety requirement of no more than 1.6 mW of power absorbed by any 1 g of tissue, the system can deliver 100 μW of power to the internal receiver which is sufficient for the operation of many applications.

Figure 11B:
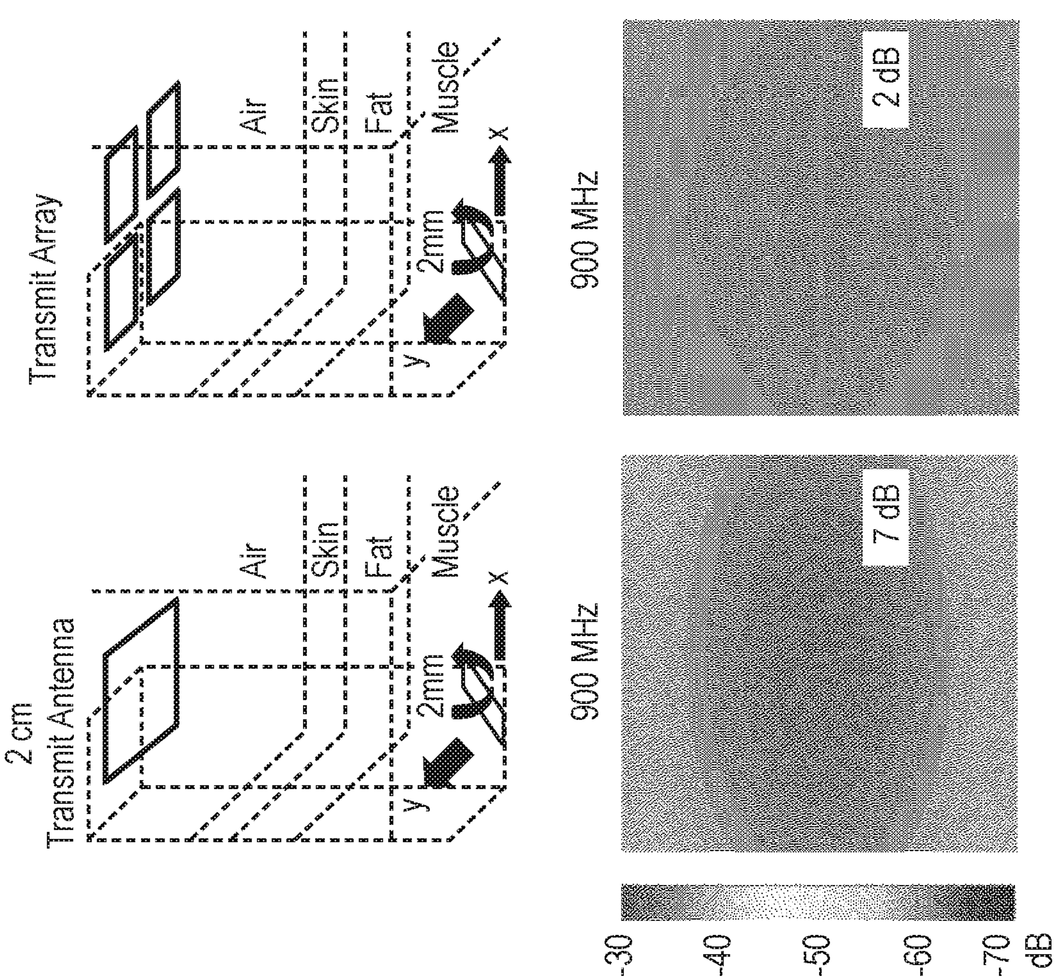
FIGS. 11*a*-11*b* illustrate variations and differences in the power transfer efficiency.
Figure 11A:
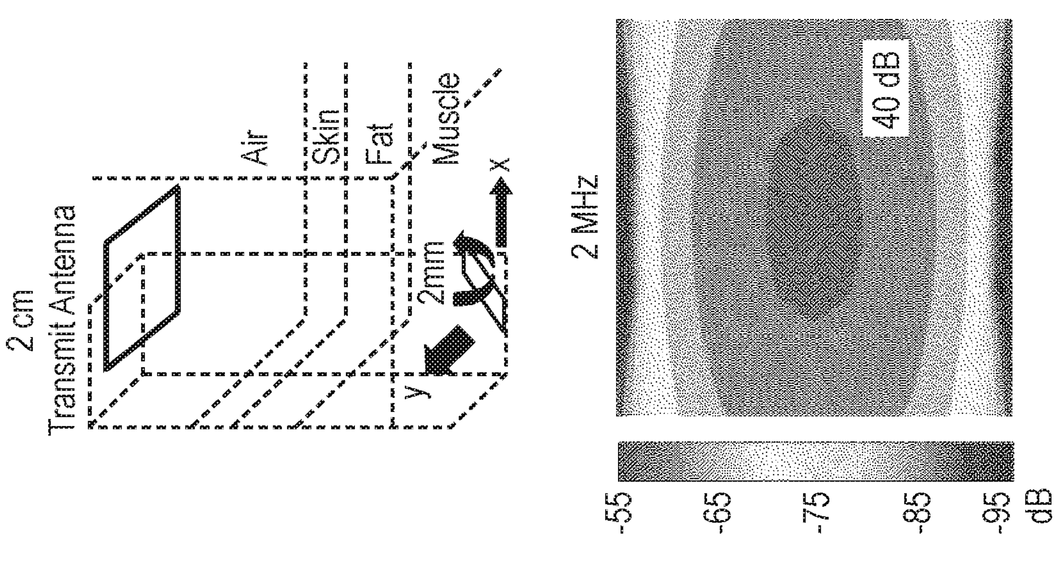

This example considers the variation of the power transfer efficiency due to displacement and orientation of the receive coil. Referred to FIG. 11, the receive coil is moved along the x-axis and the y-axis, and it is tilted by 0 to 60°. At transmission frequency of 2 MHZ, FIG. 11A shows the variation of the power transfer efficiency at different receiver location. The differences in the power transfer efficiency can be 40 dB. At transmission frequency of 900 MHz, FIG. 11B shows that the differences in the power transfer efficiency are about 7 dB. Furthermore, when multiple antennas are used at the external transceiver, the differences in the power transfer efficiency are less than 2 dB. Therefore, the present invention is relatively insensitive to the displacement and orientation of the receive antenna on the internal transceiver.

FIG. 12 shows advantages of using radiating near field according to the present invention as contrasted to near field and far field.

Figure 13:
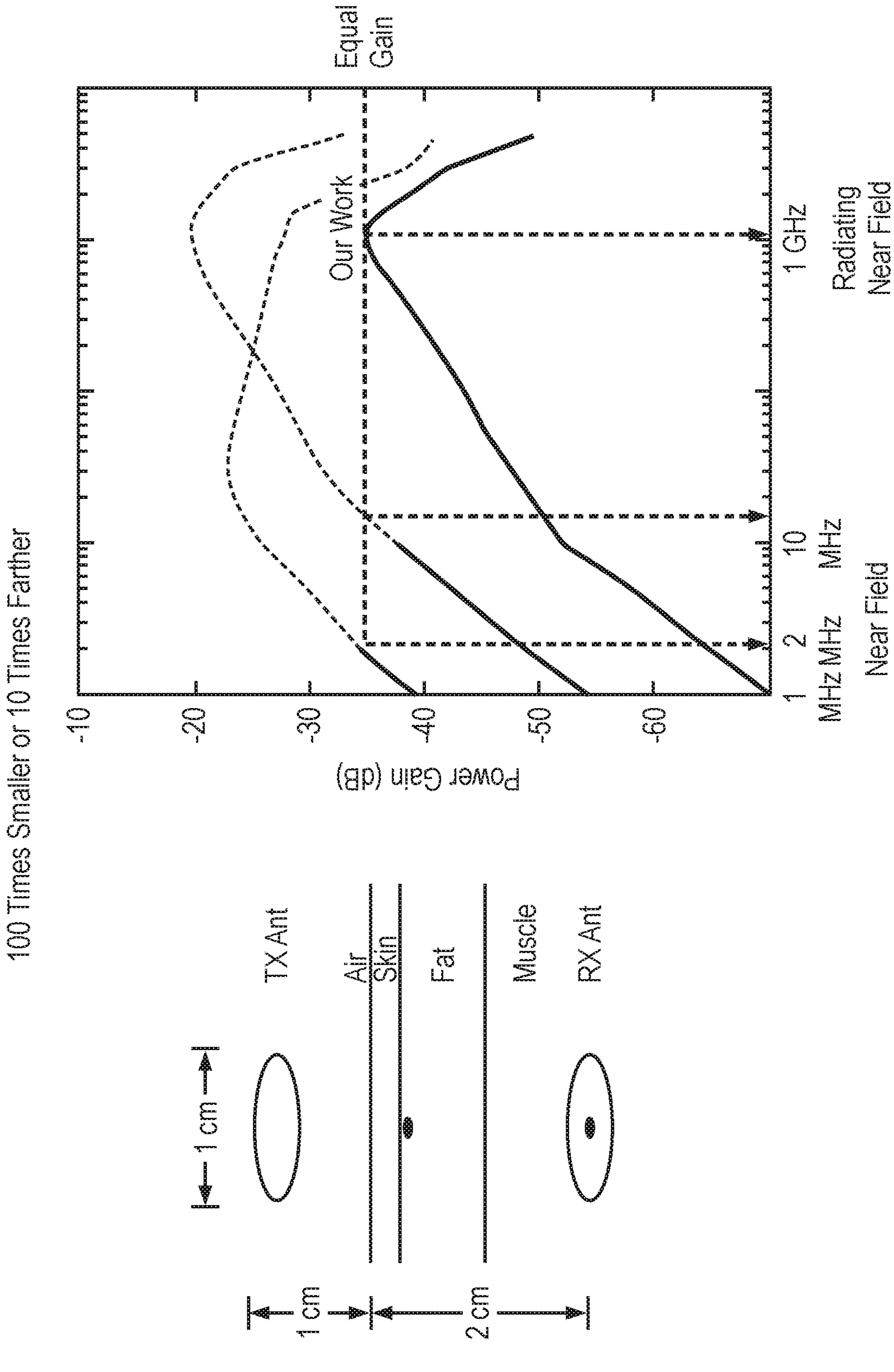
FIG. 13 shows how the present invention can result in a device that is 100 times smaller than conventional devices or one that can transfer 10 times farther.

FIG. 13 shows how the present invention can result in a device that is 100 times smaller than conventional devices or one that can transfer 10 times farther.

Figure 14:
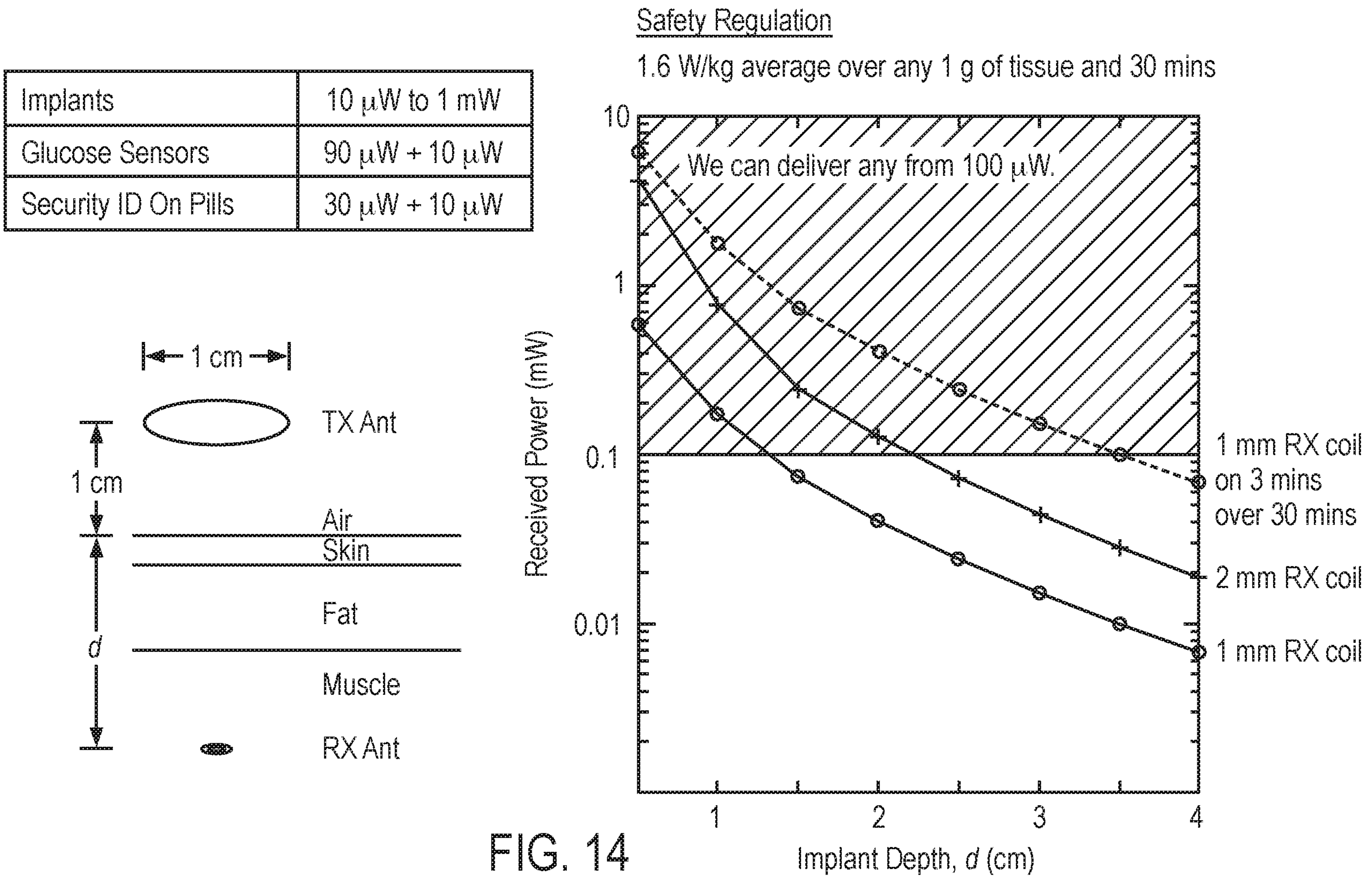
FIG. 14 shows ranges of power that can be transferred according to implant depth.

FIG. 14 shows ranges of power that can be transferred according to implant depth.

FURTHER CONSIDERATIONS—ADAPTIVE MATCHING AND RECTIFICATION

As discussed above a specific use for the wireless power transfer described herein is an implanted neural sensor whose clinical requirements constrain the implanted receiver size to 2 mm×2 mm and specify an implant depth of 15 mm. Ranges in the size of the receive antenna within this device are thus less than 2 mm×2 mm. It is noted, however, that while the apparatus and techniques herein are most useful when the size of one or both antennae is less than or equal to about 10 times the distance between the antennae, that other applications may well exist.

The wireless power link described herein achieves equivalent link gain as conventional inductively coupled links but uses a 100 times smaller receive antennae, enabling mm-sized implanted devices. This development requires three steps: first, determine the optimal frequency for wireless power transfer through tissue to area constrained receive antennae. Second, recognize that to achieve the theoretical maximum gain we must employ a simultaneous conjugate match and make that match robust to inevitable range and dielectric variations associated with a medical implant. And third, develop a highly efficient low voltage rectifier. Each of these are discussed hereinafter

IV. OPTIMAL FREQUENCY

A. Optimality Criteria

In order to determine the optimal frequency for wireless power transfer through tissue optimality criteria must be chosen. There are two potential candidates: for a given power delivered to the implanted device are we most concerned with minimizing losses in the tissue or with minimizing transmit power. This can be expressed quantitatively as: do we seek to maximize (i) link efficiency, $\eta_{link}$, given by the ratio of average power received by the load, $P_{rec}$, to average power loss in the tissue, $P_{tissue,loss}$, or (ii) link gain, $G_{link}$, given by the ratio of average power received by the load, $P_{rec}$, to average power input to the transmitter, $P_{in}$.

$$\eta_{link} := \frac{P_{rec}}{P_{tissue,loss}} \tag{1}$$

$$G_{link} := \frac{P_{rec}}{P_{in}} \tag{2}$$

Minimizing tissue losses and thus tissue heating is a critical specification whereas complexity and power consumption at the transmitter are lower priorities. Therefore we define $f_{opt}$ as the transmission frequency which maximizes $\eta_{link}$. This guides our analytical derivation of $f_{opt}$.

However $\eta_{link}$ is difficult to measure experimentally whilst measurement of $G_{link}$ is straightforward. Fortunately, as will be shown, we can use $G_{link}$, subject to certain constraints, to demonstrate $f_{opt}$ experimentally.

B. Analytical Solution

Tissue permittivity is a complex function of frequency and can be expressed using the debye relaxation model, shown in Eq. (3), where $\tau$ is the dielectric relaxation constant, $\varepsilon_{r0}$ is the relative permittivity at frequencies $\omega<<1/\tau$, $\varepsilon\infty$ is the relative permittivity at $\omega<<1/\tau$, $\varepsilon\infty$, and $\sigma$ is the dc conductivity.

$$\epsilon_r(\omega) = \epsilon_\infty + \frac{\epsilon_{r0} - \epsilon_\infty}{1 - i\omega\tau} + i\frac{\sigma}{\omega\epsilon_0} \tag{3}$$

The imaginary component of $\varepsilon_r(\omega)$ includes the static conductivity $\sigma$ and so dielectric loss in this model includes both relaxation loss and induced-current loss. The model is valid from the frequency at which $\varepsilon_{r0}$ is measured to frequencies much less than $1/\tau$. For example, the parameters for muscle tissue are: $\tau$=7.23 ps, $\varepsilon\infty$=4, and $\varepsilon_{r0}$=54 and the model is valid for frequencies f such that 2.8 MHz<<f>>140 GHz.

Including this model for permittivity in the full-wave electromagnetic analysis of the link we can derive the link efficiency and link gain as a function of frequency. The maximum efficiency for wireless power transmission from a transmitter, modeled by a magnetic current density, in free space to an area constrained receiver, modeled by a magnetic dipole of area $A_r$, in tissue dielectric and loaded by impedance $Z_L$ is given approximately in Eq. (4).

$$\eta_{link} \approx \frac{3k_{I0}\epsilon^{-2k_{I0}d}A_r^2 \text{ real}\left(\frac{1}{Z_L}\right)}{2\pi\sigma d^4}\left[\left(\frac{d^2\epsilon_{r0}}{c^2} + \frac{d\tau(\epsilon_{r0}-\epsilon_\infty)}{c\sqrt{\epsilon_{r0}}}\right)(|\beta_{-1}|^2 + |\beta_1|^2)\omega^2 + 4|\beta_0|^2 - |\beta_{-1}|^2 - |\beta_1|^2 + 2k_{I0}d(|\beta_{-1}|^2 + |\beta_1|^2)\right] e^{-\frac{d\tau(\epsilon_{ro}-\epsilon_\infty)}{c\sqrt{\epsilon_{ro}}}\omega^2} \text{ where } k_{I0} = \frac{\sigma}{2}\sqrt{\frac{\mu 0}{\epsilon 0\epsilon_{ro}}}, \tag{4}$$

d is implant depth, the center of the receiver is on the axis normal to the transit current density plane and $\beta_{-1}$, $\beta_0$ and $\beta_1$ are the components of the unit vector describing the orientation of the receiver relative to the axis of the transmitter. The maximum efficiency is achieved at frequency $$\omega_{opt}^2 = \frac{c\sqrt{\epsilon_{r0}}}{d\tau(\epsilon_{r0}-\epsilon_\infty)} - \frac{4|\beta_0|^2 - |\beta_{-1}|^2 - |\beta_1|^2 + 2k_{I0}d(|\beta_{-1}|^2 + |\beta_1|^2)}{\left(\frac{d^2\epsilon_{ro}}{c^2} + \frac{d\tau(\epsilon_{r0}-\epsilon_\infty)}{c\sqrt{\epsilon_{ro}}}\right)(|\beta_{-1}|^2 + |\beta_1|^2)} \tag{5}$$

In general, $$\frac{d^2\epsilon_{r0}}{c^2} >> \frac{d\tau(\epsilon_{ro}-\epsilon_\infty)}{c\sqrt{\epsilon_{ro}}}.$$

Therefore, we have $$w_{opt} \approx \sqrt{\frac{c\sqrt{\epsilon_{ro}}}{d\tau(\epsilon_{ro}-\epsilon_\infty)}} \tag{6}$$

The optimal frequency is approximately inversely proportional to the square root of implant depth and to the dielectric relaxation constant.

The dielectric properties of many biological tissues types have been characterized by others, as shown in the Table below. The parameters for the 4-term Cole-Cole model which is a variant of the Debye relaxation model. Conversion to the Debye relaxation model is as follows:

$$\tau = \tau_1,\ \epsilon_{r0} = (\epsilon_{r0}-\epsilon_\infty)_1 + \epsilon_\infty, \text{ and } \sigma = \sum_{n=2}^{4}\frac{\epsilon_0(\epsilon_{ro}-\epsilon_\infty)_n}{\tau_n} + \sigma_s$$

TENTABLE I

TENAPPROXIMATE OPTIMAL FREQUENCY FOR TEN DIFFERENT TYPES OF BIOLOGICAL TISSUE, ASSUMING d = 1 CM

| Tissue Type | Approximately $f_{opt}$ (GHz) |
|---|---|
| Blood | 3.54 |
| Bone (cancellous) | 3.80 |
| Bone (cortical) | 4.50 |
| Bone (grey matter) | 3.85 |
| Brain (white matter) | 4.23 |
| Fat (infiltrated) | 6.00 |
| Fat (not infiltrated) | 8.64 |
| Muscle | 3.93 |
| Skin (dry) | 4.44 |
| Skin (wet) | 4.01 |
| Tendon | 3.17 |

That data is used to calculate the approximate optimal frequencies for ten different kinds of tissue assuming d=1 cm, as listed in Table I. All approximate optimal frequencies are in the GHz-range. The optimal frequency decreases as the transmit-receive separation increases but remains above 1 GHz even up to d=10 cm. This suggests that for any potential depth of implant inside the body, the asymptotic optimal frequency is around the GHz-range for small transmit and small receive sources.

C. Empirical Validation $\eta$link is difficult to measure experimentally whilst measurement of Glink is straightforward. Here it is shown that the maxima of $\eta$link and Glink occur at the same frequency for small antenna sizes although they diverge significantly as antenna size increases. Therefore the optimal frequency can be validated experimentally for small antennae by measuring Glink versus frequency.

Energy conservation says that average power into the transmit antenna is equal to average power out of the receive antenna plus the average power dissipated in the link as expressed in Eq. (7).

$$P_{in} = P_{rec} + P_{loss,total} \tag{7}$$

where total power dissipation in the link, $P_{loss,total}$, takes three forms: resistive losses in the antennae, $P_{wire,loss}$; loss in the tissue, $P_{tissue,loss}$; and radiation loss, $P_{rad,loss}$.

$$P_{loss,total} = P_{tissue,loss} + P_{rad,loss} + P_{wire,loss} \tag{8}$$

Dividing across Eq. (7) by $P_{rec}$ gives $$\frac{1}{G_{link}} = 1 + \frac{P_{loss,total}}{P_{rec}} \tag{9}$$

A wavelength in a lossy dielectric medium is given by $$\lambda = \frac{2\pi}{\mathrm{Im}(\gamma)} \tag{10}$$

where $\gamma$ is the propagation constant given by $$\gamma = \sqrt{j\omega\mu(\sigma + j\omega\epsilon)} = \omega\sqrt{-\mu\epsilon_{eff}} \tag{11}$$

and effective permittivity, $$\epsilon_{eff} = \epsilon - j\frac{\sigma}{\omega}.$$

The permittivity of muscle at 1 GHz is given by $\epsilon_{eff}=(54.811-17.582j)\,\epsilon_0$ and so $\lambda_{muscle,1GHz}=4$ cm. For electrically small, i.e. circumference $\leq\lambda/5$, square loop antennae the radiated power can be modelled by a resistance $R_{rad}$ in series with the antenna:

$$R_{rad} = \frac{4}{3}Re\left(\sqrt{\frac{\mu}{\epsilon_{eff}}}\right)\pi^3\left(\frac{NA}{\lambda^2}\right)^2 \tag{12}$$

where N is the number of turns in the loop and A is the area of the loop. For the experiment 2 mm×2 mm square loop antennae were used at the transmitter and receiver. The radiation resistance of a 2 mm×2 mm square loop antenna driven at 1 GHz in free space is $R_{rad,free\ space}=30.8\ \mu\Omega$. Whilst the radiation resistance of the same antenna, at the same frequency in muscle dielectric is $R_{rad,\ muscle}=12.5\ m\Omega$. For a 2 mm×2 mm square loop antenna driven at 1 GHz with free space on one side and muscle tissue on the other we expect the radiation resistance to be between these two values, and certainly we can take $R_{rad,\ muscle}=12.5\Omega$ as an upper bound.

The antennae were realized using 200 μm wide 1-oz copper metallization traces on a PCB. 1-oz copper has a thickness of t=1.3 mil=33 μm. The conductivity of copper is $\sigma_{Cu}=60\times10^6\ Sm^{-1}$ so that at 1 GHz the skin depth is $\delta Cu=2$ μm. Thus the metallization thickness is much greater than a skin depth. The current will stay on one face of a planar loop above a lossy dielectric and so the series resistance of the loop is given by $$R_{series\ loop} \approx \frac{1}{\omega\sigma\delta\left(1 - e^{-\frac{t}{\delta}}\right)} \tag{13}$$

The antenna loop and feedlines are 1=2.18 mm long. Thus at 1 GHz the series resistance is $$R_{wire,1\ GHz} = 0.09\ \Omega \tag{14}$$

The link consisting of two 2 mm×2 mm square loop antenna separated by 15 mm of tissue was simulated using a 3D electromagentic solver and the s-parameters of the two-port were found. At the frequency of interest those s-parameters can be transformed to a lumped equivalent circuit, valid only at that frequency, by transforming the 2×2 s-parameter matrix, S, to a 2×2 z-parameter matrix, Z, as in Eq. (15).

$$Z = \begin{bmatrix} Z_{11} & Z_{12} \\ Z_{21} & Z_{22} \end{bmatrix} = Z_0(I - S)^{-1}(I + S) \tag{15}$$

where $Z_0$ is the characteristic impedance assumed in measuring the S-parameters. $Z_{12}=Z_{21}$ and thus the link can be represented using a lumped T-model at each frequency, which will be useful later. The coupling is quite weak, the maximum achievable gain being −41 dB, and so losses due to the transmit loop current are much greater than losses due to the much smaller receive loop current. Losses due to the transmit loop current are given by $$P_{loss,total} \geq |I_{Tx\ Loop}|^2 Re(Z_{11}) \tag{16}$$

Substituting this into Eq. (8) we have $$|I_{Tx\ Loop}|^2 Re(Z_{11}) \leq |I_{Tx\ Loop}|^2 (R_{tissue} + R_{rad} + R_{wire}) \tag{17}$$

$$\Rightarrow R_{tissue} \geq Re(Z_{11}) - (R_{rad} + R_{wire}) \tag{18}$$

Simulation gives $Re(Z_{11})=0.4224\Omega$ and we have $R_{rad}<0.0125\Omega$ and $R_{wire}=0.09\Omega$ so clearly $$R_{tissue} >> R_{rad} + R_{wire} \tag{19}$$

$$\Leftrightarrow \frac{P_{rec}}{P_{loss,total}} \approx \frac{P_{rec}}{P_{tissue,loss}} = \eta\text{link} \tag{20}$$

Substituting Eq. (20) into Eq. (9) gives $$\frac{1}{G_{link}} \approx 1 + \frac{1}{\eta\text{link}} \tag{21}$$

which gives the following correspondences between $G_{link}$ and $\eta_{link}$ $$G_{link} = \frac{\eta\text{link}}{1 + \eta\text{link}} \tag{22a}$$

-continued $$\eta\text{link} = \frac{G_{link}}{1 - G_{link}} \tag{22b}$$

The link is a passive system and so $0<P_{rec}<Pfb$ or equivalently $0<G_{Link}<1$. As can be seen from Eqs. (22) $G_{link}$ is a monotonically increasing function of $\eta_{link}$ for the range $0<G_{link}<1$ and $\eta_{link}$ is a monotonically increasing function of $G_{link}$ for the domain $0<G_{link}<1$. Therefore maximizing $G_{link}$ is equivalent to maximizing $\eta_{link}$ and vice versa. Correspondingly maximum link gain and maximum link efficiency occur at the same transmission frequency for 2 mm×2 mm square loop antennae separated by 15 mm of tissue. For 20 mm×20 mm square loop antennae the radiation loss becomes much more significant and the maximum value of $G_{link}$ occurs at a significantly lower frequency than the maximum value of $\eta_{link}$.

Experiments were run using 15 mm of bovine muscle tissue between the two antennae. Muscle dielectric was also placed behind the RX antenna, which is omitted from the diagram for clarity. The antennae were aligned axially. Nylon braces through on board vias were used to ensure accurate antenna alignment without disturbing the field. If the antennae were fed by SMA-PCB jacks close to the antennae then the link gain would be dominated by coupling between the connectors rather than antennae coupling as the connector size is large relative to the antennae and range. To ensure the measured coupling is that between the antennae only, the antennae are fed using 50 Ω stripline, which provides shielding on both sides of the signal line, and a 320 μm thick dielectric between signal line and each ground plane is used to ensure that separation between signal and ground of the feedline is small compared to the antenna size and range. In order to measure $G_{link}$ directly we would need to simultaneously conjugate match the link to the source and load impedances as will be discussed short. We wish to measure $G_{link}$ over a broad range of frequencies, and it would not be feasible to develop a match for each of these frequency points. Instead the s-parameters of the link were measured using a network analyzer and de-embedded to the plane at the input to the transmit antenna and the plane at the output of the receive antenna. Using these de-embedded s-parameters the maximum achievable gain was calculated according to Eq. (23).

$$G_{ma} = \frac{|S_{21}|}{|S_{12}|}\left(k - \sqrt{k^2 - 1}\right) \tag{23}$$

where the stability factor, k, is defined in terms of the link's s-parameter representation as in Eq. (24).

$$k = \frac{1 - |S_{11}|^2 - |S_{22}|^2 + |D|^2}{2|S_{12}||S_{21}|} \tag{24}$$

and $$D = S_{11}S_{22} - S_{12}S_{21} \tag{25}$$

Usually $|D|<1$ in which case $k>1$ is sufficient to guarantee unconditional stability. The link is purely passive and thus unconditionally stable.

Figure 15:
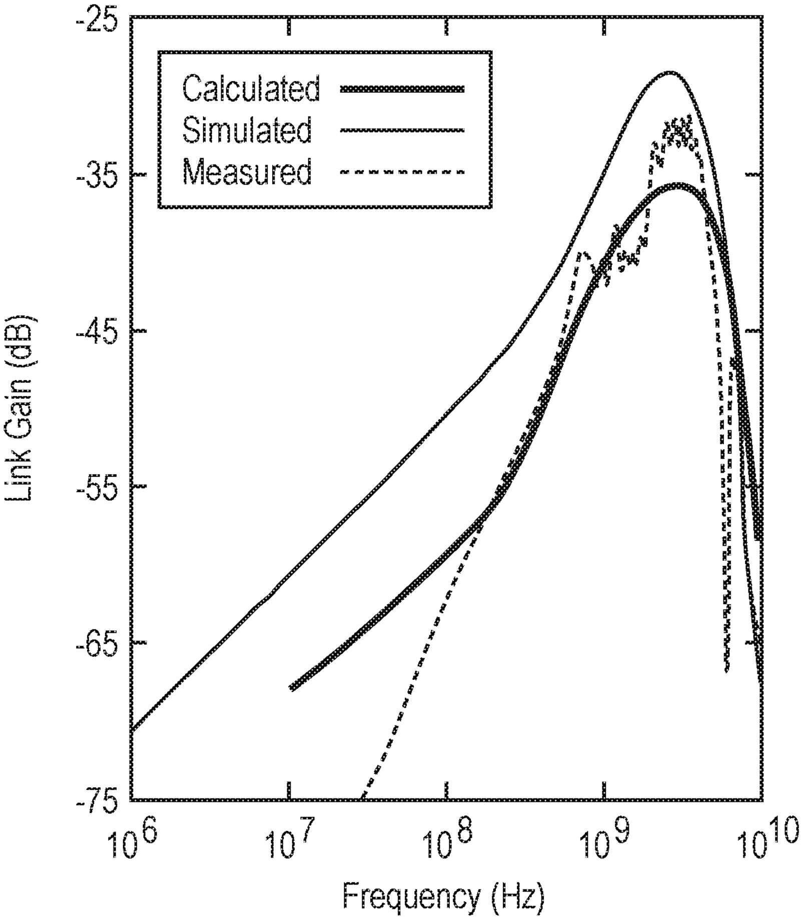
FIG. 15 shows different gain versus frequency plots.

The gain was also simulated using both finite element and method of moments based 3D electromagnetic solvers. It was found that the method of moments based solver, Agilent's Momentum in full wave mode, gave the fastest convergence and results which most closely matched experiment for the antenna sizes and range of interest. The measured, simulated and calculated link gains are plotted versus frequency in FIG. 15 for an implant depth of 15 mm, using 2 mm×2 mm loop antennae. Very similar shapes and similar optimum frequency of $f_{opt}$~3 GHz are seen for all three. Beyond this frequency the tissue polarization cannot keep up with the applied electric field. The phase delay between the electric field and the polarization incurs very high energy loss, killing the gain quickly. This plot is for muscle tissue only. When layered media are considered, modeling anatomy by layers of skin, fat, muscle etc., $f_{opt}$ falls due to increased radiation losses caused by greater impedance mismatches between the layers at higher frequency. Since the transmitter size is less constrained the implemented link consists of a 2 cm×2 cm transmit antenna, a 2 mm×2 mm receive antenna. Simulation with these antenna sizes and a layered tissue model give an optimum frequency just below 1 GHz. Therefore the link was designed to operate at 1 GHz and at ISM band frequency 915 MHz.

V. MATCHING TECHNIQUE

A. Field Region

To understand which circuit techniques should be used to interface to the antennae we must first determine the field type. Near field is defined as when the range is much less than a wavelength, $d<<\lambda$. In this case the link is essentially just a transformer. Quasi-static analysis is sufficient and loaded resonant tuning achieves the maximum link gain. The far field is defined as when the range is much greater than a wavelength, $d<<\lambda$. This is the case in most wireless communications links, in which interaction between the antenna is negligible and one matches to the antenna impedance and the impedance of the medium. At 1 GHz a wavelength in tissue, $\lambda_{tissue}$, is about 4 cm depending on the tissue composition. The range in tissue, d=1.5 cm, is of the same order of magnitude as $\lambda_{tissue}$. Therefore neither near field nor far field approximations can be applied. Consequently neither resonant tuning nor matching to the impedance of the antenna and medium achieve maximum link gain. Resonant tuning comes closer and we will compare that to our solution. First we consider the type of resonant tuning to be used.

B. Resonant Tuning

Figure 16:
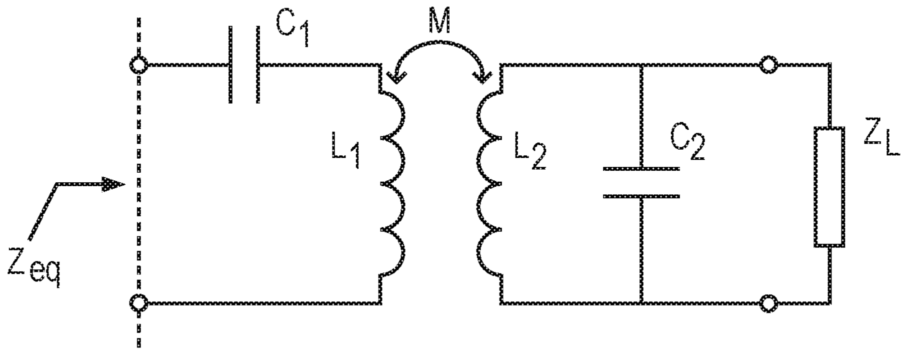
FIG. 16 shows an embodiment of series tuning of the transmitter and shunt tuning of the load.

Many publications have described the use of inductive links to power implanted devices and many different techniques have been proposed for tuning depending on whether the source is a current or voltage source, whether the tuning is in shunt or series and whether loading effects are considered. Others have shown that series tuning of the transmitter and shunt tuning of the load, as illustrated in FIG. 16, is most appropriate when the source is most closely approximated by a voltage source. The two most popular methods of tuning are unloaded tuning and free-running oscillation a.k.a. loaded tuning. For unloaded tuning the tuning capacitances of FIG. 16 are chosen according to $$L_1C_1 = L_2C_2\frac{1}{\omega^2}$$

where $L_1$ and $L_2$ are the inductances of the transmit and receive coils respectively. The requirements for loaded tuning are given by Eq. (26)

$$L_1 C_1 = \frac{1}{\omega^2} \tag{26a}$$

$$X_2 = \omega L_2 - \frac{\omega C_2 R_L^2}{1 + \omega^2 C_2^2 R_L^2} = 0 \tag{26b}$$

where $X_2$ is the reactive part of secondary inductance $L_2$ in series with the parallel combination of $C_2$ and $R_L$. Together Eqs. (26) ensure that the impedance seen looking into the resonant link, $Z_{eq}$ in FIG. 16, is purely real and that the impedance seen looking from the mutual inductance in both directions is purely real, provided the source impedance has no reactive component.

Solving gives the design equations:

$$C_1 = \frac{1}{\omega^2 L_1}$$

for both loaded and unloaded tuning, $$C_2 = \frac{1}{\omega^2 L_1}$$

for unloaded shunt tuning and $$C_2 = \frac{R_L \pm \sqrt{R_L^2 - 4\omega^2 L_2^2}}{2\omega^2 R_L L_2} \tag{27}$$

for loaded tuning where $R_L$ is the load resistance. A solution for $C_2$ in the loaded resonant tuning case exists if and only if $R_L > 2\omega L_2$. The 2 mm×2 mm square loop antenna of the implanted receiver has an inductance of $L_2$=4.64 nH which means that at f=1 GHz a solution exists when $R_L > 58\Omega$. We are interested in much higher load impedances and so a solution will exist. When $R_L >> \omega L_2$, which is true for our link, then Eq. (27) reduces to $$C_2 = \frac{1}{\omega^2 L_1}$$

and so loaded turning and unloaded tuning are equivalent for this link.

C. Simultaneous Conjugate Matching

The link has two ports and is linear. The link is purely passive and thus unconditionally stable. A well-known result in microwave and RF circuits is that, for a given source impedance, simultaneous conjugate matching of a stable linear two-port to the source and load impedances achieves the maximum power gain from the source to the load. The maximum achievable power gain is given in terms of the s-parameters of the link as $G_{ma}$ in Eq. (23), and is independent of the load impedance. This is a standard technique to maximize amplifier power gain, but has not previously been used in wireless power transfer links.

To realize the simultaneous conjugate match we need matching networks which produce reflection coefficients, $\Gamma_{Sm}$ and where D is specified in Eq. (25).

TABLE II

EXISTENCE CONDITIONS FOR L-MATCHES

| Existence Conditions | L-section types |
| --- | --- |
| $R_{s_m} > R_s$, $\lvert X_s \rvert \geq \sqrt{R_s(R_{s_m} - R_s)}$ | Normal and Reversed |
| $R_{s_m} > R_s$, $\lvert X_s \rvert < \sqrt{R_s(R_{s_m} - R_s)}$ | Normal Only |
| $R_{s_m} < R_s$, $\lvert X_{s_m} \rvert \geq \sqrt{R_{s_m}(R_s - R_{s_m})}$ | Normal and Reversed |
| $R_{s_m} < R_s$, $\lvert X_{s_m} \rvert < \sqrt{R_{s_m}(R_s - R_{s_m})}$ | Reversed Only |

Figure 17:
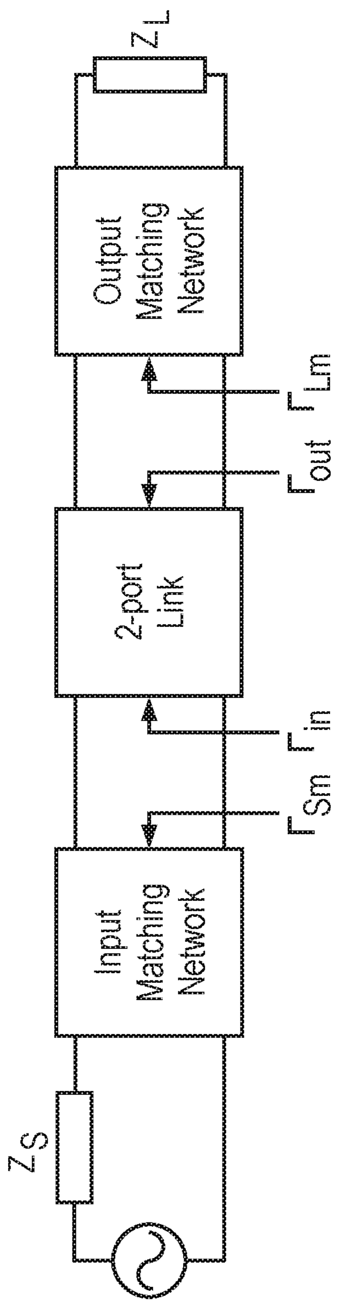
FIG. 17 illustrates a matching network according to an embodiment.

$\Gamma_{Lm}$, as specified in Eq. (28) and Eq. (29)

$$\Gamma_{Lm} = \frac{C_2^\dagger}{|C_2|}\left[\frac{B_2}{2|C_2|} - \sqrt{\frac{B_2^2}{|2C_2|^2} - 1}\right] \tag{29}$$

$$B_1 = 1 - |S_{22}|^2 + |S_{11}|^2 - |D|^2 \tag{30}$$

$$C_1 = S_{11} - DS_{22}^\dagger \tag{31}$$

$$B_2 = 1 - |S_{11}|^2 + |S_{22}|^2 - |D|^2 \tag{32}$$

$$C_2 = S_{22} - DS_{11}^\dagger \tag{33}$$

and where D is specified in Eq. 25. It is noted that the $\Gamma_{Lm}$ as specified in Equations 28 and 29 is also illustrated in FIG. 17.

The power link is a narrowband system and so two-element L-matching sections are sufficient. Calculation of the component values for a lumped L-match is straight forward and described in texts. A brief outline of these calculations is given here for the source match, transforming $Z_S$ to $Z_{S_m}$. The load match, transforming $Z_L$ to $ZL_m$, can be calculated similarly. First we convert the required refection coefficient to an impedance $$Z_{S_m} = R_{S_m} + jX_{S_m} = Z_0\left(\frac{1 + \Gamma_{S_m}}{1 - \Gamma_{S_m}}\right) \tag{34}$$

where $Z_0$ is the reference impedance used in measuring the S-parameters.

Figure 18:
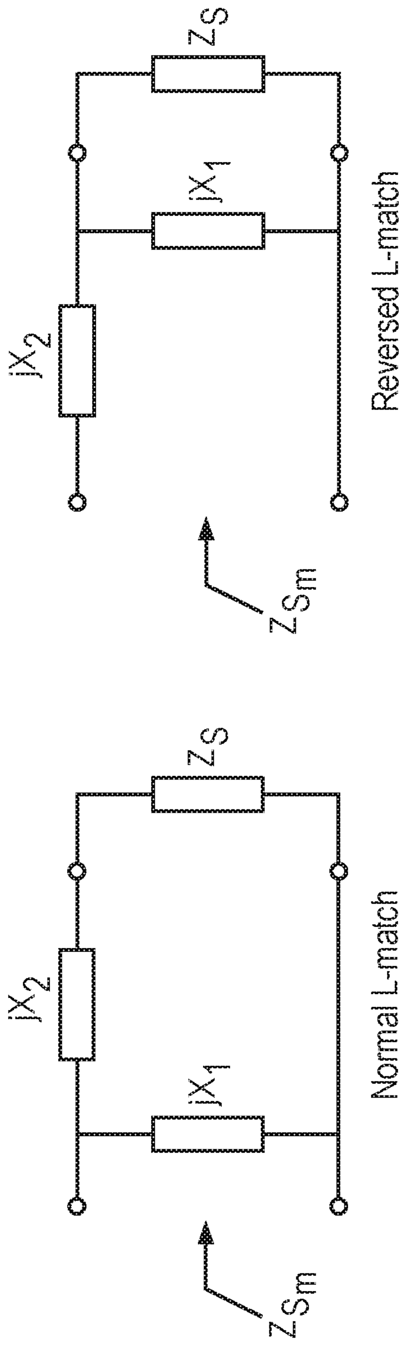
FIG. 18 shows Normal type L-match component reactances and reversed type L-match component reactances.

There are two types of L-match which can be used to transform an impedance $Z_S$ to another $Z_{S_m}$ as illustrated in FIG. 12. Which type of L-match exists is determined using Table II, in which $ZS = R_S + jX_S$ and $Z_{S_m} = R_{S_m} + jX_{S_m}$. Normal type L-match component reactances are given by Eq. 35 and reversed type L-match component reactances by Eq. 36 according to the naming convention illustrated in FIG. 18.

$$X_1 = \frac{-X_{S_m} \pm R_{S_m} Q}{\frac{R_{S_m}}{R_S} - 1} \tag{35a}$$

$$X_2 = -(X_S \pm R_S Q) \tag{35b}$$

$$Q = \sqrt{\frac{R_{S_m}}{R_S} + \frac{X_{S_m}^2}{R_{S_m} R_S} - 1} \tag{35c}$$

$$X_1 = \frac{-X_S \pm R_S Q}{\frac{R_S}{R_{S_m}} - 1} \tag{36a}$$

-continued $$X_2 = -(X_{S_M} \pm R_{S_m} Q) \tag{36b}$$

$$Q = \sqrt{\frac{R_S}{R_{S_m}} + \frac{X_S^2}{R_{S_m} R_S} - 1} \tag{36c}$$

D. Comparison of Resonant Tuning and Simultaneous Conjugate Matching

Link gains under both resonant tuning and simultaneous conjugate matching are compared for two links. Link 1, is the link we used to verify the optimal frequency and consists of 2 mm×2 mm square loop antennae at both the transmit and receive sides with the transmitter placed 1 mm above the tissue and the receiver placed 15 mm deep into the tissue with source and load impedances of 50Ω. Link 2 is the implemented system. The transmit antenna size is less constrained as it is outside the body so we use a 2 cm×2 cm square loop transmit antenna and a 2 cm×2 cm square loop receive antenna placed 15 mm deep into the tissue. The transmit loop is placed 1 cm above the tissue to allow practical packaging thickness and to ensure that SAR regulations are met. The source impedance is 50 Ω and load impedance is 13.9 kΩ||28.7 fF which represents the loaded rectifier as will be explained later. In both cases the antennae are axially aligned and their axis is perpendicular to the tissue surface.

1) Link 1: The inductance of the antenna and its feed-lines was estimated using Agilent ADS Momentum giving L=4.64 nH for the 2 mm×2 mm loop and so $$C_1 = C_2 = \frac{1}{\omega^2 \times 4.64 \text{ nH}} = 5.46 \text{ pF}$$

are required at 1 GHz. Simulation of the resonant tuned link gives $G_{Link\ 1}$=−52.2 dB.

The s-parameters of the simulated link 20 mm×20 mm 20 mm Tx and 2 mm×2 mm Rx separated by 1 mm of free space and 15 mm of tissue were calculated using also Momentum.

$$S = \begin{bmatrix} -0.494 + j0.855 & (1.577 + j1.454) \times 10^{-4} \\ (1.577 + j1.454) \times 10^{-4} & -0.490 + j0.855 \end{bmatrix} \tag{37}$$

These s-parameters were used to calculate the simultaneous conjugate match. A lumped T-network was calculated by transforming the s-parameters to impedance parameters using Eq. (15). Circuit simulation of this link model and simultaneous conjugate match gives $G_{Link\ 1}$=41.9 dB.

IIIANDTABLE

| IIIANDCOMPARISON OF LINK GAINS UNDER RESONANT TUNING IIIANDSIMULTANEOUS CONJUGATE MATCHING | Link 1 | Link 2 |
|---|---|---|
| Gain with Resonant Tuning (dB) | −52.2 | −46.3 |
| Gain with Sim Conj Match (dB) | −41.9 | −32.5 |

2) Link 2: Momentum gives an inductance of L=47.6 nH for the 20 mm×20 mm loop. Our load is 13.9 kΩ||28.7 fF at 1 GHz, so for resonant tuning we assume $Z_L$=13.9 kΩ and subtract 28.7 fF from the calculated value for $C_2$. For 20 mm×20 mm Tx and 2 mm×2 mm Rx we calculate $$C_1 = \frac{1}{\omega^2 \times 47.6 \text{ nH}} = 0.532 \text{ pF and } C_2 = \frac{1}{\omega^2 \times 4.64 \text{ nH}} = 0.546 \text{ pF at 1 GHz.}$$

Simulation of the resonant tuned link gives $G_{Link\ 2}$=−46.3 dB.

The s-parameters of the simulated link (2 cm tx, 10 mm free space, 15 mm tissue, 2 mm rx) are:

$$S = \begin{bmatrix} 0.9610 + j0.2384 & (0.6169 - j7.124) \times 10^{-4} \\ (0.6169 - j7.124) \times 10^{-4} & -0.4374 + j0.8726 \end{bmatrix} \tag{38}$$

Figure 19:
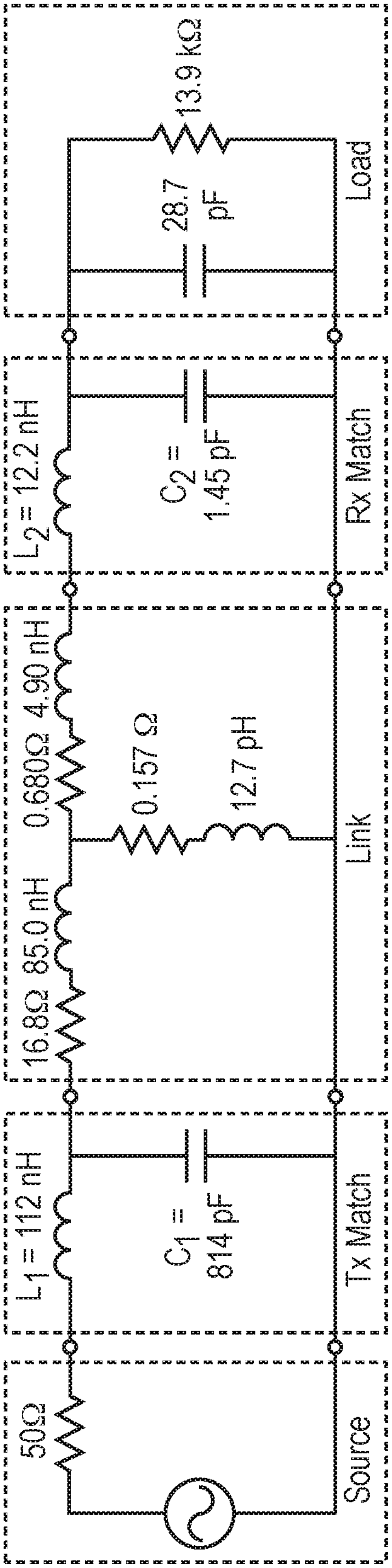
FIG. 19 illustrates an embodiment of the link model and simultaneous conjugate matches.

Again we can transform these s-parameters to a lumped T-model valid at that frequency. The link model and simultaneous conjugate matches are illustrated in FIG. 19. Simulation of the link with simultaneous conjugate matching $G_{Link\ 2}$=−32.5 dB.

For both links simultaneous conjugate matching results in more than 10 dB higher link gain than resonant tuning as summarized in Table III.

E. Match Sensitivity

The simultaneously conjugate matched link will allow maximum power transfer from the source to the load provided the link is modeled correctly and the match component values are accurate. However link parameters cannot be known accurately prior to deployment due to variation in implant depth; misalignment between antennae; and variation in tissue composition between subjects (e.g. different fat/muscle ratios). Hence the required match components cannot be known exactly.

Figure 20:
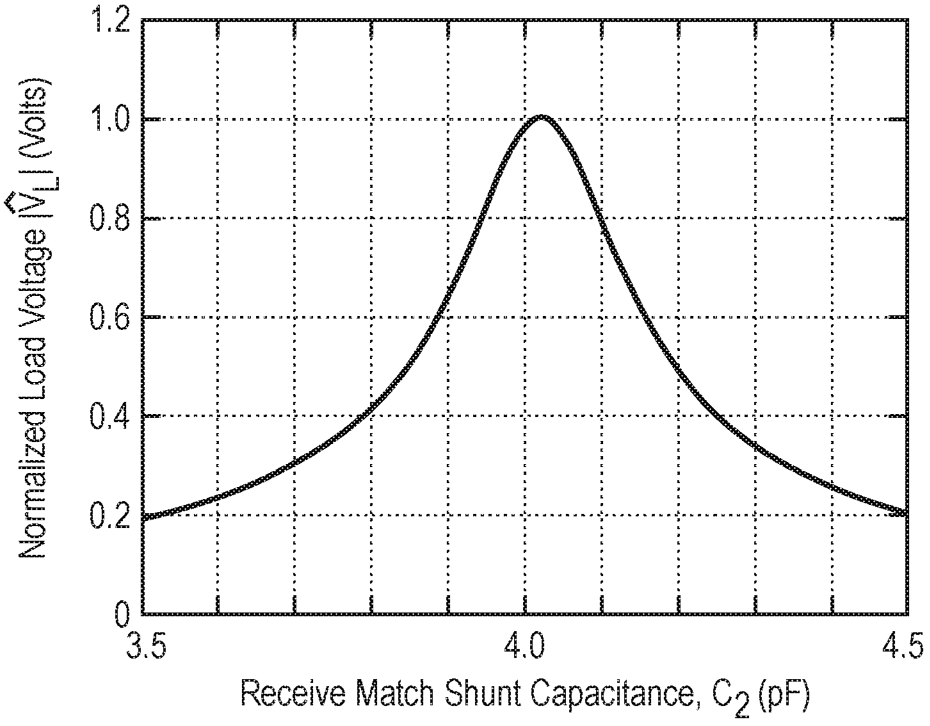
FIGS. 20 and 21 show graphs of receive match shunt capacitance to normalized load voltage and gradient of load voltage, respectively.

To analyse the sensitivity of link gain to placement accuracy and tissue thickness we consider a ±1 mm placement inaccuracy. The s-parameters of the link with 15 mm implant depth and perfect alignment between the Tx and Rx antenna were measured and the receive side match components were calculated as a series inductance L2=1.05 nH and a shunt capacitance $C_2$=4.02 pF. The measured s-parameters were transformed to a lumped T-model which was simulated with the calculated match component values. The simulated link gain equalled the theoretical maximum achievable gain for the ideal link $G_{ma,Link_{ideal}}$=28.4 dB. The s-parameters of a second link wherein the implant depth is increased by 1 mm and the antennae are misaligned by 1 mm were measured. The receive side matching components were calculated as $L_2$=1.55 nH and $C_2$=4.08 pF. Simulation of this link with its match component values shows that link gain equals the maximum achievable gain $G_{ma,Link_{actual}}$=28.6 dB. However if the match components for the ideally aligned link were used with this marginally misaligned link, the link gain would be −31.8 dB, a decrease of 3.2 dB for only ±1 mm placement inaccuracy. More generally, FIG. 20 shows the variation of $|V_L|$ the normalized magnitude of the voltage across the load, with the receive match shunt capacitance, $C_2$. It can be seen $|V_L|$ has a maximum at the design value of $C_2$=4.02 pF and falls off sharply as $C_2$ varies. In fact if $C_2$ is only 2.5% different from the design value, i.e. $C_2$=3.91 pF, $|V_L|$ falls by 66%. Therefore it is critical that a precise $C_2$ be used.

F. Adaptive Matching

Since the precise match component values cannot be known at the design phase and the link gain is so sensitive to those parameters it is needed to autonomously adapt the match to compensate for tissue and placement variations and thus ensure maximum power transfer to the load.

If the performance surface is parabolic or similar to parabolic in the region of interest then gradient search can be used. FIG. 20 traces a curve which is almost parabolic in shape, particularly near the maximum. Gradient search techniques use iteration steps proportional to $\nabla_k$ as in Eq. (39).

$$C_{2_{k+1}} = C_{2_k} + \mu\nabla k \tag{39}$$

Where μ is a constant, a design parameter $$\nabla_k = \left.\frac{\partial |V_L|}{\partial C_2}\right|_{C_2=C_{2_k}} \tag{40}$$

Figure 21:
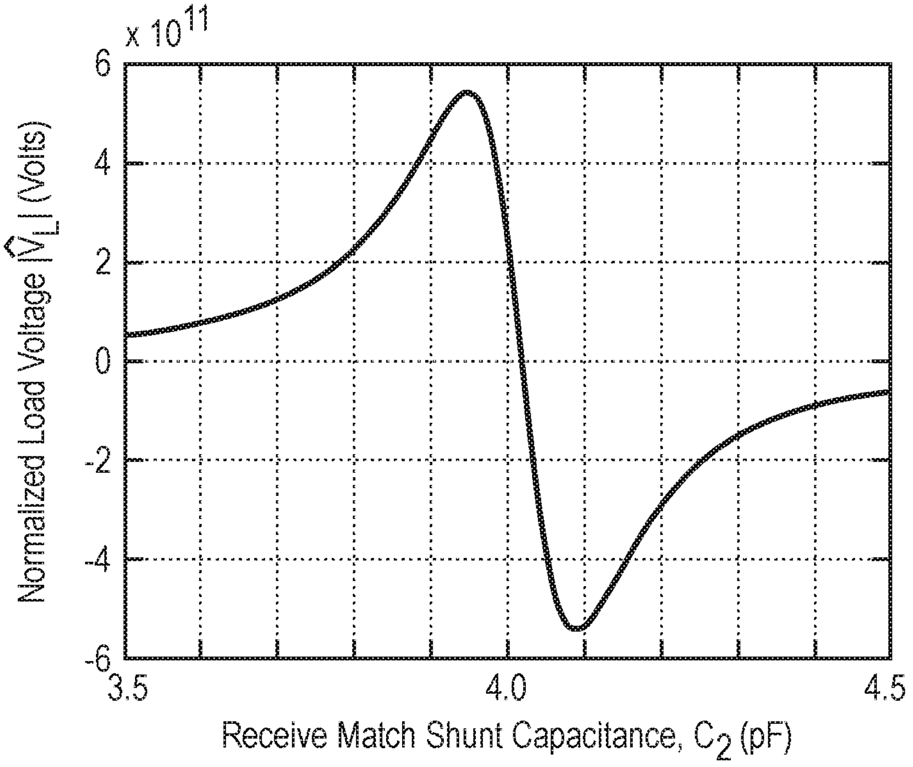

FIG. 21 however shows that $\nabla_k$ is not linear in C2, so $|V_L|$ is not a parabolic function of $C_2$. In fact $\nabla_k$ becomes very large near the optimum point and quickly transitions through zero at the optimum point so the popular stochastic gradient descent algorithm LMS would not be a stable. FIG. 21 does show that $|V_L|$ is a monotonically increasing function of $C_2$ for $C_2<C_{2,opt}$ and a monotonically decreasing function of $C_2$ for $C_2>C_{2,opt}$. If fixed step size iterations are used and the direction of iteration is chosen by the sign of $\nabla_k$ as illustrated in Eq. (41) then the output will tend to the desired value.

$$C_{2_{k+1}} = C_{2_k} + \mu.\operatorname{sgn}(\nabla_k) \tag{41}$$

The drawback of fixed step size adaptation is the difficulty in choosing an appropriate step size to achieve a satisfactory tradeoff between speed of convergence and accuracy. An improvement which will be readily applicable in the implementation is to use a hybrid of binary search and gradient search. The idea being to start with some maximum step size and iterate C2 by adding the step size to $C_2$ if $\nabla_k>0$ or subtracting the step size from $C_2$ if $\nabla_k<0$ at each iteration. When $\nabla_k$ changes sign the step size should be halved. This is the match adaptation algorithm we use and is summarized below.

$$\begin{aligned} &\text{if} && \operatorname{sgn}(\nabla_k) = \operatorname{sgn}(\nabla_k) \\ &\text{then} && \mu_k = \mu_{k-1} \\ &\text{else if} && \operatorname{sgn}(\nabla_k) \neq \operatorname{sgn}(\nabla_k) \\ &\text{then} && \mu_k = \frac{\mu_{k-1}}{2} \\ &\text{end} && \\ &C_{2_{k+1}} = C_{2_k} + \mu_k \cdot \operatorname{sgn}(\nabla_k) \end{aligned} \tag{42}$$

The algorithm depends only on the sign of the gradient, not on the value of the gradient itself. Therefore there is no need to calculate the gradient value, calculating just the sign is easier and will save power and area.

Figure 22:
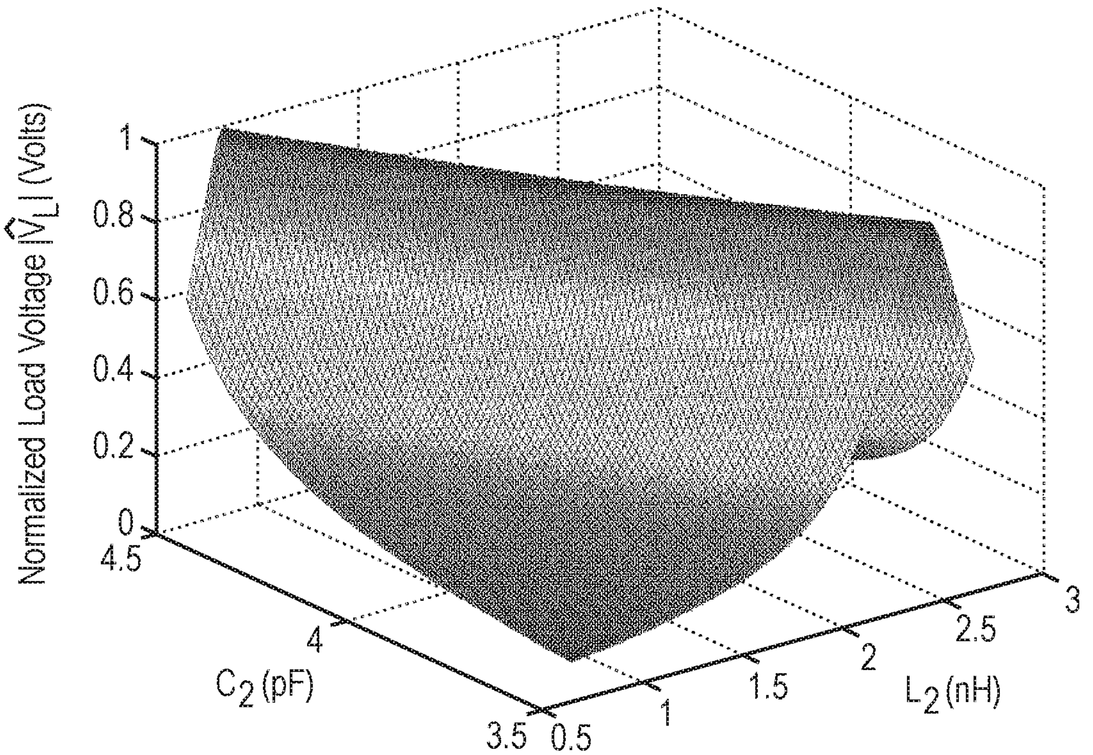
FIG. 22 shows a surface-plot of |VL| versus (L2, C2)

A surface-plot of |VL| versus (L2, C2) as shown in FIG. 22, the series inductance and shunt capacitance of the receive match, shows that there is only one degree of freedom. That is for a fixed value of one component in the match the other component can be varied to achieve the maximum |VL| and thus maximum power transfer. The transmit and receive matches are to first order independent and can be tuned separately. A similar argument as applied to the receive match can be applied to the transmit-side match. Therefore the complete link matching has two degrees of freedom which may be treated as independent, one in the transmit match and one in the receive match.

G. Tunable Match Implementation

It is easier to tune shunt capacitors than series inductors for a number of reasons. Firstly shunt elements can be just switched in or out with a single switch at either terminal whereas switching in/out a series element also requires switching out/in a short circuit in its place require more switches and control circuitry and increasing parasitics and area. Secondly switch parasitic capacitances can easily be absorbed in the capacitance of the shunt capacitors but cannot be absorbed by the inductors and thirdly varactors are readily manufacturable in CMOS but variable inductors are not. Primarily because of the first two reasons it was chosen to tune the shunt capacitance. The variable capacitance was realised as binary weighted capacitor array rather than a varactor because the control algorithm is implemented digitally and its output can feed directly to the switches in the binary weighted capacitor array to select the capacitance, if varactors were used a digital-to-analog converter would be needed between the control algorithm circuits and the varactor increasing power dissipation, area and complexity; a binary weighted array of MiM capacitors array displays much superior linearity to a MOS varactor and the frequency of operation is slow enough relative to the pass gate resistance and capacitor array time constant that charging delay is negligible.

Figure 23:
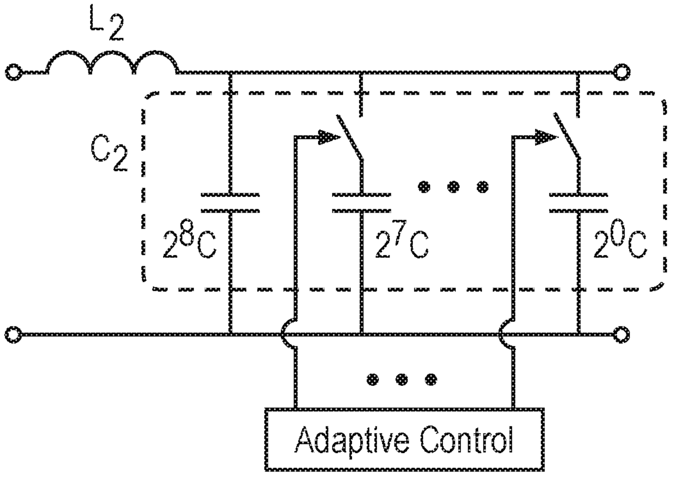
FIG. 23 shows an embodiment of a 9 element binary weighted capacitor array.

For the implementation, one embodiment of a 9 element binary weighted capacitor array was used, as shown in FIG. 23. Each of the capacitors in the array is selectable apart from the 28 C unit capacitance which is permanently connected. At startup all of the switches are open and C2=3.7 pF, ensuring that the 3-stage rectifier output ≥0.7 V for all antennae separation from 7.2 mm to 19.1 mm. This voltage is used as the supply for the array switches. The sign of ∇k is found by switching the smallest capacitance in and out of the array. No addition, multiplication or division operations are required, just a compare operation which simplifies the circuitry required and saves processing power and area. In this embodiment the capacitor array and digital control are implemented on chip but the adaptation algorithm is run off of the receive chip, though in other embodiments it is possible to have the adaptation algorithm on-chip as well. C2 converges to the optimum value.

In the above embodiment, the adaptive matching used feedback from the receive IC to assist in providing the adaptive matching. This feedback is implemented as, in one embodiment, a configuration wherein the receive-side adaptive match circuit receives a particular tuned impedance from a tunable impedance from the transmit-side, and provides a feedback signal to the transmit-side adaptive match circuit, such that the feedback signal provides an indication of a gain of the power signal as received at the wireless power transmitter for a particular tuned impedance, and which the transmit-side adaptive-match circuit can then use to automatically adjust the impedance of the tunable impedance in order to increase a gain of the received power signal by the receiver. That this can be constantly monitored allows, in an environment of unknown transmission characteristics that change over time, sufficient power transfer throughout the period necessary for usage.

While such feedback is preferable, in another embodiment, particularly with the adaptive algorithm off-chip, it is possible to measure gains by incremental changes from the transmit-side, and converge to a preferable match without obtaining feedback from the receive-side.

Even without feedback the simultaneous conjugate matching technique is still useful if the link parameters (antenna alignment, range and inter-antennae medium) can be estimated reasonably accurately.

VI. DC CONVERSION

When the link is simultaneously conjugate matched to the known source and typical load impedances we expect a voltage amplitude of approximately 0.75 V at the output of the match at the receiver for a 250 mW input power at the transmitter, the maximum input as discussed earlier. This 0.75 V 1 GHz signal must be converted to a usable DC to power the implanted IC.

A. Rectifier Design

Figure 24B:
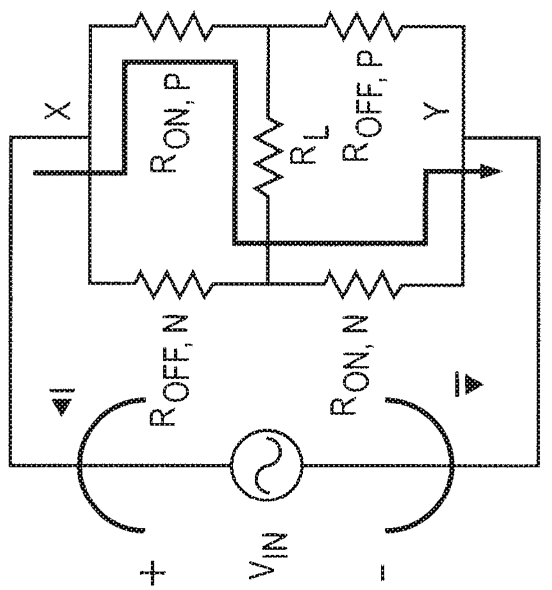
FIGS. 24*a-b* show a synchronous self-driven rectifier and an equivalent model of voltage dependent resistances.
Figure 24A:
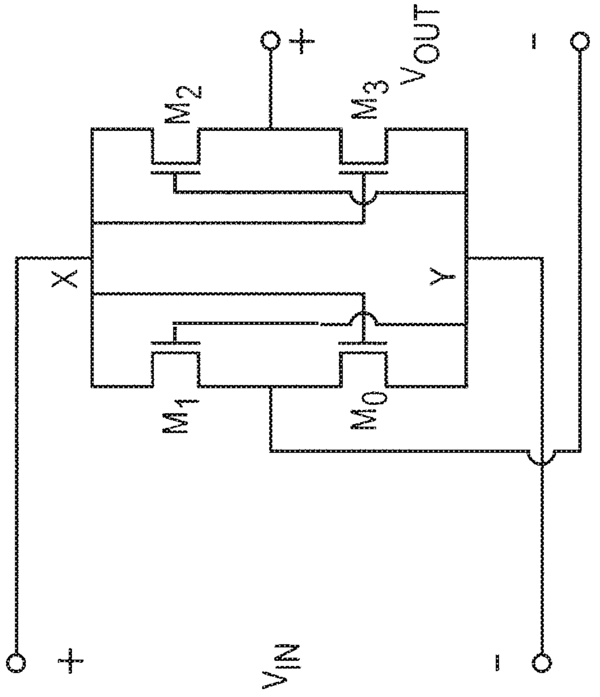

A CMOS rectifier using diode connected MOSFETs with $V_{TH}$=0.4V would generate, after capacitive smoothing, an ideal output voltage $V_{DC}$=0.35V for an input amplitude $V_{IN}$=0.75V, dissipating more than half of the power delivered across the rectification diodes. Instead a synchronous self-driven rectifier is used as shown in FIG. 24(*a*). The basic operation is as follows: in the half cycle when node X is high relative to node Y, $M_0$ and $M_2$ are "on" and $M_1$ and $M_3$ are "off". The applied gate-source voltage may not be enough to turn the devices strongly on or off so the devices can be thought of as voltage dependent resistances as shown in as illustrated in FIG. 24(*b*).

Provided $R_{OFF,N}$, $R_{OFF}$, P>>$R_L$ current will be steered to the load through opposite transistor paths each half-cycle and an ideal rectified voltage of $V_{REC}$=produced, where $R_{ON}=R_{ON,N}+R_{ON,P}$. To first order this design is more efficient than using diode-connected devices for rectification if the ideal voltage drop due to forward conduction loss, $$\frac{R_{ON}}{R_L + R_{ON}} V_{IN},$$

is less than $V_{TH}$.

Figure 25:
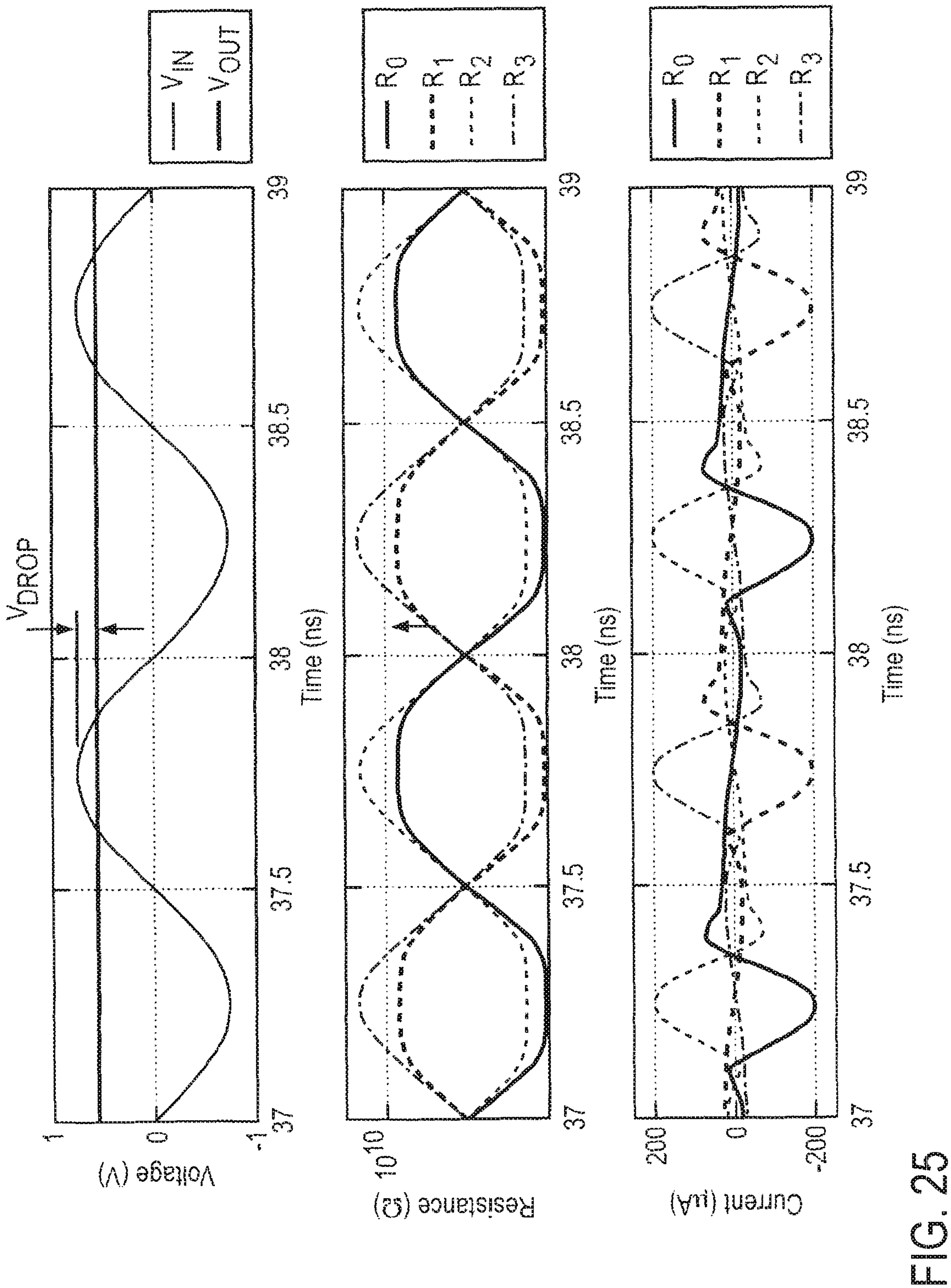
FIG. 25 shows various currents.

The foregoing discussion idealizes the source as a square wave. However the source is sinusoidal resulting in additional loss mechanisms. Since the peak value of $V_{IN}$ is not much greater than $V_{TH}$, the "on" and "off" resistances are relatively similar in magnitude for a significant duration of each cycle as illustrated in the middle panel of FIG. 25. Simulated currents through each of transistors in FIG. 24(*a*) are illustrated in the bottom panel of FIG. 25. The large peaks correspond to current being delivered to the load as intended. In between these large bumps, in the nominally dead zone, as the input voltage falls below the DC output we see significant reverse currents through the "on" devices and the supposedly "off" devices shunt current away from the load.

Figure 26:
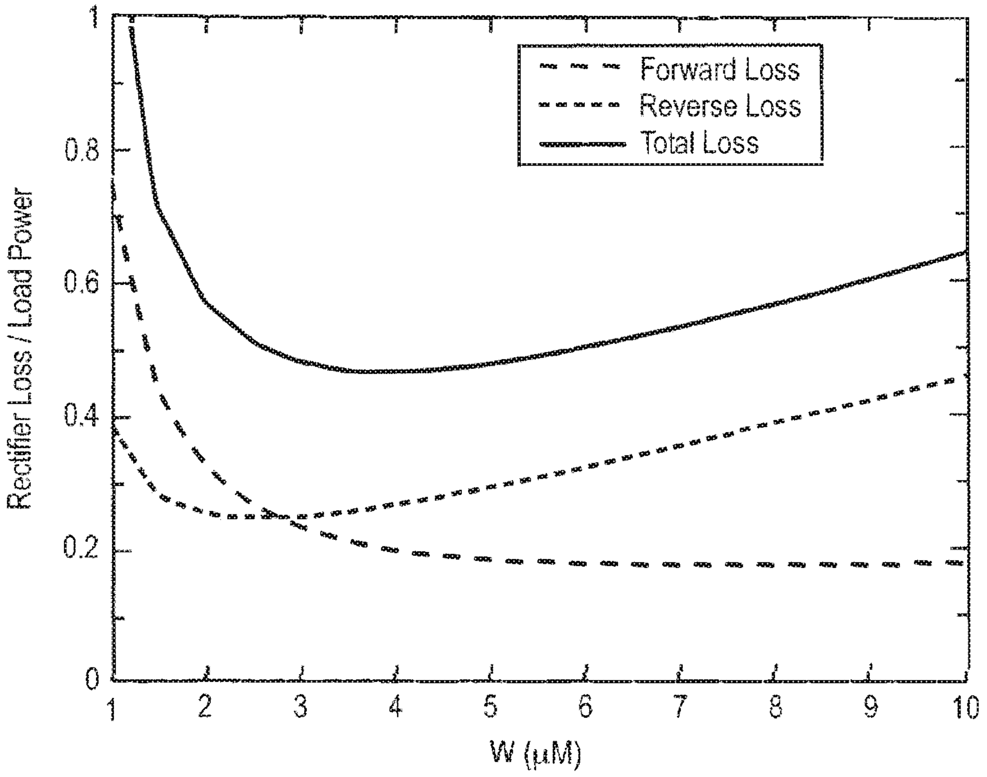
FIG. 26 shows a slice of a curve that represents a ratio of loss in the rectifier to power delivered to the load versus widths of NMOS and PMOS devices.

Design choices affect these losses in order to design the most efficient rectifier. As W/L is increased $R_{OFF}$ and $R_{ON}$ decrease. Decreasing $R_{ON}$ reduces forward conduction loss, but decreasing $R_{OFF}$ increases reverse conduction and "off" state conduction loss. If we combine these two losses and plot the ratio of loss in the rectifier to power delivered to the load versus widths of the NMOS and PMOS devices we see a convex surface plot with a global optimum point. Therefore an optimum set of W/L exists which minimizes total loss. A slice through that curve is shown in FIG. 26 which shows that the optimum PMOS width is 4 μm for minimum length devices. Each rectifier stage, optimally sized, has a $V_{DROP}$=0.15 V for a 0.75 V amplitude input. Three stages are connected in a charge pump configuration to generate a 1.8 V DC output. The pumping capacitance is 1 pF, chosen to equal the output smoothing capacitance. Deep N-well isolation of the rectifier transistors whose bulk terminals are tied to their source terminals ensures that there is no degradation of voltage generated per stage due to body effect.

B. Rectifier Input Impedance

In order to design the match correctly it is important to know the source and load impedances. An off-the-shelf transmit driver is used and the source impedance is 50Ω. The load impedance is the input impedance of the loaded rectifier, $Z_{in,rect}$. Ideally $Z_{in,rect}$ would be independent of the rectifier and equal to the resistance the rectifier must drive, Eq. (43).

$$Z_{in,rect\,ideal} \approx R_L \tag{43}$$

However non-idealities such as the non-zero impedance of the rectifier itself, parasitic capacitances within the rectifier and finite smoothing capacitance at the rectifier output take on greater significance in this low-voltage, high-frequency design and considerably impact rectifier input impedance.

Figure 27:
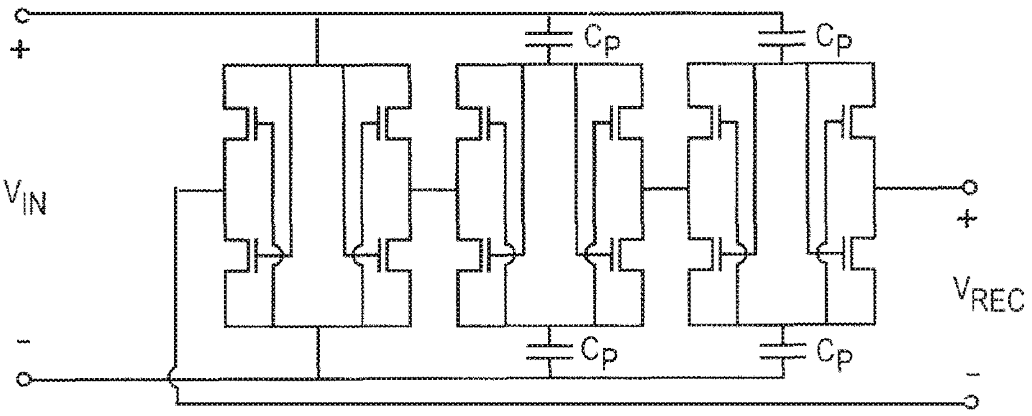
FIG. 27 shows an embodiment of a synchronous self-driven rectifier with pump capacitances.

The pump capacitances, $C_P$ in FIG. 27, present impedances of j159 Ω at the signal frequency, much smaller than both the on-resistance of the current steering rectifier cell and the load resistance and so can be approximated by short circuits. FIG. 27 shows that each transistor's gate connects to one input line and the transistor's source connects to the other input line. So each transistor adds a gate-source capacitance, $C_{gs}$, across the input terminals. In each rectifier cell, one NMOS and one PMOS are ON and one NMOS and one PMOS are OFF at any given time. $C_{gs}$ of the OFF devices is negligible. The ON transistors are in the triode region and so the $C_{gs}$,ON is approximately half of the gate-to-channel capacitance, $C_{gs}$. For the device sizes chosen each stage contributes $C_{gs,ON,NMOS}+C_{gs,ON,PMOS}=\frac{1}{2}(C_{gc,N}+C_{gc,P})\approx 8$ fF across the input terminals, totaling N/2 $(C_{gc,N}+C_{gc,P})$ where N=3 is the number of rectifier stages. In series with the load resistance we must place the on-resistance of each cell to account for conductive losses, N $(R_{on,N}+R_{on,P})$. Ideally the output smoothing capacitance, in parallel with the resistive load, would be infinite giving a purely dc output and hence the output smoothing capacitance would be irrelevant to the input impedance.

Figure 28:
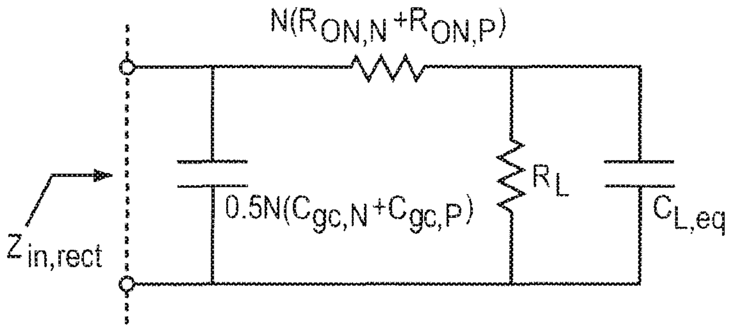
FIG. 28 shows an input impedance model.

However the presence of output voltage ripple means that there is the loading is not purely resistive. This is a non-linear effect and the ripple frequency is twice that of the input frequency but we can crudely model it by considering the total charging and discharging at that node per input period. For a ripple peak-to-peak voltage of $V_{ripple}$ then the output capacitance charges up and discharges by $C_{smooth}$ $V_{ripple}$ twice each input period corresponding to an aggregate charge change of $\Delta Q=2C_{smooth}\ V_{ripple}$ each input period. We want to model the shunting of current parallel to the load resistance and so this charging and discharging is modeled by a capacitance $C_{L,eq}=\Delta Q/\Delta V$ where $\Delta V=V_L=0.6V$ is the voltage across $R_L$. Therefore for ripple $V_{ripple}=2$ mV with a smoothing capacitance of $C_{smooth}=1$ pF, $C_{L,eq}$==6.7 fF. The input impedance can then be modeled as shown in FIG. 28 giving a second approximation to $Z_{in,rect}$ of $$Z_{in,rect} \approx \frac{1}{j\omega\frac{N}{2}(C_{gc,N}+C_{gc,P})} \Bigg\| \left[N(R_{on,N}+R_{on,P}) + \left(R_L \Bigg\| \frac{1}{j\omega\frac{2V_{ripple}}{V_L}C_{smooth}}\right)\right] \tag{44}$$

At 1 GHz Eq. (44) gives $Z_{in,rect}$=1917 j47955Ω which is equivalent to a resistance of 13.9 kΩ in parallel with a capacitance of 28.7 fF. This approximate model for the load impedance is used at the initial design phase and gives us some intuition as to how design choices affect $Z_{in,rect}$. After the initial design we estimate the input impedance through simulation as follows in which we approximate the input current as sinusoidal. The magnitude of the input impedance is calculated by dividing the peak-to-peak value of applied voltage by the peak-to-peak value of input current, $$|Z_{in,rect}| = \frac{V_{in,p-p}}{I_{in,p-p}},$$

while the phase of the input impedance is estimated by measuring the phase delay between applied voltage and input current, $\angle Z_{in,rect}=\angle(V_{in,p-p},I_{in,p-p})$. To further corroborate these estimates calculate the real part of $Z_{in,rect}$ by real $$\left(\frac{1}{Z_{in,rect}}\right) = \frac{2P_{in,rect}}{|V_{in}|^2}.$$

Strictly speaking $Z_{in,rect}$ is a non-linear function of the voltage applied and so varies over the period. Simultaneous conjugate matching assumes that the load impedance is constant. $R_L$ is linear whereas N $(R_{on,N}+R_{on,P})$ varies with the applied voltage. Fortunately for a well designed rectifier $R_L$>>N $(R_{on,N}\ R_{on,P})$ so $R_L$+N $(R_{on,N}+R_{on,P})$ is approximately constant. The other nonlinear element in our model is $C_{L,eq}$ but the nonlinear variation is a small compared of the overall impedance. We match to the typical value of this impedance achieving near-maximum power transfer, demonstrating that, for the input waveform in question, the non-linearity can be neglected. The weakness of the non-linearity is to be expected since the typical input impedance, $Z_{in,rect}$=13.9 kΩ‖28.7 fF, is dominated by the load impedance $R_L$=12 kΩ which is linear in parallel with N/2 $(C_{gc,N}+C_{gc,P})$=24 fF which is very weakly non linear.

C. Regulator

Figure 29:
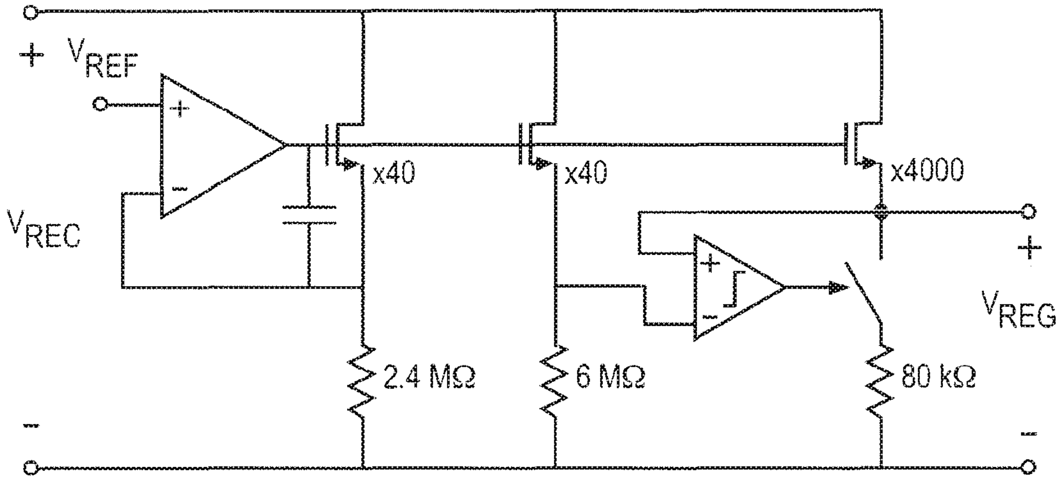
FIG. 29 illustrates an embodiment of a series regulator that incorporates two replica bias stages.

Regulator optimization is not the focus of this work but a regulator was needed to provided a stable 1.2V supply to some other devices on the die. A series regulator was used which incorporates two replica bias stages, FIG. 29. The first replica bias is used to generate the gate bias for the output stage, desensitizing the gate voltage to load switching. If the output stage current falls below approximately 8 μA the output voltage begins to rise, i.e. the load impedance becomes too large with respect to the replica bias. To overcome this problem a second replica bias and control loop maintains a minimum current of 15 μA through the output stage. Conceptually the loop tries to close the switch as the current falls below 20 μA and ensures an absolute minimum current of 15 μA.

VII. MEASURED PERFORMANCE

Figure 30:
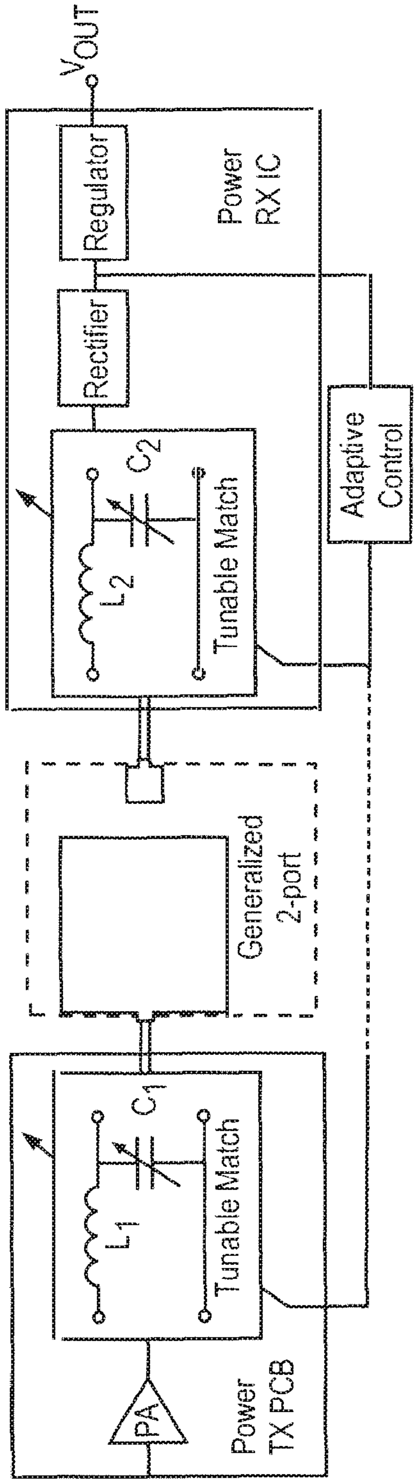
FIG. 30 shows an embodiment of the system.
Figure 31:
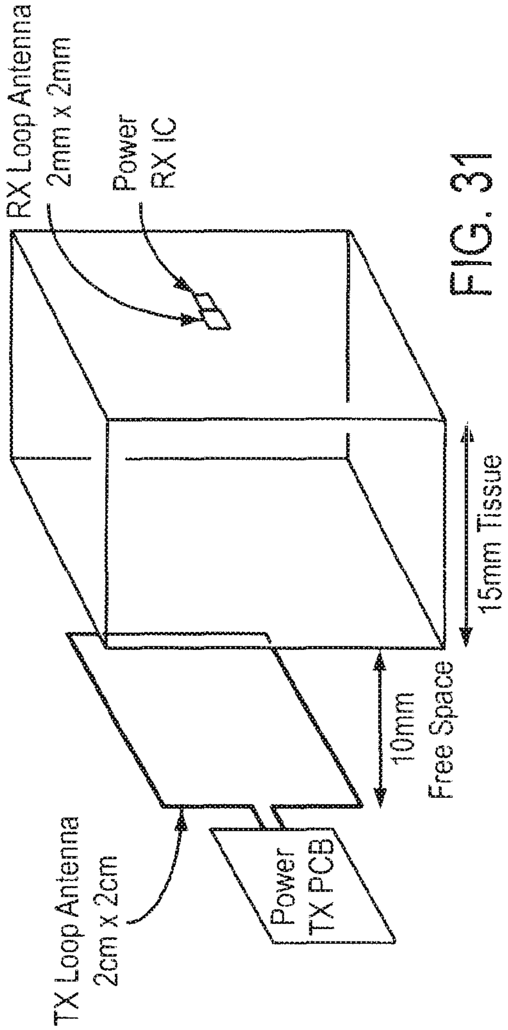
FIG. 31 shows two antennae according to the system axially aligned with muscle tissue therebetween.

A block diagram of an implemented embodiment is illustrated in FIG. 30. The power transmitter is implemented on a PCB incorporating a power amplifier and an adaptive match together with a 2 cm×2 cm transmit loop antenna. The power receiver consists of a 2 mm×2 mm receive loop antenna and the power receiving IC which includes adaptive match, rectifier and regulator. The transmit antenna is placed 1 cm above the tissue surface and the receiver implanted 15 mm deep in bovine muscle tissue with the two antennae axially aligned as illustrated in FIG. 31.

The power receiving IC was implemented in CMOS and bonded to the receive loop antenna with controlled bond wire length to realize the series inductance of the receive match. The receive match tunable capacitance, rectifier and regulator are all on chip. The gates and drivers which control the tunable capacitance were implemented on chip whilst the search algorithm was performed off-chip and the signals fed to the receiver chip in this embodiment of the device.

Figure 32:
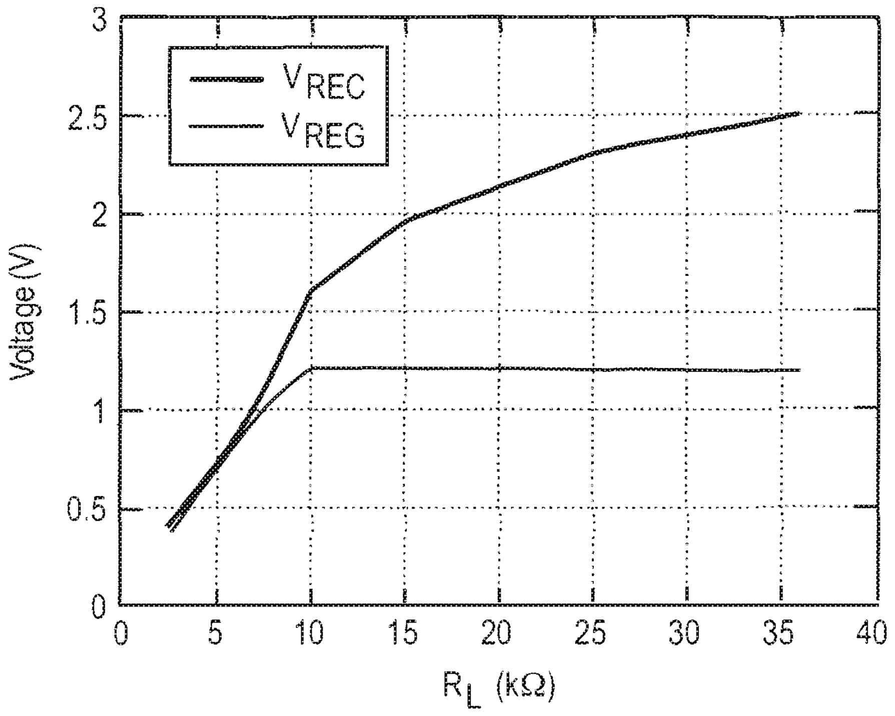
FIG. 32 shows a plot of rectifier and regulator output voltages versus load impedance as the load impedance was varied.
Figure 33:
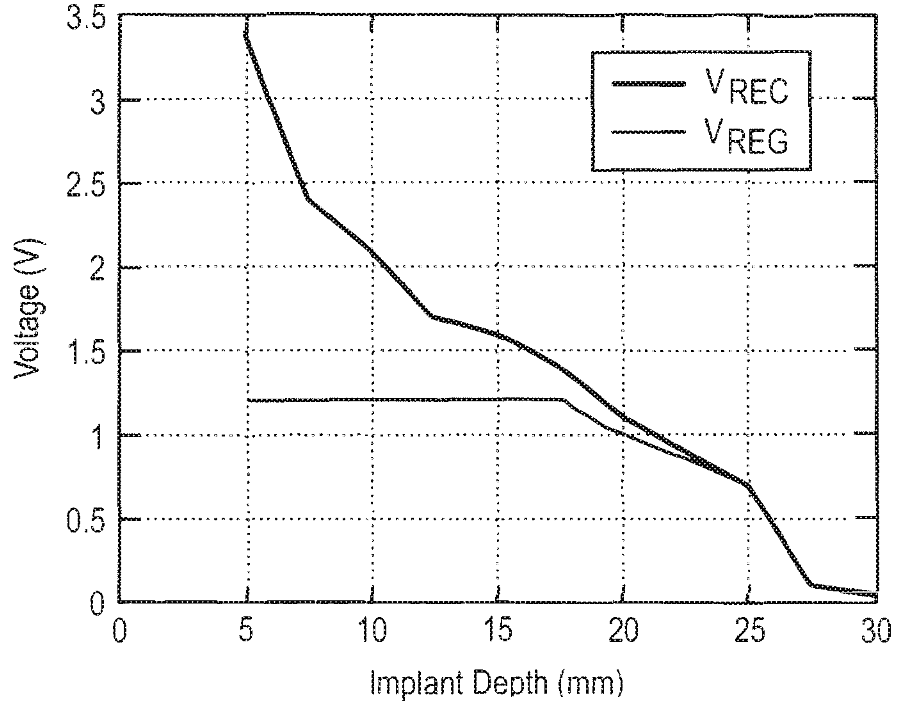
FIG. 33 shows a plot of rectifier and regulator output voltages versus implant depth for a particular load impedance.

The rectifier and regulator output voltages were measured versus load impedance as the load impedance was varied form 2.4 kΩ to 36 kΩ and are plotted in FIG. 32 for transmit input power of 250 mW. The regulator output of 1.2V±1% is maintained as the current load varies from 15 μA to 120 μA. The rectifier and regulator output voltages measured versus implant depth for a load impedance of 12 kΩ are plotted in FIG. 33. The regulator output of 1.2V±1% is maintained as the range varies from 7.5 mm to 17 mm. The measured rectifier efficiency is 65%. The combined startup time of the rectifier and the regulator is 4 μs, dominated by the regulator.

In order to evaluate the adaptive match we consider a +1 mm placement accuracy. First we ideally align the antenna, run the match adaptation and measure the rectifier output voltage, $V_{REC}$. Next we hold those match parameters fixed, misalign the antennae axially by 1 mm, increase the implantation depth of the receiver by 1 mm and measure $V_{REC}$ again. This corresponds to the voltage we would receive if we designed a static match for the ideal alignment but the realized link was 1 mm inaccurate axially and laterally. Finally we turn the match adaptation back on and measure $V_{REC}$ again. From those measured $V_{REC}$ we calculate the combined gain of the link and rectifier for each case. These are listed in Table IV.

TABLE IV

ADAPTIVE MATCH PERFORMANCE

| Link | Matching | Link Gain |
|---|---|---|
| Ideal | for ideal link | −32.1 dB |
| Non-Ideal | For ideal link | −35.8 dB |
| Non-Ideal | for non-ideal link | −32.3 dB |

Without adaptive matching an implant placement accuracy of 1 mm and tissue thickness estimation accuracy of 1 mm we could lose up to 3.7 dB of the link gain. However the adaptive match boosts the link gain by 3.5 dB for ±1 mm misplacement, recovering almost all of the lost gain. The link gain numbers in Table IV are of the link and rectifier together, the total gain of the link, rectifier and regulator is −33.2 dB. The performance is summarised in Table V.

TABLE V

| PERFORMANCE SUMMARY | |
|---|---|
| Tx Antenna Size | 2 cm × 2 cm |
| Tx Power | 250 mW |
| Operating Frequency | 915 MHz or 1 GHz |
| Inter-Antenna Dielectric | 10 mm free space and 15 mm bovine muscle tissue |
| Rx Antenna Size | 2 mm × 2 mm |
| Technology | 0.13 μm CMOS |
| Area | 0.37 $mm^2$ |
| Startup Time | 4 μs |
| Rectifier Efficiency | 65% |
| Gain of Link, Rectifier and Regulator | −32.2 dB |
| DC Power Out | 140 μW @ 1.2 V |

APPLICATIONS

The present invention can be applied to provide a remote power source for the operation of implantable devices such as cardiac rhythm management systems (for example, pacemaker and cardiac defibrillator), neurostimulators, drug delivery systems, and medical sensors (for example, blood glucose sensors.) The internal battery of those devices can then be removed. This will dramatically reduce the size of the implanted devices allowing more effective drug delivery and neurostimulation. For example implanted drug delivery systems can be located closer to the cancer cells.

The present invention can be applied to provide a "self-powered" data link to any implantable device. The data link can be used to remotely program the operation of the devices and retrieve information from the devices. This data link will not consume any power from the internal battery of the implantable devices. Thus, it will not affect the battery lifetime of the implantable devices. In addition, the present invention provides enough power not only for the data transmission but also support two-way encryption. This security measure will avoid hackers from breaking the normal operation of the implantable devices.

The present invention can also be applied to the embedding of security IDs inside medical pills such as prescription drugs. Power is delivered from the external transceiver (pharmacy pad) to the pill where a processor and related application programming performs encryption and authentication. This security ID can also be used for post-mismedication tracking. The external transceiver will track the security ID inside the body and check out the type of medicine that had been taken by patients.

Figure 34:
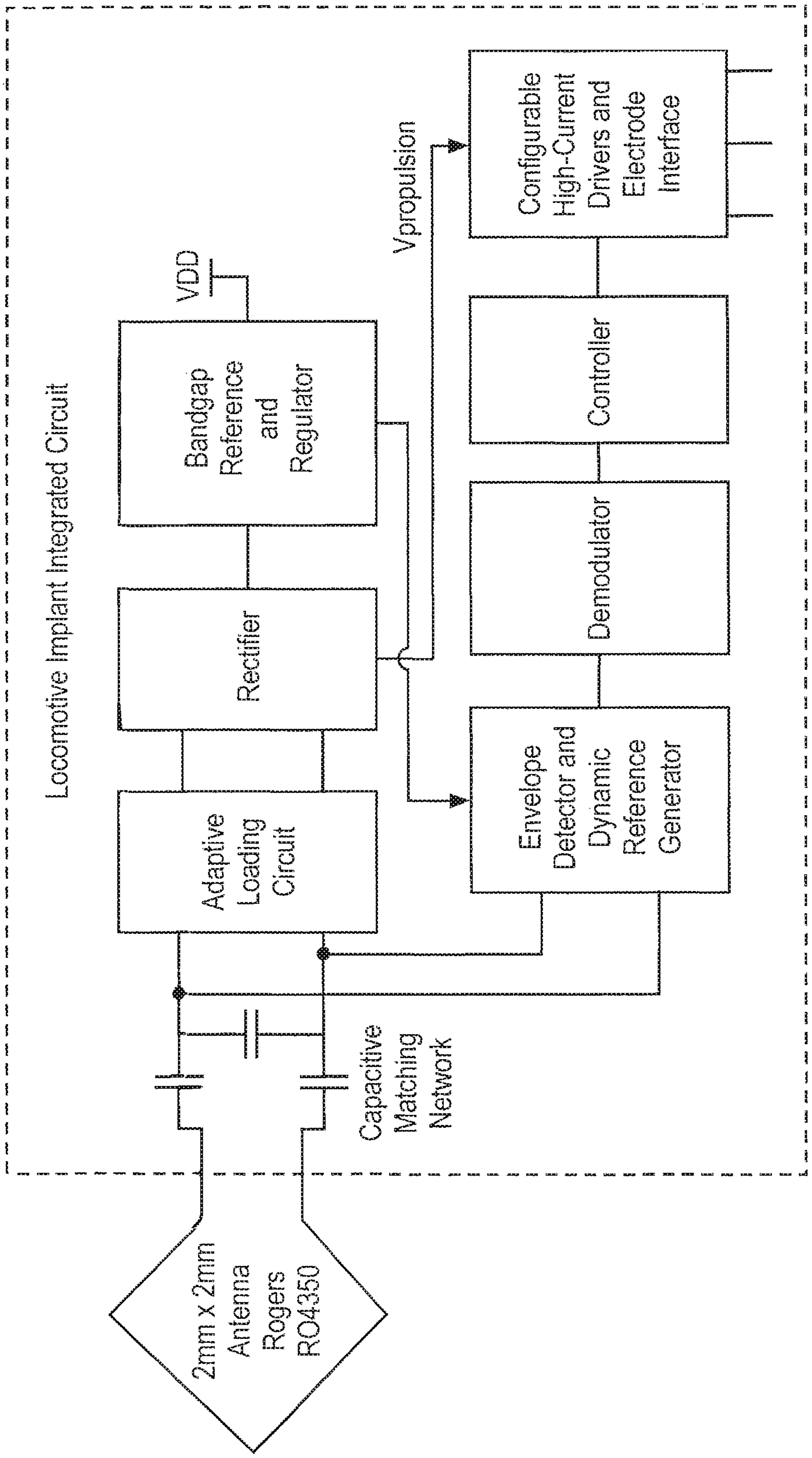
FIG. 34 illustrates an overview of an integrated circuit architecture for an embodiment.

The purpose of the chip was to create a wireless prototype that demonstrates the effectiveness of the propulsion system at the mm-scale. The specifications were derived from the requirements of the propulsion methods, which need approximately 1 mA of current for cm/sec speeds. The integrated circuit (IC) must receive both power and data from the external receiver to propel and navigate the device, and must operate with a limited power budget. The chip architecture is shown in FIG. 34, and the IC consists of a matching network, a charge-pump connected rectifier, a regulator, a bandgap reference circuit, a demodulator, a digital controller, and configurable electrode drivers. There are no external components except for the receiving antenna. The key challenge in this design is driving the high-current propulsion system efficiently and controllably while continuously harvesting RF energy. Power is the primacy limitation, and minimizing power consumption was critical for the design.

The non-linear electrode-fluid resistance limits the minimum voltage required to drive the current, and is estimated at approximately 200-300 mV. The propulsion system dominates the power budget consuming over 90% of the total delivered power to the chip. The required 1 mA of current for propulsion needs to be sourced from no more than 300 mV while the active circuitry requires a regulated voltage of 700 mV and draws approximately 15 μA. Using a linear regulator for the propulsion system is inefficient, and a switching regulator requires large passive components, accurate on-chip clock, and complex controllers. Therefore, the chip was designed to drive the propulsion system from the first rectifier stage, which provides an unregulated 200-300 mV supply depending on the received power and can source the required current. Because the loading from the propulsion system varies with navigation, an adaptive loading network is also necessary to maintain effective matching at the antenna. The first rectifier stage is followed by three additional stages to boost the voltage, which is then regulated for the analog and digital circuits.

Figure 35:
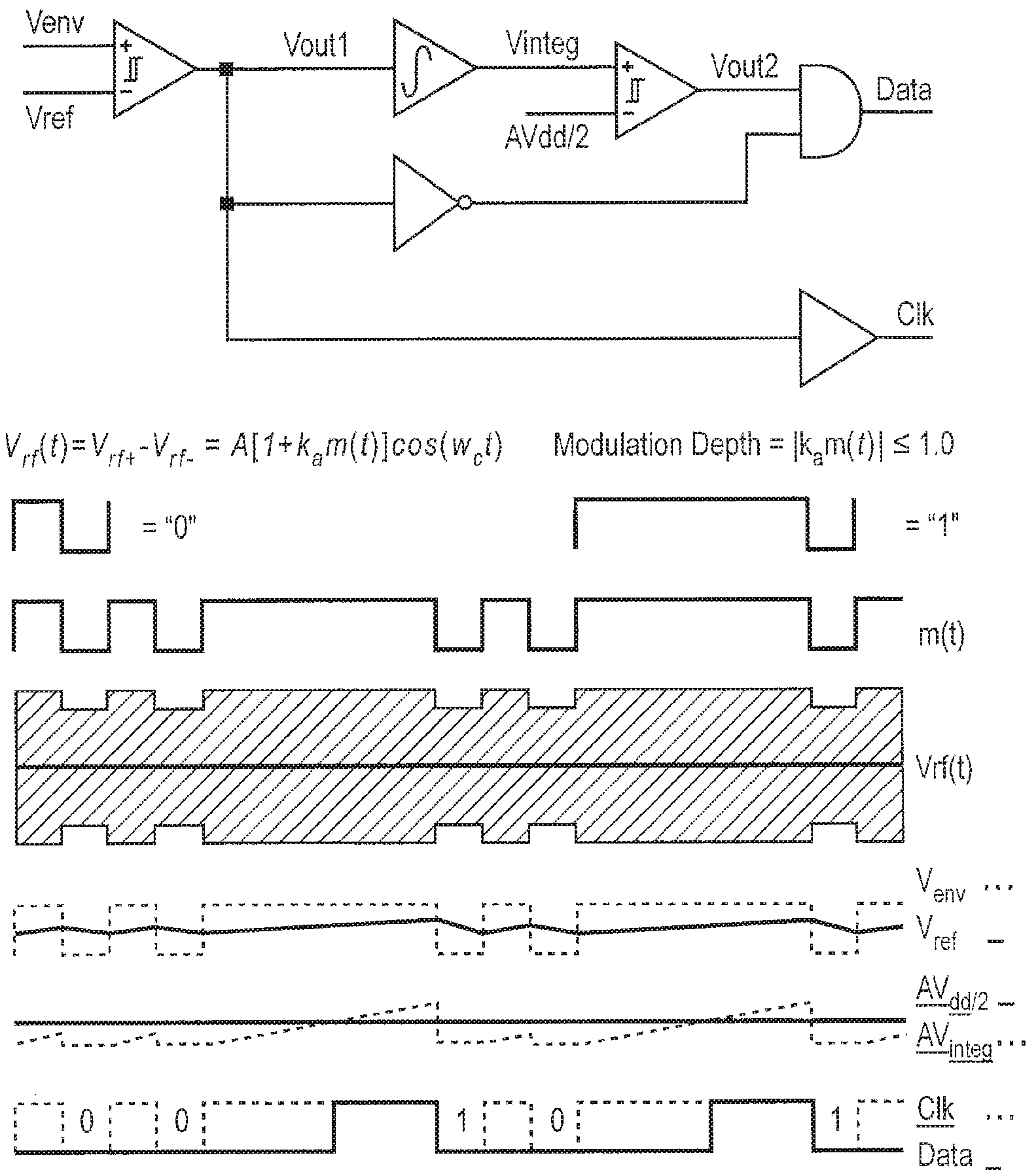
FIG. 35 illustrates the data receiver, including demodulator.

The size requirements prohibit the use of external energy storage components, so power must be continuously transmitted to the device. Power transmission must adhere to FDA safety regulations for tissue heating. From prior work, mm-sized antennas can receive approximately 200-300 μW at low-GHz frequencies safely. A 2 mm×2 mm antenna provides sufficient power for this design, and performing a frequency sweep with the antennas yields an optimal frequency of 1.86 GHz. It is important that the modulation scheme minimally affects the power transfer to the device because of the limited power budget. Frequency-shift keying (FSK) and phase-shift keying (PSK) operate with a constant envelope, but the demodulator requires either a frequency or phase-locked loop for carrier synchronization, which consumes significant power at high frequency. Amplitude modulation does not require carrier synchronization, and the modulation depth and duty cycle can be designed to minimize the impact on power delivery. For this reason, we implemented amplitude shift keying (ASK) with low modulation depth (minimum of 9%), and the pulse width (PW) encodes the data allowing for asynchronous clock and data recovery with simple circuitry. A high-level description of the data receiver is shown in FIG. 35. The demodulator provides both the clock signal for the digital controller and decodes incoming data. The demodulator interface with the matching network uses two rectifiers: the first has a small time constant and tracks the envelope, and the second has a large time constant and approximates the average of the envelope. These two signals are input to a comparator to generate the digital signal $V_{out1}$. This signal is buffered to produce a digital clock. $V_{out1}$ is also integrated and compared to a threshold to decode the data. With this implementation, long pulses produce high output and short pulses produce low output. The demodulated data is captured on the falling edge of the clock by a low-power digital controller, which configures the high-current electrodes for driving the propulsion system.

VIII. CIRCUIT IMPLEMENTATION

A. Antenna and Matching Network

Figure 36:
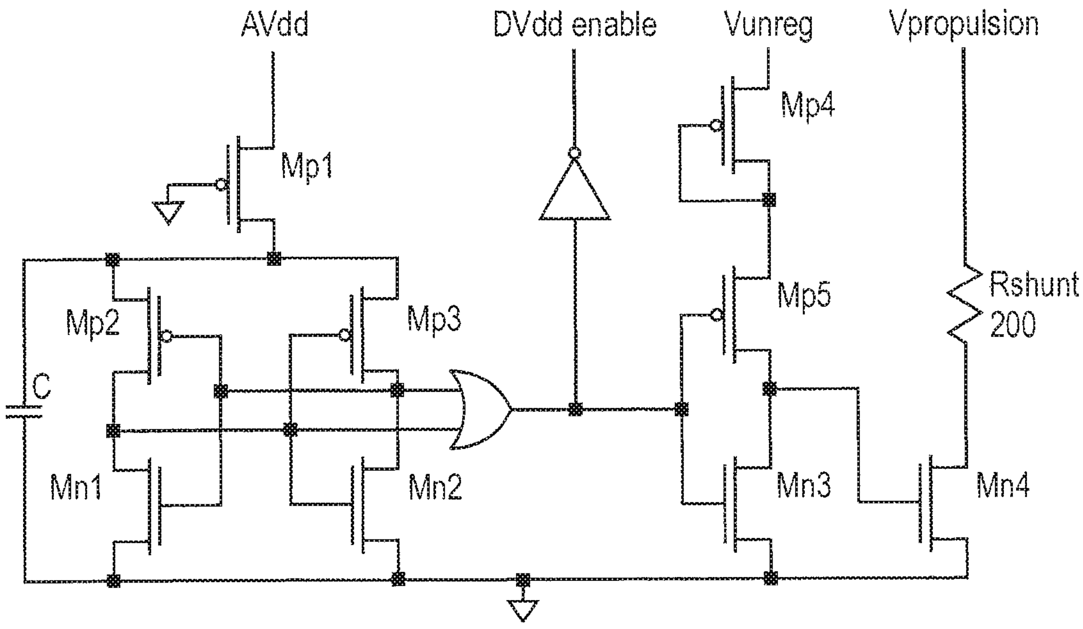
FIG. 36 illustrates power-on shunting and Vad enable circuit.

The antenna dominates the size of the prototype, and is implemented with a 2 mm×2 mm loop on a PCB using Rogers 4350 substrate. External components are not possible due to size constraints, so a balanced L-match consisting of only capacitors was implemented because on-chip inductors have significant loss and occupy large area. The total quality factor of the antenna and the matching network in air is estimated at 39. The chip input impedance is dominated by the propulsion system, and loading varies significantly during normal operation. Therefore, an adaptive loading network was implemented to maintain an effective match. When the chip is powered on and before the controller is reset, the gate of transistor $M_{n4}$ in FIG. 36 is weakly pulled up by $V_{unreg}$, which shunts the first rectifier stage with an internal 200 Ω resistor. After the digital supply is enabled, the weak pull-down transistor $M_{n3}$ slowly turns off the shunt resistor. Once the power-on reset (POR) signal has been issued, the digital controller is reset and takes control of the network, adjusting the resistance based on incoming data.

B. Start-up and Power-on Reset Circuits

Figure 37:
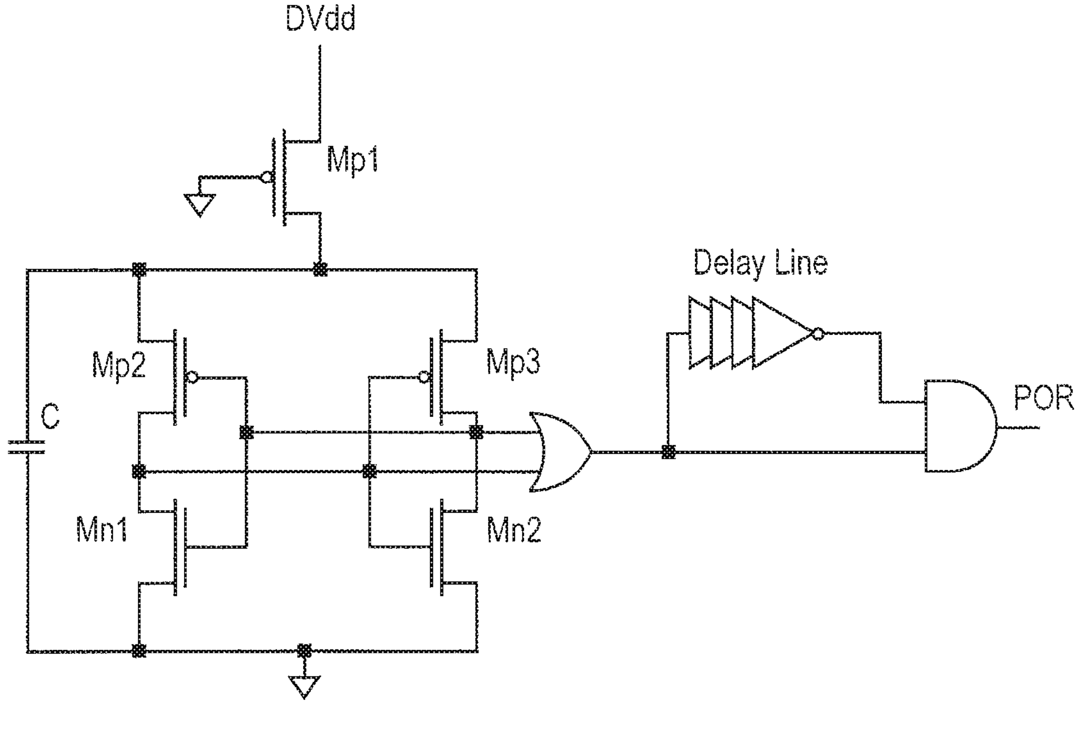
FIG. 37 illustrates power-on reset signal generation circuit.

Start-up circuitry for the initial power-on is necessary to ensure that the antenna impedance maintains a match and that the chip enters a known state. A start-up network that turns on a pass transistor for the digital supply voltage is shown in FIG. 26. The cross-coupled inverters are skewed in opposite directions to prevent metastability, and the delay is controlled by a capacitor at the supply of the cross-coupled inverters that slowly charges through a weak current source. This delay ensures that the analog supply voltage has reached a stable 700 mV before powering on the digital circuits. Once the digital supply is enabled, a POR pulse is issued after an additional delay. This pulse generation is shown in FIG. 37. The pulse width is set by the delay of a capacitively loaded inverter chain that provides a sufficient duration pulse to reset the controller.

C. Power Management

When the antenna receives 500 μW, the RF input voltage to the rectifier is 350 mV. Conventional diode-capacitor ladder rectifiers suffer from low efficiency at low input voltage. Therefore, charge-pump connected self-driven synchronous rectifiers (SDSR) are used with low-Vt devices. The first stage of the rectifier is sized 10 times larger than the consecutive stages because the propulsion system is driven directly from this first stage. It outputs an unregulated 200-300 mV and drives roughly 1 mA of current. The remaining three stages are all sized the same and output 0.9-1.2 V while driving 15 μA. The pump capacitance between these three stages is 5 pF. The simulated efficiency of the rectifier is approximately 55%.

Figure 38:
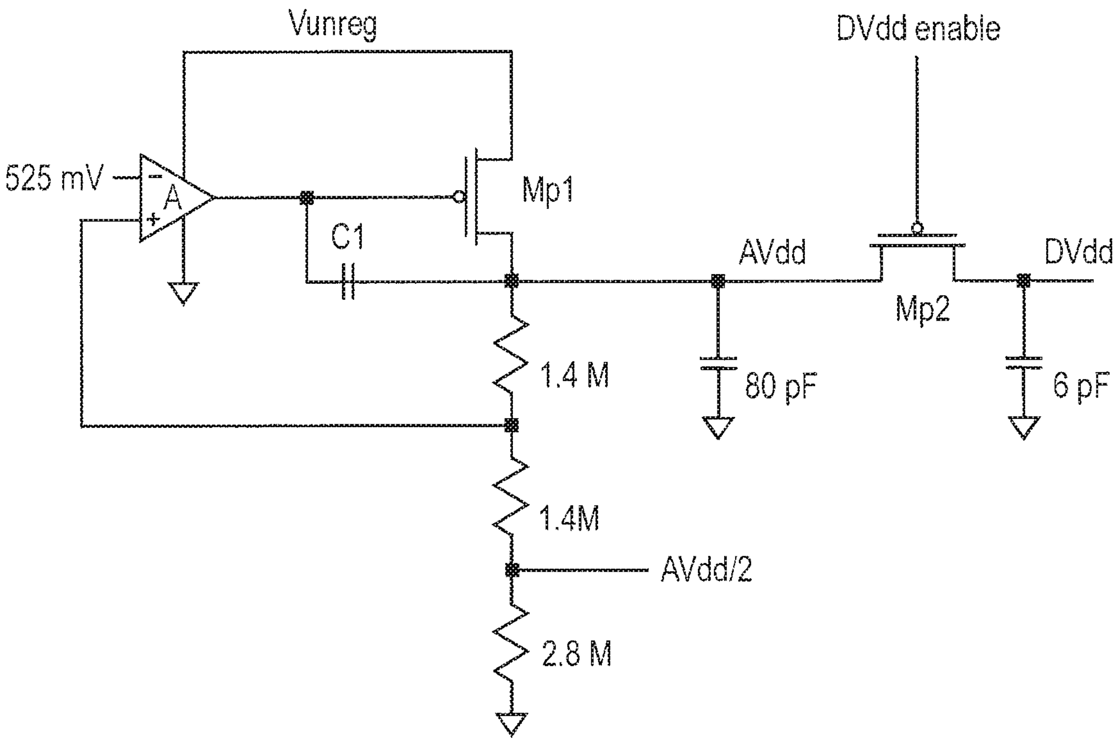
FIG. 38 illustrates the regulator circuit with both analog and digital supply.

The unregulated supply voltage fluctuates significantly with variations in available power due to varying link gain as the device moves, propulsion driver strength, and switching noise from the digital circuits. The device must also be insensitive to temperature variations. To create a stable 700 mV supply for the active circuitry, we implemented a low drop-out voltage regulator that relies on a bandgap reference circuit. A total of 86 pF of smoothing capacitance was used to maintain stable voltage at the supply. The schematic of the regulator is shown in FIG. 38. The regulated voltage is sampled via a resistive voltage divider and is compared to the bandgap reference output voltage of 525 mV. The resistive divider also outputs a voltage of $V_{dd}/2$, providing a reference for the demodulator. Capacitor C1 is added to help stabilize the feedback loop. The regulator has an overall efficiency of 58%. However, the dissipated power due to the rectifier inefficiency is only $$\eta_{degradation} = \frac{P_{lost}}{P_{total}} = \frac{(V_{unreg} - V_{reg}) * I_{reg}}{P_{propulsion} + P_{circuits}} = 3\%$$

of the total power consumption because the unregulated propulsion system dominates power usage.

D. Clock and Data Recovery

Figure 39:
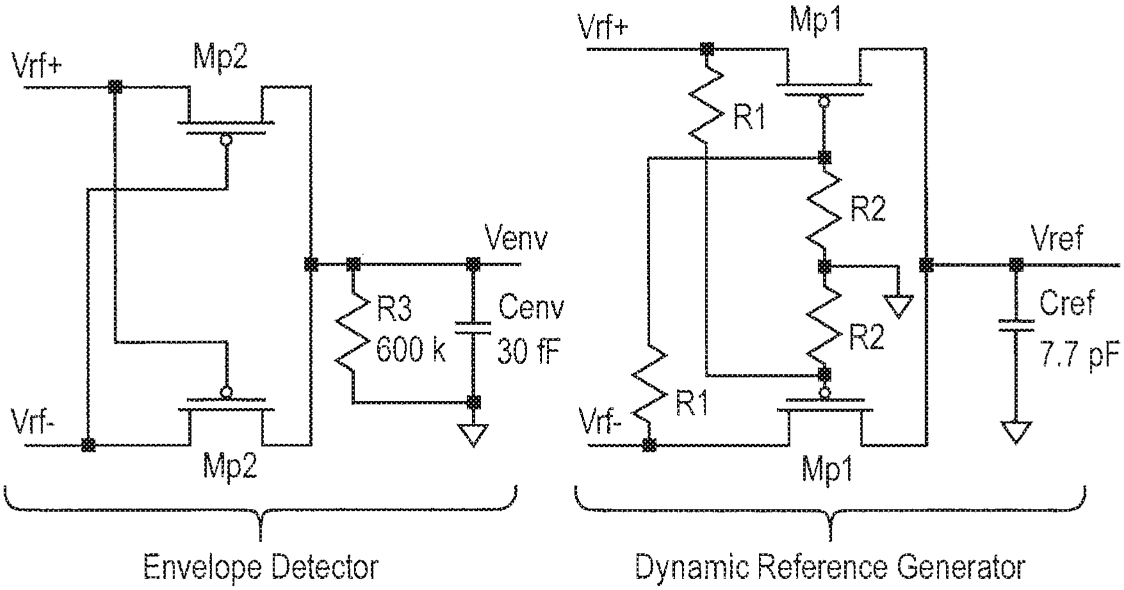
FIG. 39 illustrates envelope detection and dynamic reference voltage generation circuits.

The low modulation depth and fluctuating input power make it impossible to use a fixed reference voltage for the ASK threshold detector. Instead, a dynamic reference voltage is generated concurrently with envelope detection. The schematic of the envelope detector and dynamic reference generator is shown in FIG. 39. Both circuits use cross-coupled PMOS transistors to achieve full-wave rectification. The envelope detector RC time constant filters out the carrier and passes the data. In the dynamic reference generator, the RF input voltage is resistively divided to weakly turn on the cross-coupled transistors. The higher on-resistance and larger load capacitance form a large RC time constant, which effectively averages the envelope. The resistor at the output of the envelope detector aligns the average of the envelope with the dynamically generated reference voltage.

Figure 40:
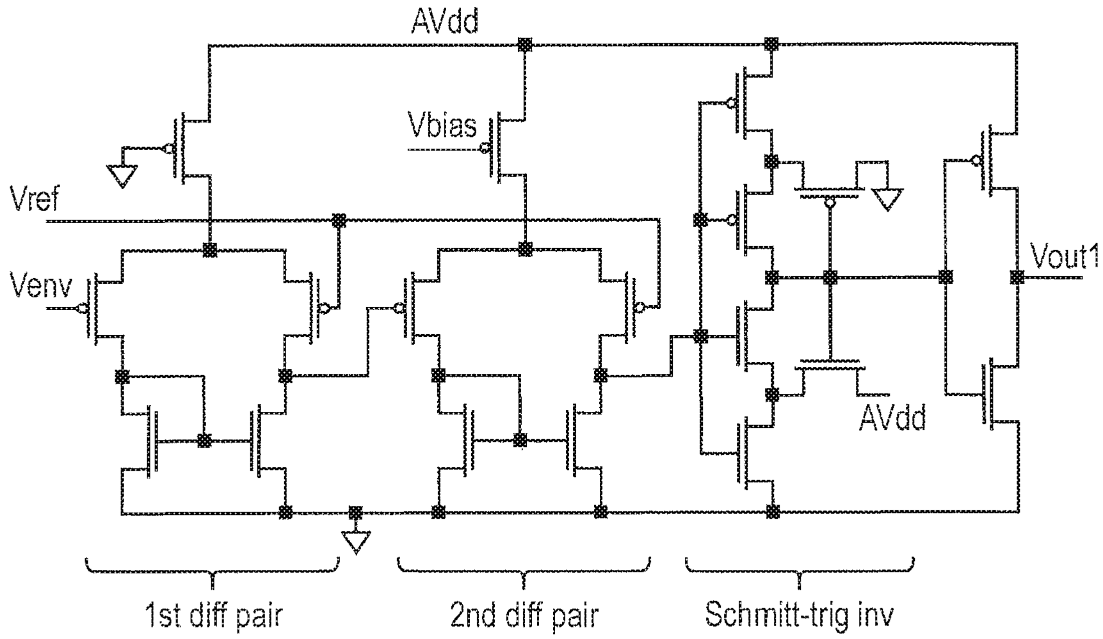
FIG. 40 illustrates a first comparator that converts the envelope into digital signal.
Figure 41:
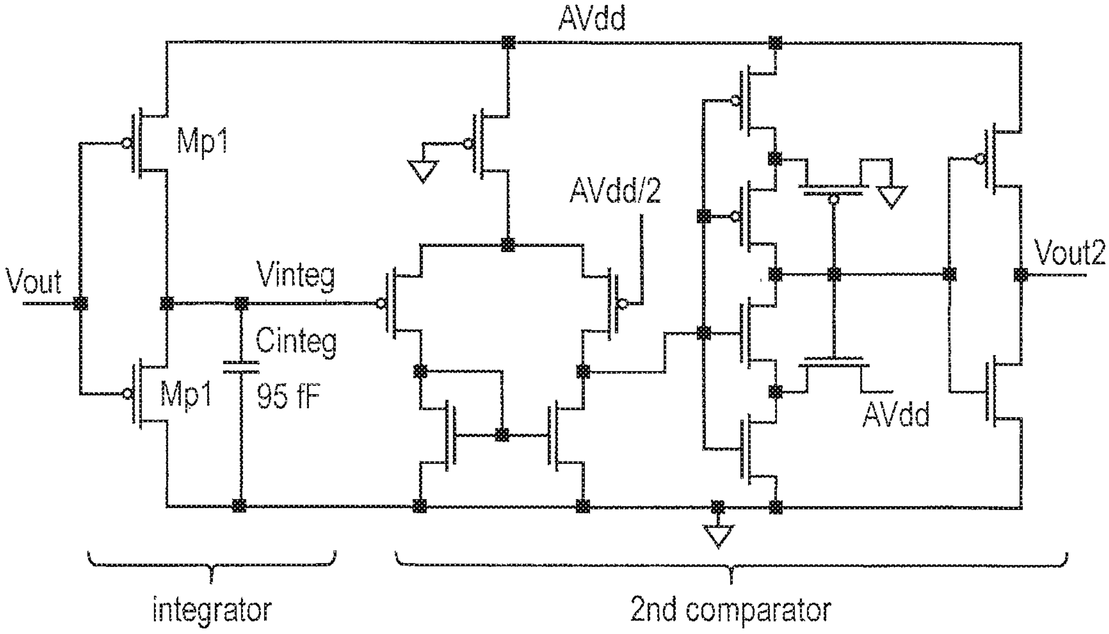
FIG. 41 illustrates an integrator and second comparator for data decoding.

Clock and data signals are recovered from the envelope and the dynamic reference, which are first input to a comparator to generate the full-swing digital signal $V_{out1}$. This comparator consists of two differential amplifier stages followed by a Schmitt-trigger inverter as shown in FIG. 40. Two low-power differential amplifiers ensure that the gain remains high for a wide range of common-mode input voltages, which vary depending on input power. The Schmitt-trigger inverter reduces the crowbar current due to slow transitions of the amplifier output, and it also decreases sensitivity to noise. The resulting digital signal is both buffered to generate the clock and integrated to decode the data as described in FIG. 41. The integrator consists of a skewed inverter with a capacitive load to provide slow rising and fast falling edges. This capacitance defines the pulse width that causes the data to transition from low to high, and therefore sets the minimum and maximum data rates. On the falling edge of each incoming pulse, data is captured from a comparator that compares the integrated result with a fixed reference at $V_{dd}/2$. This comparator consists of a single differential pair followed by a Schmitt-trigger inverter. The entire demodulation system draws a current of 5 μA.

E. Controller

The digital controller receives data and clock signals from the demodulator, and configures the propulsion system drivers and the adaptive loading network. Data transmission begins with a 5-bit prefix that, when received, enables a shift register to begin accepting the 55-bit data packet. While data is being shifted into the register, the prefix detection circuitry is disabled. Once the entire packet is received, the shift register pushes all the data to a memory register that stores it until the next valid transmission. By only enabling the necessary circuitry in each stage of data reception, power consumption is minimized. Because the clock is derived from the data signal, when no data is being received the only current drawn is due to leakage. The estimated average power consumption of the digital controller while receiving data is 2 μW, and it occupies 0.009 $mm^2$.

F. Configurable High-Current Drivers

The chip has 6 high-current electrode drivers with configurable strength to accommodate both propulsion mechanisms. Each of the drivers can be independently set to V propulsion from the first rectifier, ground, or left floating. Additionally, the driver strength can be controlled with 4 parallel transistors, and ranges from 20-1000Ω. This configurability is necessary to adapt to uncertainty in electrode-fluid resistance and to enable speed and steering control. Data in the memory register directly controls the electrode driver state and strength.

IX. EXPERIMENTAL VERIFICATION

Experimental tests verified all the elements of the design including wireless power transmission, the ASK-PWM data transfer, the analog and digital circuitry, and the two propulsion schemes. Independent tests evaluated the wireless link and the circuit performance, and testing of the complete system demonstrated navigation and propulsion through fluids. Each experiment will be described in detail in this section. The overall circuit performance is summarized in Wireless Power Transmission.

Figure 42:
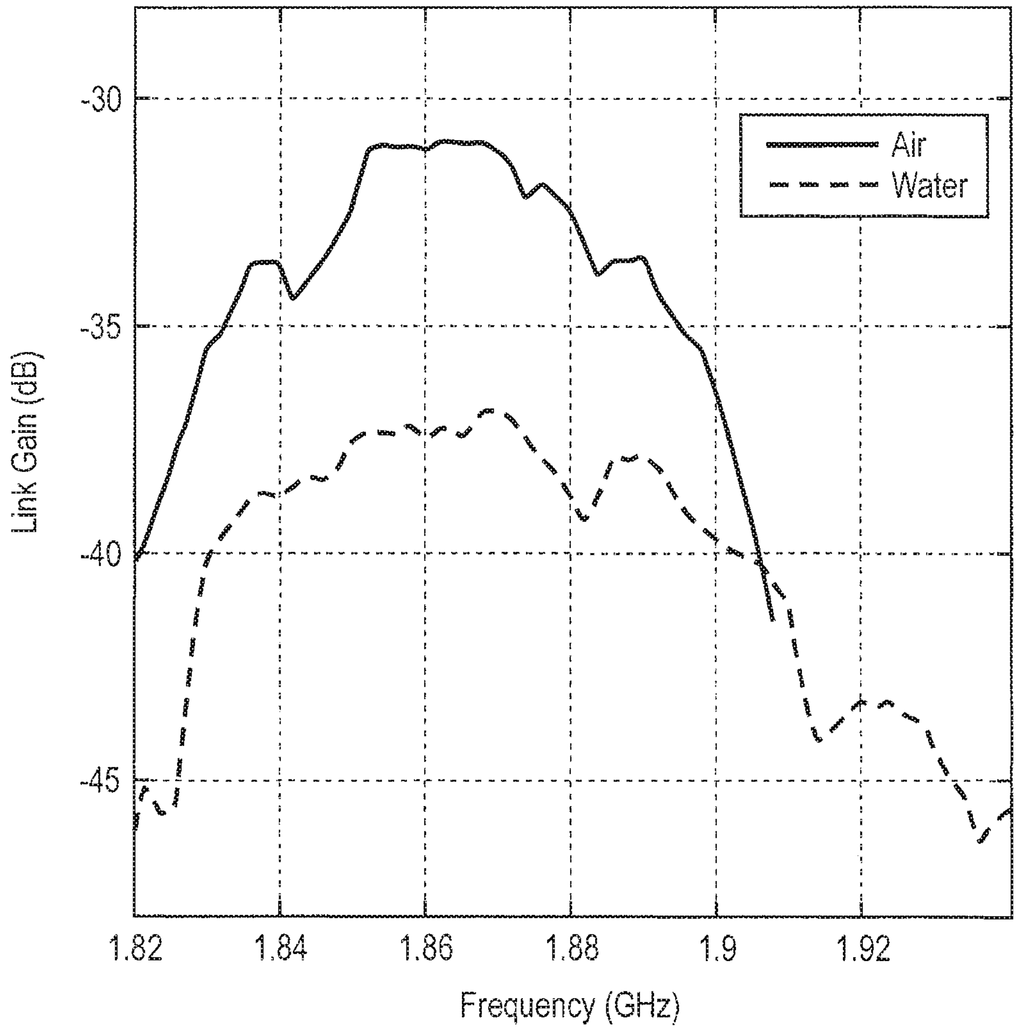
FIG. 42 illustrates measured link gain in air and water associated with the transmitter.
Figure 43:
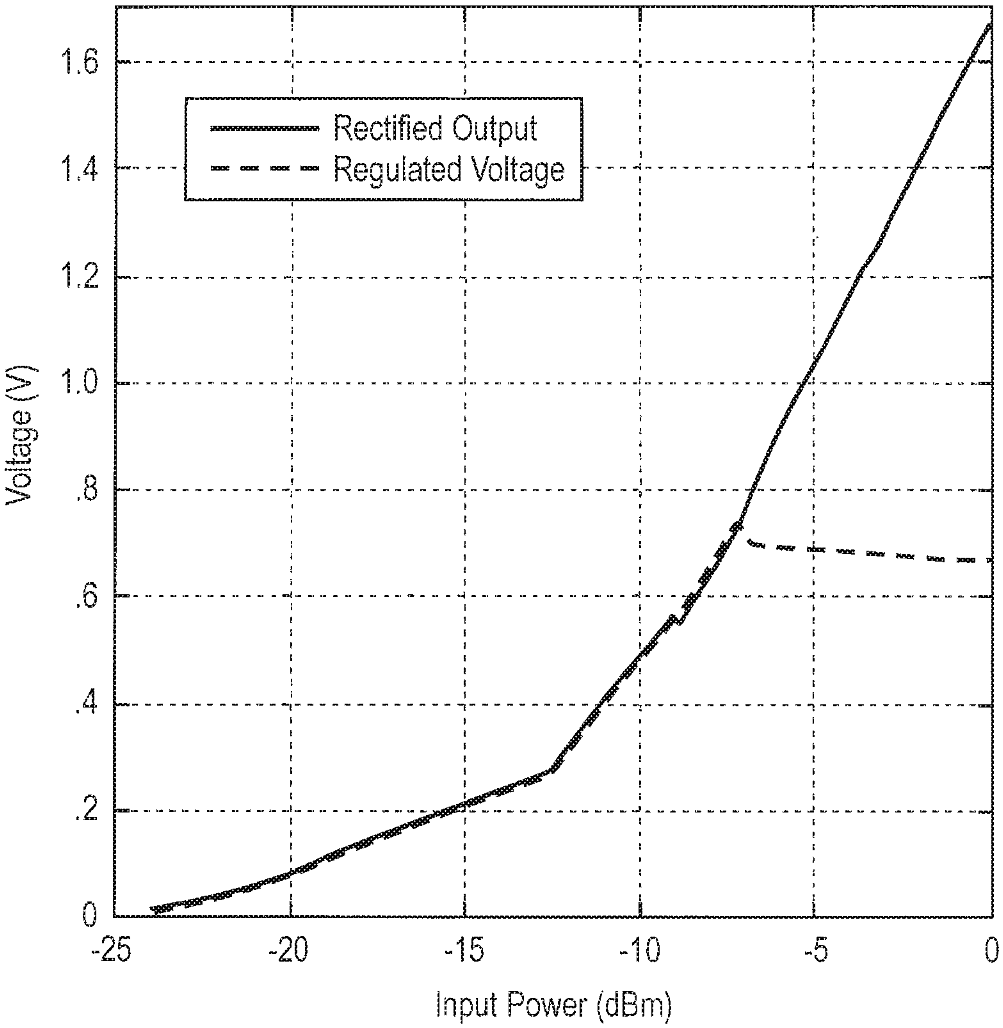
FIG. 43 illustrates plots of rectified output voltage and regulated voltage as a function of input power.

The transmitter consists of a signal generator, a high-frequency amplitude modulator, a power amplifier, and a 4 cm×4 cm loop antenna fabricated on PCB. The IC was wire bonded to a 2 mm×2 mm antenna fabricated on a Rogers 4350 substrate to minimize RF losses. A frequency sweep of the link gain was tested at a separation distance of 5 cm both in air and with the device placed on the surface of water. The measurements are shown in FIG. 42. From this plot, the quality factor in air is 39 for the antenna including the matching network. The rectified output voltage and the regulated voltage are plotted as a function of input power in FIG. 43, showing that the device first powers on with roughly −7 dBm. With a rectifier efficiency of approximately 55%, roughly 2 W must be transmitted to receive 500 μW, resulting in approximately 250 μW of usable power after rectification.

A. ASK-PWM Data Transfer

Figure 44:
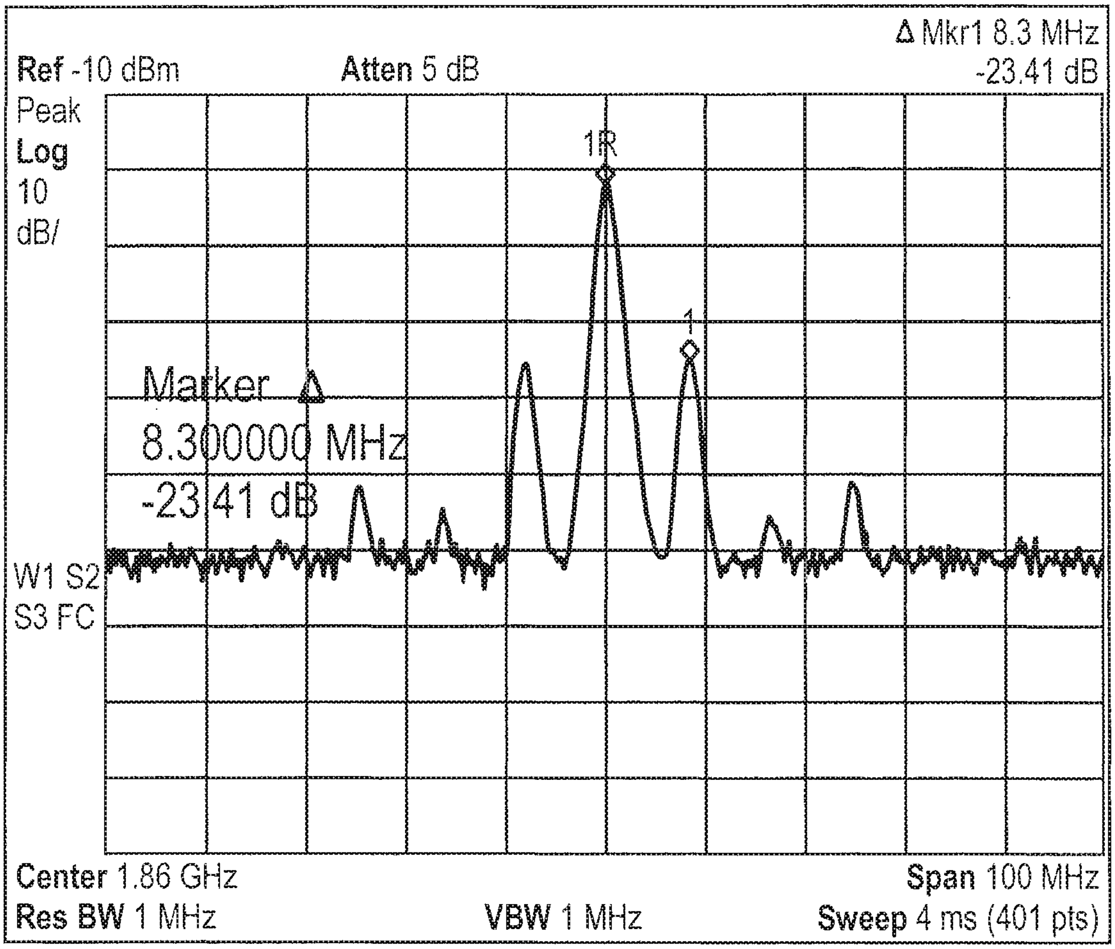
FIG. 44 illustrates the spectrum of the 1.86 GHz carrier modulated at 9% depth with an 8.3 MHz clock.
Figure 45:
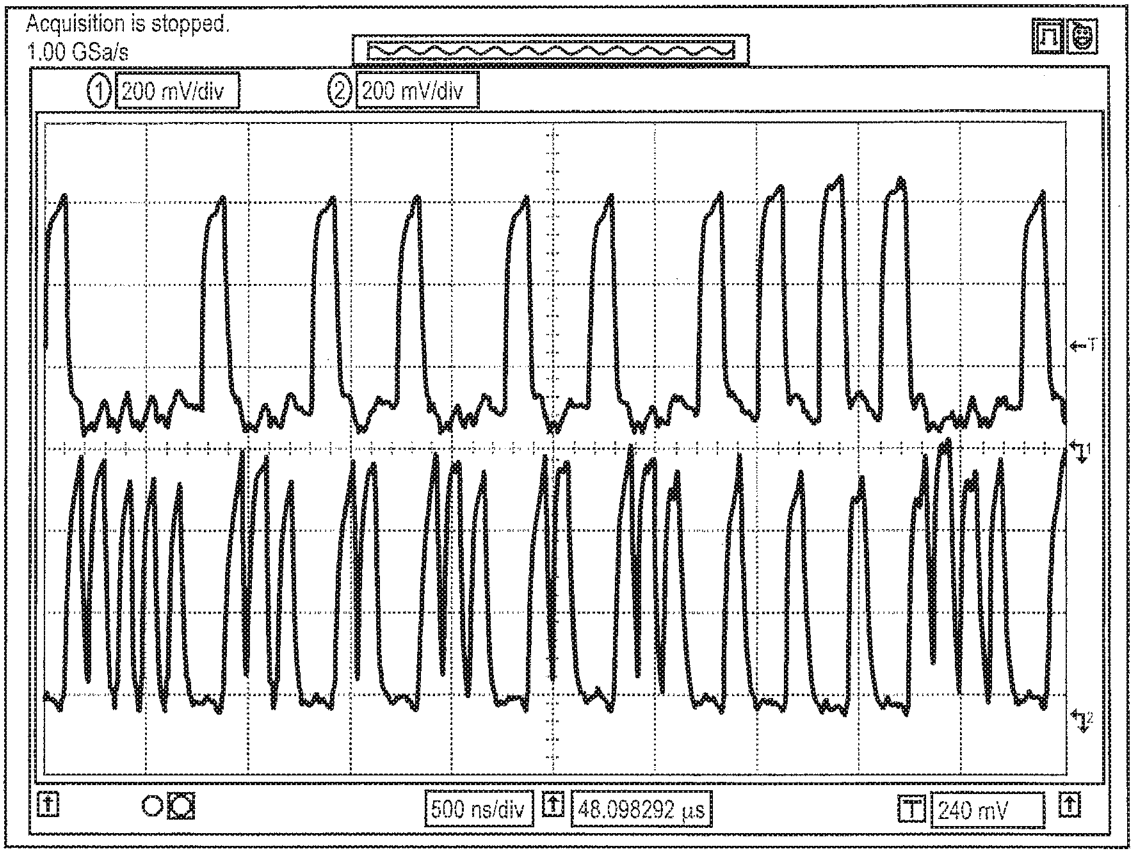
FIG. 45 illustrates measured waveforms of data and clock signal at the output of the demodulator.

Data modulation was designed to minimize impact on power delivery with a low power circuit implementation. To accomplish this, an asynchronous design was implemented that operates with minimal modulation depth and without carrier synchronization circuitry. This method allows for variable data rates and modulation depths. In order to test the range of operation, a versatile high-frequency modulator was constructed. The data signal was generated from an FPGA and input to the modulator, which modulates the output from the signal generator at an adjustable depth from 0-100%. The FPGA was able to stream data at up to 25 Mbps, and the chip properly received data from 2.5-25 Mbps. Additionally, the chip functioned with as low as 9% modulation depth. The spectrum of the carrier modulated at 9% with an 8.3 MHz clock is shown in FIG. 44, and the received clock and data signals on chip are shown in FIG. 45. The power consumption of the demodulating circuitry is approximately 5 μW at 10 Mbps, resulting in energy efficiency of 0.5 pJ/bit.

B. Fluid Propulsion

The IC was designed to function with either of the described fluid propulsion mechanisms. The chip and receive antenna are encapsulated in RF-transparent epoxy to protect them from the fluid. The leads from the electrodes are exposed to adapt the device for use with either of the fluid propulsion methods. For MHD propulsion, these leads are positioned to directly connect to a conductive fluid, and salt water was used for testing. For the method relying on asymmetric fluid drag forces, the electrodes are connected to loops of wire that oscillate the device. In both test cases, the device floats on the surface of the water with a neodymium magnet placed next to the fluid to provide a magnetic field. Even though testing was performed on floating devices, both propulsion methods can function when fully submerged.

Figure 46:
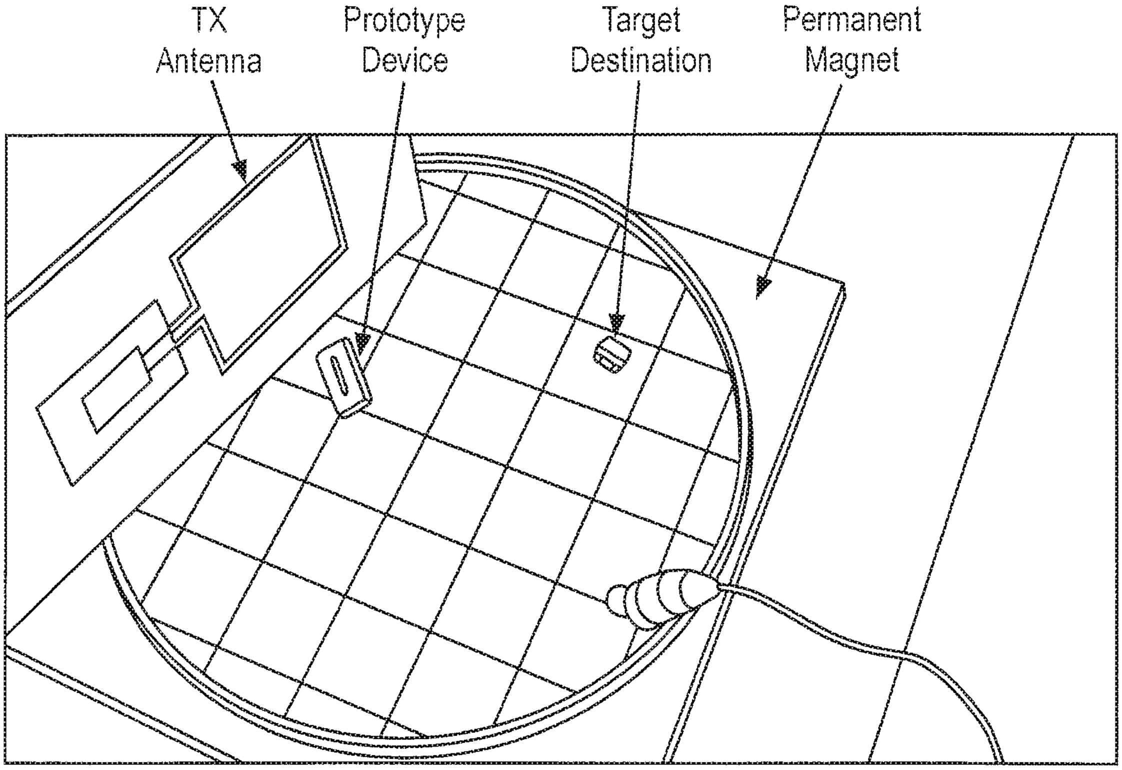
FIG. 46 illustrates a MHD propulsion set-up.
Figure 47:
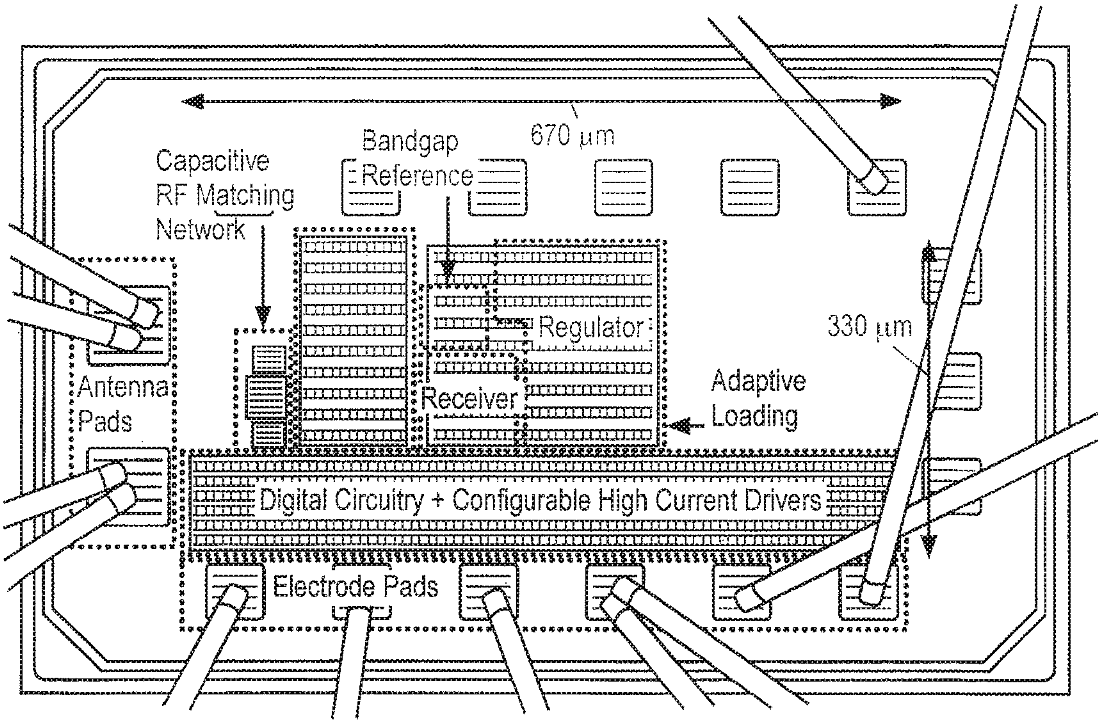
FIG. 47 illustrates an overview of the chip layout for the chip architecture illustrated in FIG. 34.

The experimental setup for MHD propulsion is shown in FIG. 46. During propulsion testing, the external antenna tracked the device at a distance ranging from 2 to 5 cm. Data is continuously transmitted with commands to control the motion. The device achieves speeds of up to 0.53 cm/sec in a 0.06 T field with approximately 1 mA, and can be navigated successfully along the surface of the water. Performance improves as the magnetic field is increased, so MRI systems will generate approximately 100 times as much propulsion force.

The setup for asymmetric fluid drag propulsion is very similar to MHD propulsion. The device is connected to 40 loops of wire, which are oriented to oscillate it. The prototype has an attached fin that experiences asymmetric fluid drag when oscillating. By changing the orientation of the magnetic field, the device can oscillate along the surface of the water, or into and out of the water. The external antenna is again placed above the device and continuously transmits data. The forces on the device are much stronger for this method because of the additional loops and smaller load; however propulsion is much more difficult to control. This method is also more sensitive to non-uniformities in the magnetic field. Additionally, the antenna link degrades as the device rotates, causing frequent errors in data reception. For this method to operate effectively, a new antenna link and a feedback controller are necessary.

TABLE I

PERFORMANCE SUMMARY

| | |
|---|---|
| **Rectifier** | |
| Rectifier Topology | 1 + 3 Asynchronous Self-Driven |
| Load @ 0 dBm | 0.5-2 mA @ 0.2 V (unreg) |
| | 20 μA @ 0.7 V (reg) |
| Efficiency @, 0 dBm | 55% |
| Rectifier Chip Area | 0.3 $mm^2$ |
| **Bandgap Reference and Regulator** | |
| Bandgap Power Consumption | 5 μW @ 1.2 V, 25° C. |
| Regulator Efficiency | 60% |
| PSRR | −20 dB (@ 8.5 MHz) |
| On-chip regulation capacitance | 72 pF |
| Bandgap Reference Chip Area | 0.0025 $mm^2$ |
| Regulator Chip Area | 0.03 $mm^2$ |
| **Demodulator** | |
| Modulation Type | ASK + PWM |
| Carrier frequency | 1.86 GHz |
| Data Rate | 2.5-25 Mbps |
| Power Consumption | 5 pW @ 10 Mbps |
| Sensitivity | −10 dBm |

TABLE I-continued

| PERFORMANCE SUMMARY | |
|---|---|
| Modulation Depth | ≥9% |
| Energy per bit | 0.5 pJ/bit |
| Demodulator Chip Area | 0.007 $mm^2$ |
| Power Breakdown | |
| Bandgap Reference | 5 μW |
| Regulator | 5 μW |
| Demodulator | 5 μW |
| Digital Controller | 5 μW |
| Fluid Propulsion System | 250 μW* |
| Total | 267 μW |

*Varies with input power and loading from propulsion

X. OTHER CONSIDERATIONS

Other considerations with respect to both the MHD and the AFD embodiments are that the magnetic field can be static or time varying, using permanent magnets, electromagnets, on device or external magnets, as well as current on the device to control motion.

3D control can be achieved by re-orienting the magnetic field to move in different directions, orthogonal loops of wire can also be used to tilt the device Adjusting the buoyancy will have an effect on 3D control. This can accomplished with mechanical deformation of the shape such as adjusting the size of an air pocket or the volume of the device itself. The density of the materials could also be adjusted by controlling the temperature. Additionally gases can be created from the fluid through the process of electrolysis for MHD, and these gases can adjust buoyancy.

Adjusting the buoyancy will have an effect on 3D control. This can be accomplished with mechanical deformation of the shape such as adjusting the size of an air pocket or the volume of the device itself. The density of the materials could also be adjusted by controlling the temperature. Additionally gases can be created from the fluid through the process of electrolysis for MHD, and these gases can adjust buoyancy.

Adjustment of the exterior shape of the body can accomplish different objectives, including having an effect on or adjusting buoyancy, minimizing drag, controlling drag, as well as creating lift forces or other steering forces.

The devices described herein can be used in numerous different environments, One class of environments relate to the body of an animal, including a human, such as most body cavities, digestive system, circulatory system, bladder, nasal cavity, ear canal, brain electrodes/devices. Another class of environments relates to industrial operations, such as pumps/compressors, water treatment, seawater, pipelines, etc.

Multiple different devices can also be used within the same environment. Each are independently controllable, provide for independent communication (being independently addressable), and can be fitted with sensors, actuators, active circuit elements, cameras, or cargo (such as drugs).

The material used to build the body will differ depending upon the environment in which it is used. For body environments, for example, biocompatible plastics/materials (such as PVC) for encapsulation, can be used. Non-magnetic materials are preferred because they do not interfere with the exterior magnetic field. Different materials can also be chosen based upon buoyancy characteristics.

The overall size of these devices can also be scaled for large and small applications, down to sub-mm sizes if needed.

Both locomotion methods could also be used to reposition specific elements attached to the main device independently, and such adjustments could apply to the antenna, sensors, actuators, active circuit elements, cameras, or cargo to improve their functionality without disturbing the position and orientation of the main device.

Further, single devices that each use both MHD and AFD for overall control and positioning of the device are within the intended scope of the present invention.

Figure 48:
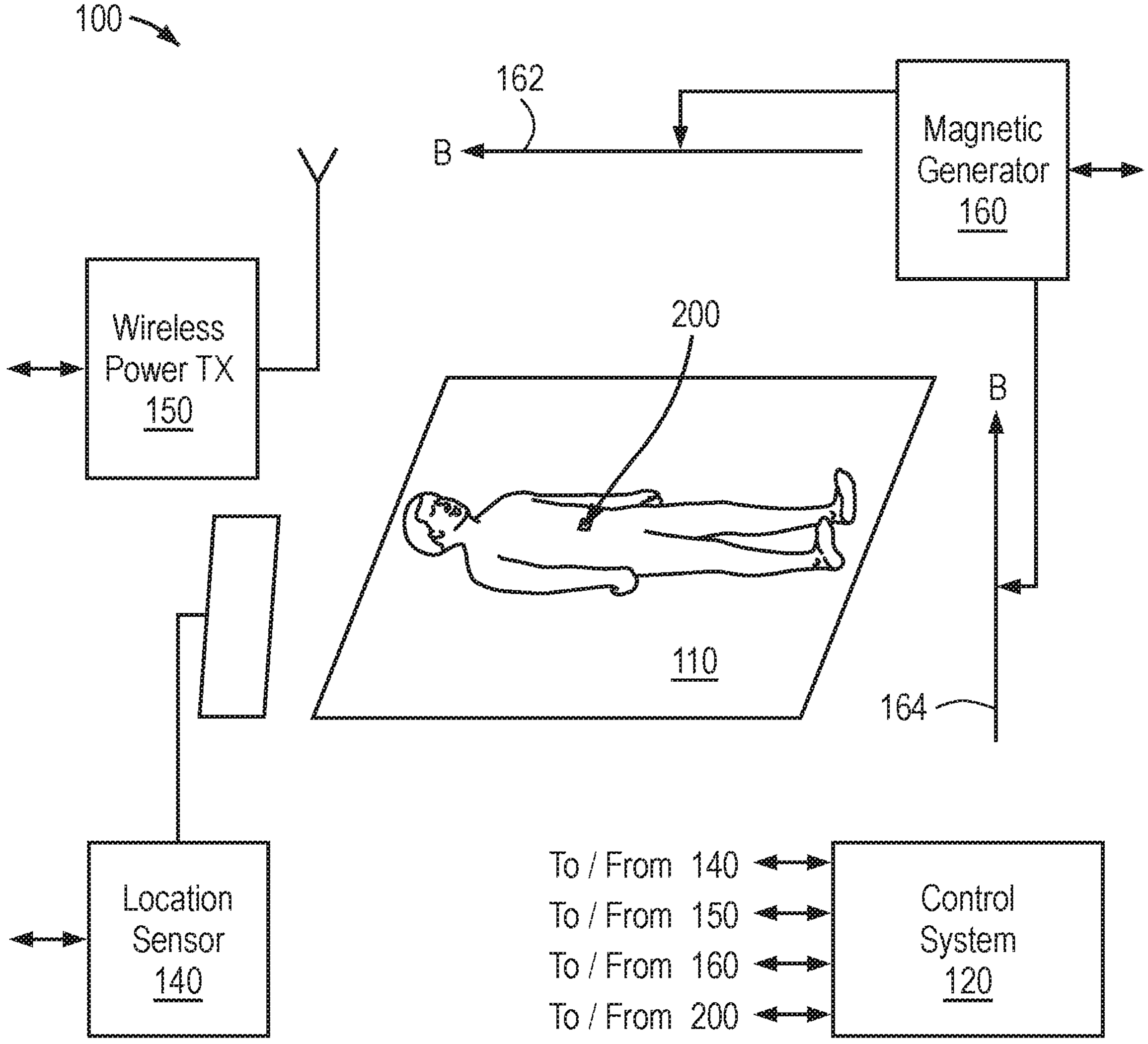
FIG. 48 illustrates a system diagram of one embodiment of an implant system.

Referring now to FIG. 48, FIG. 48 illustrates a system diagram of one embodiment of a locomotive implant system 100, which utilizes one or more of the embodiments describe above. As shown, there exists an area 110 on which a live person 120 is disposed, though the present invention can operate with other animal species, as well as in and with other non-living environments, such as plumbing systems, pumps, compressors, other industrial equipment, mobile smart dust/sensors (like Berkeley motes, but with motion). Within the arca 110 is a central control system 120, which contains a processor, memory and other well-known computer functions, in order to execute the functionality described herein, typically in the form of application software written to monitor the power and magnetic fields as described herein, as well as monitor the locomotive implant described herein, in order to control the transmitted power, the applied magnetic field, as well as the various mechanisms described herein that exist within the locomotive implant, to thereby control the movement of the locomotive implant with the body 120 of the person.

As shown, there exists a location sensor 140, which receives control signals from the central control system 120, and which essentially provides signals that can be used to detect the specific and precise position of the locomotive implant 200 within the body 120. The location sensor can be an imaging apparatus that detects the presence of the locomotive implant based upon some characteristic of the locomotive implant 200, such as the mutual inductance of the link, electromagnetic absorption, temperature difference, or scattered field from the implant. Alternatively, the location sensor 140 can be a separate imaging system such as ultrasound or MRI, or it can be based on data transmitted from the device. In each of these embodiments, precise position information is provided to the central control system 120.

Wireless power transmitter 150 is shown as well, which power transmitter transmits RF power to a power receiver disposed within the locomotive implant 200. The power transfer characteristics of the wireless power transmitter 150 are controlled by the central control system 120. The wireless power receiver within the locomotive implant is described hereinafter.

Also illustrated is the magnetic field generator 160, which is able to generate magnetic fields, preferably in two orthogonal directions, such as 162 and 164 as shown in FIG. 48, in order to allow for three directional movement as described herein. The magnetic field generator can be implemented simply using a permanent magnet or with electromagnets.

The locomotive implant system 100 described herein will enable externally controlled movement of the capsule (as the capsule becomes the locomotive implant 200), and reduces the time for the procedure and improves the accuracy of diagnosis, since the operator can drive the capsule to the areas of interest and perform careful examination of suspicious areas with optimal views. The procedure would be completed in time comparable to a regular endoscopy, in a matter of 30 minutes to an hour. In addition, the size of conventional capsules are around a couple of centimeters, with about half of the space is occupied by battery. The proposed power delivery system can reduce the size of the capsule by half. A further advantage of using locomotive implant capsule is that it can perform GI tract examinations without a full bowel prep, which is highly unpleasant for patients, by being able to navigate the locomotive implant adjacent to the wall underneath any material in the bowel. The locomotive implant system 100 described herein also has numerous surgical applications, including assisting with surgery within the abdomen without having to displace the bowel, or minimally-invasive dissection procedures for grafting.

Figure 49:
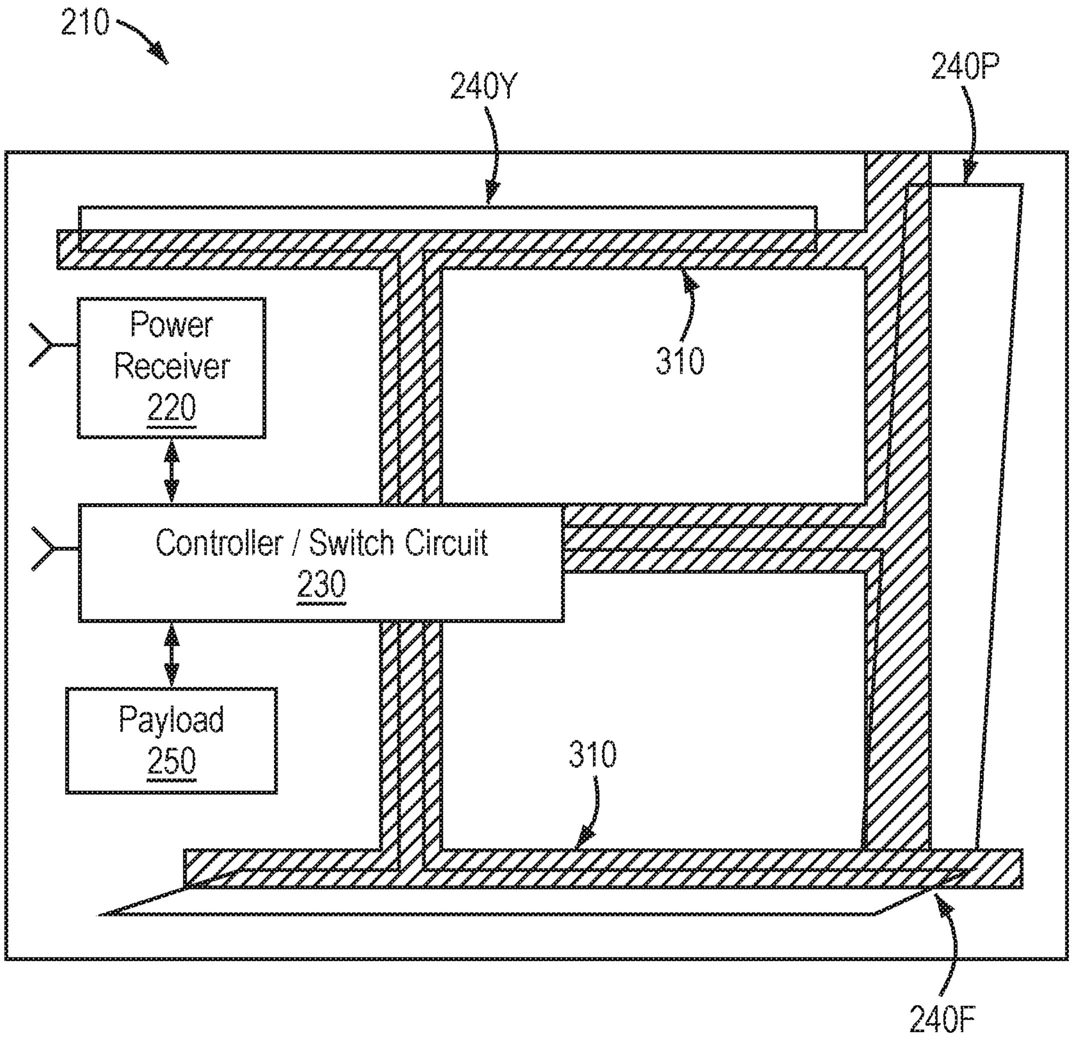
FIG. 49 illustrates a block diagram of a locomotive implant according to one embodiment.

With respect to FIG. 49, overall there exist four different primary components to the circuit 210: the power receiver 220, the locomotive implant controller 230, switchable conductors 240, and the payload 250, each of which will be discussed in more detail hereinafter.

The power receiver 220 receives power for the locomotive implant circuit 210.

In one embodiment, the power receiver 210 receives the transmitted radio frequency power signal from the wireless power transmitter 150, and converts this RF signal into electrical power.

In another embodiment in which the locomotive implant 200 is connected to another device, in order to control certain movements of the other device as described hereafter, the power receiver 220 can be wired, in which case the power receiver 220 can be implemented with essentially a wire.

The locomotive implant controller 230 receives control signals from the central control system 120 in order to control which ones of the switchable conductors 240 are turned on at any given time, in order for the appropriate motion to occur, as described further hereinafter. With respect to FIG. 49, there is shown, in simplification, an implementation of the switchable conductors implemented as a pattern with three conductive loops 240Y, 240P and 240F, which are loosely akin to Yaw, Pitch and Forward movement control, which can be used to generate movement in a desired direction, as described further hereinafter, as well as are depicted the shield regions 310 over a return length of the conductive loops as well as a routing length between the conductive loop and the control system 120, the purpose of the shield regions 310—being described hereinafter. It is understood that various arrangements of conductors 240, within the presence of the known magnetic field and a predetermined current, will provide a contribution to the overall force for movement of the implant 200, and that as such complicated structures of conductors 240 can be created to enhance movement as desired.

In certain embodiments, the locomotive implant controller 230 can also receive payload control signals, to control what to do with a payload 250, if any. Before discussing payloads, it should also be recognized that the locomotive implant controller 230 can also transmit control signals back to the central control system 120. Such control signals can be used to assist in providing for the location of the locomotive implant 200 within the body 120, and also can be used to indicate that each of the different components is operating properly. In one embodiment, if for some reason one of the switchable conductors 240 is malfunctioning, implant controller 230 can indicate such malfunction to the central control system 120, which can then determine alternative combinations of switchable conductors 240 to use to obtain a substantially equivalent force as needed for movement of locomotive implant 200.

A particular application of the implant system 100 is to enable capsule endoscopy with active movement capabilities. Conventional clinical capsule endoscopy products are passive, with motion driven by the natural GI peristalsis and therefore effectiveness depends on the random accumulation of images during the 8-24 hours that the capsule passes through the GI tract. A major limitation is that the capsule may not be oriented properly in a particular location to "see" a tumor. Since the movement of the capsule is not controllable, extended observation of interested spots along the GI tract is impossible. This application, and some of the others mentioned below, may require a "charging" device. Since the power continuously delivered to the implant may not be high enough to provide, e.g., illumination for imaging. A charging device, such as a capacitor, can accumulate the power over time and deliver a higher power when illumination is needed.

The locomotive implant system 100 described herein will enable externally controlled movement of the capsule (as the capsule becomes the locomotive implant 200), and reduces the time for the procedure and improves the accuracy of diagnosis, since the operator can drive the capsule to the areas of interest and perform careful examination of suspicious areas with optimal views. The procedure would be completed in time comparable to a regular endoscopy, in a matter of 30 minutes to an hour. In addition, the size of conventional capsules are around a couple of centimeters, with about half of the space is occupied by battery. The proposed power delivery system can reduce the size of the capsule by half. A further advantage of using locomotive implant capsule is that it can perform GI tract examinations without a full bowel prep, which is highly unpleasant for patients, by being able to navigate the locomotive implant adjacent to the wall underneath any material in the bowel.

The locomotive implant system 100 described herein also has numerous surgical applications, including assisting with surgery within the abdomen without having to displace the bowel, or minimally-invasive dissection procedures for grafting. Since the locomotive implant 200 is also a power source, besides facilitating drug delivery, cutting, ablation, and suturing during surgery, these implants 200 can also be used as small light sources to give optimal illumination for the surgeon to navigate around specific locations of interest (this application will require the charging device mentioned earlier). With external motion control, the implants can be driven to different areas and oriented for better visualization.

As is shown by the above, depending upon the payload 250, the same structure can be used to implement a number of different purposes.

As also apparent, the locomotive implant 200 can create a force within fluid environments of liquids as well as gases. Thus, within a GI tract, or with the vascular space, particularly the venous system, control of the locomotive implant 200 is akin to a submersible vessel. Within a fluid gaseous environment, such as within a lung, typically the locomotive implant 200 will require affixation to another device, and provide fine control of another device that can support the implant within a particular point within a particular plane of the fluid gaseous environment.

Although the present invention has been particularly described with reference to embodiments thereof, it should be readily apparent to those of ordinary skill in the art that various changes, modifications and substitutes are intended within the form and details thereof, without departing from the spirit and scope of the invention. Accordingly, it will be appreciated that in numerous instances some features of the invention will be employed without a corresponding use of other features. Further, those skilled in the art will understand that variations can be made in the number and arrangement of components illustrated in the above figures. It is intended that the scope of the appended claims include such changes and modifications.

The invention claimed is:

1. An apparatus for wireless power and data transfer to an implantable device operating in a biological environment, the apparatus comprising:

a wireless power transmitter operating at a power signal frequency and having one or more transmitting antennae configured to transmit a power signal modulated with data over a carrier signal and a transceiver locator for detecting a backscattered signal from the implantable device, wherein the transceiver locator is configured to determine a position of one or more receiving antennae of the implantable device using the backscattered signal; and a wireless power receiver having the one or more receiving antennae configured to receive the transmitted power signal as the received power signal, wherein the wireless power receiver is integrated into the implantable device, wherein the implantable device further comprises:

a demodulator that decodes data modulated on the power signal without synchronizing to the carrier signal.

2. The apparatus according to claim 1, wherein the carrier signal is an RF carrier signal.

3. The apparatus according to claim 1, wherein the implantable device further comprises a rectifier, a regulator, and a digital controller, and a charging device that accumulates energy over time.

4. The apparatus according to claim 1, wherein the power signal frequency has a wavelength usable in the biological environment, and the wireless power transmitter and the wireless power receiver are spaced apart by a distance in the range between wavelength/100 and wavelength*100.

5. The apparatus according to claim 1 further comprising:

a medical device attached to the implantable device; and a data link that remotely programs the medical device and retrieves information from the medical device.

6. The apparatus according to claim 5, wherein the data link supports two-way encryption.

7. The apparatus according to claim 1 further comprising:

an adaptive match transmit circuit with a tunable impedance, wherein the adaptive match transmit circuit is in communication with the wireless power transmitter; and an adaptive match receive circuit in communication with the wireless power receiver, wherein the adaptive match receive circuit receives the received power signal, and is configured to match the tunable impedance.

8. The apparatus according to claim 7, wherein the adaptive match receive circuit is configured to match the tunable impedance based on the environment of unknown transmission characteristics to thereby increase a gain of the received power signal.

9. The apparatus according to claim 1, wherein the wireless power transmitter is configured to receive data transferred from the implantable device by varying impedance of the one or more receiving antennae.

10. An apparatus for adjusting power transmission to an implantable device operating in a biological environment, the apparatus comprising:

a wireless power transmitter operating at a power signal frequency and having:

(a) one or more transmitting antennae configured to transmit a power signal, and (b) a circuit for receiving a feedback signal from the implantable device, wherein the circuit is configured to constantly monitor the feedback signal to control a transmitted power signal that causes an increase or adjusted power transfer to one or more receiving antennae of the implantable device throughout the period of usage of the implantable device; and a wireless power receiver integrated with the implantable device having the one or more receiving antennae configured to receive the transmitted power signal as a received power signal, wherein the feedback signal from the implantable device is encoded by varying an impedance of the wireless power receiver; and wherein the feedback signal is used to control the transmitted power signal, and wherein the wireless power receiver is configured for the feedback signal to provides an indication of a gain of the received power signal.

11. The apparatus according to claim 10, wherein the circuit for receiving the feedback signal is configured to adjust the gain by applying one or more of: (a) impedance matching between the wireless power transmitter and the wireless power receiver, (b) beam forming by repositioning the wireless power receiver, or (c) tuning the power signal frequency.

12. The apparatus according to claim 10, wherein the circuit for receiving the feedback signal is configured to control of the transmitted power signal by maximizing a gain of the received power signal.

13. The apparatus according to claim 10, wherein the power signal frequency has a wavelength usable in the biological environment, and the wireless power transmitter and the wireless power receiver are spaced apart by a distance in the range between wavelength/100 and wavelength*100.

* * * * *